United States Patent
Hirai et al.

(10) Patent No.: US 12,295,306 B2
(45) Date of Patent: May 13, 2025

(54) STEVIA PLANT HAVING LESS ABILITY TO FORM FLOWER BUDS

(71) Applicant: SUNTORY HOLDINGS LIMITED, Osaka (JP)

(72) Inventors: Tadayoshi Hirai, Kyoto (JP); Kazunari Iwaki, Kanagawa (JP); Kentaro Ochiai, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 484 days.

(21) Appl. No.: 17/601,579

(22) PCT Filed: Apr. 7, 2020

(86) PCT No.: PCT/JP2020/015728
§ 371 (c)(1),
(2) Date: Oct. 5, 2021

(87) PCT Pub. No.: WO2020/209265
PCT Pub. Date: Oct. 15, 2020

(65) Prior Publication Data
US 2022/0201955 A1   Jun. 30, 2022

(30) Foreign Application Priority Data

Apr. 11, 2019   (JP) ................. 2019-075610

(51) Int. Cl.
*A01H 6/14*      (2018.01)
*A01H 3/04*      (2006.01)
*A23L 33/105*    (2016.01)
*C12Q 1/6895*    (2018.01)

(52) U.S. Cl.
CPC ............. *A01H 6/14* (2018.05); *A01H 3/04* (2013.01); *C12Q 1/6895* (2013.01); *A23L 33/105* (2016.08); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2016/0021918 A1 | 1/2016 | Brower, III et al. |
| 2020/0170209 A1 | 6/2020 | Iwaki et al. |
| 2020/0281141 A1 | 9/2020 | Iwaki et al. |
| 2021/0246517 A1 | 8/2021 | Hirai et al. |

FOREIGN PATENT DOCUMENTS

| | | | |
|---|---|---|---|
| EP | 2 966 990 | 1/2016 | |
| EP | 3 569 707 | 11/2019 | |
| EP | 3 695 714 | 8/2020 | |
| EP | 3 831 960 | 6/2021 | |
| JP | 2005295878 A * | 10/2005 | |
| JP | 2016-515814 | 6/2016 | |
| WO | 99/49724 A1 | 10/1999 | |
| WO | 2014/146084 | 9/2014 | |
| WO | WO-2016049531 A1 * | 3/2016 | ............... A01H 1/02 |
| WO | 2018/124142 | 7/2018 | |
| WO | 2019/074089 | 4/2019 | |
| WO | 2020/027155 | 2/2020 | |

OTHER PUBLICATIONS

Collard et al., 2005, Euphytica 142: 169-196; (Year: 2005).*
International Search Report issued in PCT/JP2020/015728, dated Jul. 7, 2020, along with an English-language translation.
Pin et al., "The Multifaceted Roles of Flowering Locus T in Plant Development", *Plant, Cell and Environment*, vol. 35, pp. 1742-1755 (2012).
Singh et al., "Comparative Transcriptome Analysis Revealed Gamma-Irradiation Mediated Disruption of Floral Integrator Gene(s) Leading to Prolonged Vegetative Phase in *Stevia rebaudiana* Bertoni", *Plant Physiology and Biochemistry*, vol. 148, pp. 90-102 (2020).
Extended European Search Report issued in EP Patent Application No. 20786991.8, dated Dec. 22, 2022.

* cited by examiner

*Primary Examiner* — Brent T Page
*Assistant Examiner* — Aleksandar Radosavljevic
(74) *Attorney, Agent, or Firm* — IGREENBLUM & BERNSTEIN, P.L.C.

(57) ABSTRACT

The present invention provides a *stevia* plant having a low ability to form flower buds as compared with the wild type *stevia* species. The present invention also provides a method of producing such a *stevia* plant having a low ability to form flower buds, and an extract or a steviol glycoside purified product obtainable from such a plant.

17 Claims, 2 Drawing Sheets
Specification includes a Sequence Listing.

STEVIA PLANT HAVING LESS ABILITY TO FORM FLOWER BUDS

TECHNICAL FIELD

The present invention relates to a *stevia* plant having a low ability to form flower buds, a method for producing the same and a method for screening for the same, etc.

BACKGROUND ART

*Stevia* is a perennial plant of the family Asteraceae with Paraguay in the South America as its place of origin. *Stevia* contains a sweet component having several tens to several hundreds of times the sweetness of sugar, and such a sweet component is extracted therefrom and used as a natural sweetener (Patent Literature 1). However, much remains unknown about gene information or what kind of gene is involved in the control of in vivo events in *stevia*, for example.

CITATION LIST

Patent Literature

Patent Literature 1: WO2018/124142

SUMMARY OF INVENTION

Technical Problem

It is desired to further elucidate gene information on *stevia*.

Means for Solving the Problems

The present invention provides a *stevia* plant having a low ability to form flower buds, a method of producing the plant, and a method of screening for the plant, etc.

In one embodiment, the present invention provides the following.

[1] A *stevia* plant having a low ability to form flower buds as compared with the wild type.

[2] The plant according to [1], wherein the plant is heterozygous or homozygous for the allele wherein the base at the position corresponding to position 90 of SEQ ID NO: 150 is G, and/or is heterozygous or homozygous for the allele wherein the base at the position corresponding to position 108 of SEQ ID NO: 150 is G.

[3] The plant according to [1] or [2], further having at least one of the following genetic features (1) to (7).

(1) Homozygous for the allele wherein the base at the position corresponding to position 40 of SEQ ID NO: 2 is T.

(2) Homozygous for the allele wherein the base at the position corresponding to position 44 of SEQ ID NO: 3 is T.

(3) Homozygous for the allele wherein the base at the position corresponding to position 41 of SEQ ID NO: 4 is C.

(4) Homozygous for the allele wherein the portion corresponding to positions 55-72 of SEQ ID NO: 5 is deleted.

(5) Homozygous for the allele wherein the base at the position corresponding to position 201 of SEQ ID NO: 1 is A.

(6) Heterozygous for the allele wherein the base at the position corresponding to position 49 of SEQ ID NO: 6 is A.

(7) Homozygous for the allele wherein the base at the position corresponding to position 49 of SEQ ID NO: 6 is A.

[4] The plant according to [3], having at least one of the following features (1) and (2).

(1) Comprising 3% or more of RebD per unit mass of a dried leaf.

(2) Comprising 0.2% or more of RebM per unit mass of a dried leaf.

[5] The plant according to any one of [1] to [4], wherein the plant is a non-genetically modified plant.

[6] The plant according to any one of [1] to [5], wherein the plant comprises a *stevia* plant subjected to a mutagenesis treatment and a progeny plant thereof.

[7] A seed, a tissue, a tissue culture or a cell of the plant according to any one of [1] to [6].

[8] The tissue, tissue culture or cell according to [7], which is selected from an embryo, a meristem cell, a pollen, a leaf, a root, a root apex, a petal, a protoplast, a leaf section and a callus.

[9] A method of producing a *stevia* plant having a low ability to form flower buds, the method comprising a step of crossing the plant according to any one of [1] to [6] with a second *stevia* plant.

[10] The method according to [9], wherein the second plant is the plant according to any one of [1] to [6].

[11] An extract of the plant according to any one of [1] to [6], or of the seed, tissue, tissue culture or cell according to [7] or [8].

[12] A method of producing a *stevia* extract, comprising a step of obtaining an extract from the plant according to any one of [1] to [6], or from the seed, tissue, tissue culture or cell according to [7] or [8].

[13] A method of producing a steviol glycoside purified product, comprising: a step of obtaining an extract from the plant according to any one of [1] to [6], or from the seed, tissue, tissue culture or cell according to [7] or [8]; and a step of purifying a steviol glycoside from the obtained extract.

[14] The method according to [13], wherein the steviol glycoside comprises rebaudioside A, rebaudioside B, rebaudioside C, rebaudioside D, rebaudioside E, rebaudioside F, rebaudioside M, rebaudioside N, rebaudioside O, stevioside, steviolbioside, rubusoside, dulcoside A or a combination thereof.

[15] A method of producing a food or beverage, a sweetener composition, a flavor or a medicament, comprising:

a step of providing the extract according to [11], or a purified product thereof; and a step of adding the extract or the purified product to a raw material for the food or beverage, sweetener composition, flavor or medicament.

[16] A method of screening for a *stevia* plant with a low ability to form flower buds, comprising a step of detecting from the genome of a test *stevia* plant the presence and/or the absence of a genetic feature of being heterozygous or homozygous for the allele wherein the base at the position corresponding to position 90 of SEQ ID NO: 150 is G, and/or the base at the position corresponding to position 108 of SEQ ID NO: 150 is G.

[17] The method according to [16], further comprising a step of detecting from the genome of a test *stevia* plant the presence and/or the absence of the following genetic features (1) to (7).

(1) Homozygous for the allele wherein the base at the position corresponding to position 40 of SEQ ID NO: 2 is T.

(2) Homozygous for the allele wherein the base at the position corresponding to position 44 of SEQ ID NO: 3 is T.

(3) Homozygous for the allele wherein the base at the position corresponding to position 41 of SEQ ID NO: 4 is C.

(4) Homozygous for the allele wherein the portion corresponding to positions 55-72 of SEQ ID NO: 5 is deleted.

(5) Homozygous for the allele wherein the base at the position corresponding to position 201 of SEQ ID NO: 1 is A.

(6) Heterozygous for the allele wherein the base at the position corresponding to position 49 of SEQ ID NO: 6 is A from the genome of the test *stevia* plant.

(7) Homozygous for the allele wherein the base at the position corresponding to position 49 of SEQ ID NO: 6 is A from the genome of the test *stevia* plant.

[18] The method according to [16] or [17], wherein the step of detecting a genetic feature is performed by use of CAPS method, dCAPS method or TaqMan PCR method.

[19] The method according to any one of [16] to [18], further comprising a step of evaluating the ability to form flower buds in a test *stevia* plant tissue.

[20] A screening kit for a *stevia* plant with a low ability to form flower buds, comprising a reagent for detecting the presence and/or the absence of a genetic feature of being heterozygous or homozygous for the allele wherein the base at the position corresponding to position 90 of SEQ ID NO: 150 is G, and/or being heterozygous or homozygous for the allele wherein the base at the position corresponding to position 108 of SEQ ID NO: 150 is G.

[21] The kit according to [20], further comprising a reagent for detecting the presence and/or the absence of the following genetic features (1) to (7).

(1) Homozygous for the allele wherein the base at the position corresponding to position 40 of SEQ ID NO: 2 is T.

(2) Homozygous for the allele wherein the base at the position corresponding to position 44 of SEQ ID NO: 3 is T.

(3) Homozygous for the allele wherein the base at the position corresponding to position 41 of SEQ ID NO: 4 is C.

(4) Homozygous for the allele wherein the portion corresponding to positions 55-72 of SEQ ID NO: 5 is deleted.

(5) Homozygous for the allele wherein the base at the position corresponding to position 201 of SEQ ID NO: 1 is A.

(6) Heterozygous for the allele wherein the base at the position corresponding to position 49 of SEQ ID NO: 6 is A.

(7) Homozygous for the allele wherein the base at the position corresponding to position 49 of SEQ ID NO: 6 is A.

[22] The kit according to [20] or [21], wherein the reagent comprises a primer and/or a probe for use in CAPS method, dCAPS method or TaqMan PCR method.

[23] A method of producing a *stevia* plant with a low ability to form flower buds, comprising a step of introducing a variation from A to G to a position corresponding to position 90 of SEQ ID NO: 150, and/or a step of introducing a variation from T to G to a position corresponding to position 108 of SEQ ID NO: 150.

[24] The method according to [23], wherein the introduction of the variation is performed by a mutagenesis treatment.

Advantageous Effects of Invention

The present invention enables the obtainment of a *stevia* plant having a low ability to form flower buds and the provision of an approach for producing such a plant, a leaf obtainable from such a plant, and a food, a drink, etc. containing an extract obtained from this leaf. When the ability to form flower buds is low, nutrients that are supposed to be used for flower bud formation are used in leaf growth. Thus, improvement in leaf productivity and by extension, increase in contents of steviol glycosides accumulated in leaves can be expected.

DESCRIPTION OF EMBODIMENTS

Figure 1:
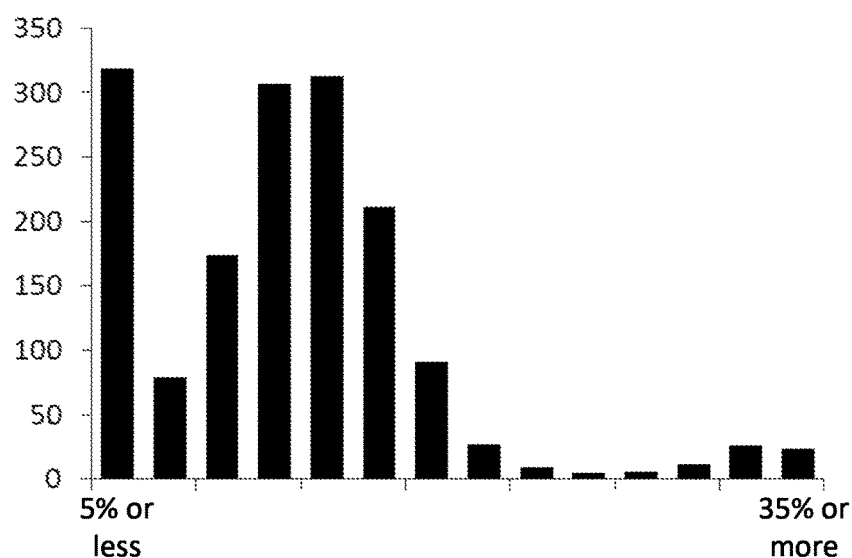
FIG. 1 is a diagram showing a frequency distribution of sweet component contents in M1 generation individuals. The ordinate depicts the number of individuals, and the abscissa depicts a sweet component concentration (%) in a dried leaf.

The present invention will now be described in detail. The following embodiments are provided for illustrating the present invention and are not intended to limit the present invention only thereto. The present invention may be implemented in various forms, without departing from the spirit of the present invention.

Note that all documents, as well as laid-open application publications, patent application publications, and other patent documents cited herein shall be incorporated herein by reference. The present specification incorporates the contents of the specification and the drawings of Japanese Patent Application No. 2019-075610, filed on Apr. 11, 2019, from which the present application claims priority.

1. *Stevia* Plant Having a Low Ability to Form Flower Buds

The present invention provides a *stevia* plant having a low ability to form flower buds as compared with the wild type (hereinafter, generically referred to as the "plant of the present invention" or "*stevia* plant of the present invention").

*Stevia* is a plant having a scientific name of *Stevia rebaudiana* Bertoni.

The phrase "having a low ability to form flower buds as compared with the wild type" means that the number of flower buds formed for a predetermined period is smaller than that of the wild type *stevia* plant when the plants to be compared are cultivated, for example, under short-day conditions and under the same cultivation conditions. More specifically, the phrase means that the number of flower buds formed for a predetermined period is smaller by 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or 100% than that of the wild type *stevia* plant when the plants to be compared are cultivated, for example, under short-day conditions and under the same cultivation conditions. The phrase "smaller by 100%" means that no flower bud is formed (i.e., the number of flower buds is 0) while the wild type *stevia* plant has one or more formed flower buds. The short-day conditions involve a dark phase of longer than 10 hours, preferably 11 hours or longer. The predetermined period means a period for which the wild type *stevia* plant forms flower buds under short-day conditions, and may be, for example, 2 weeks, 3 weeks, or 4 weeks. Also, 5 or less, for example, 5, 4, 3, 2, 1 or 0 flower buds after cultivation for 3 weeks under conditions of a 12-hour light phases, or 10 or less, for example, 10, 9, 8, 7, 6, 5, 4, 3, 2, 1 or 0 flower buds after cultivation for 3 weeks under conditions of an 8-hour light phases may be used as an alternative index for the phrase "having a low ability to form flower buds as compared with the wild type".

In one embodiment, the *stevia* plant of the present invention has at least one genetic feature (hereinafter, referred to as the "genetic feature X of the present invention") selected from a genetic feature of being homozygous or heterozygous for the allele wherein the base at the position corresponding to position 90 of SEQ ID NO: 150 is G (hereinafter, referred to as the "genetic feature X-1 of the present invention") and a genetic feature of being homozygous or heterozygous for the allele wherein the base at the position corresponding to position 108 of SEQ ID NO: 150 is G (hereinafter, referred to as the "genetic feature X-2 of the present invention").

In one embodiment, the *stevia* plant of the present invention has a genetic feature of being homozygous for the allele wherein the base at the position corresponding to position 201 of SEQ ID NO: 1 is A (hereinafter, referred to as the "genetic feature A of the present invention").

In another embodiment, the *stevia* plant of the present invention has at least one of the following genetic features (B-1) to (B-4) (hereinafter, referred to as the "genetic feature B of the present invention").

(B-1) Homozygous for the allele wherein the base at the position corresponding to position 40 of SEQ ID NO: 2 is T (hereinafter, referred to as the "genetic feature B-1 of the present invention").

(B-2) Homozygous for the allele wherein the base at the position corresponding to position 44 of SEQ ID NO: 3 is T (hereinafter, referred to as the "genetic feature B-2 of the present invention").

(B-3) Homozygous for the allele wherein the base at the position corresponding to position 41 of SEQ ID NO: 4 is C (hereinafter, referred to as the "genetic feature B-3 of the present invention").

(B-4) Homozygous for the allele wherein the portion corresponding to positions 55-72 of SEQ ID NO: 5 is deleted (hereinafter, referred to as the "genetic feature B-4 of the present invention").

In an alternative embodiment, the *stevia* plant of the present invention has a genetic feature of being heterozygous for the allele wherein the base at the position corresponding to position 49 of SEQ ID NO: 6 is A (hereinafter, referred to as the "genetic feature C of the present invention").

In an alternative embodiment, the *stevia* plant of the present invention has a genetic feature of being homozygous for the allele wherein the base at the position corresponding to position 49 of SEQ ID NO: 6 is A (hereinafter, referred to as the "genetic feature D of the present invention").

In a preferable embodiment, the *stevia* plant of the present invention has the genetic feature X (i.e., at least one of the genetic features X-1 and X-2 of the present invention) and the genetic feature A of the present invention. In another preferable embodiment, the *stevia* plant of the present invention has the genetic feature X and the genetic feature B (i.e., at least one of the genetic features B-1 to B-4 of the present invention) of the present invention. In an alternative preferable embodiment, the *stevia* plant of the present invention has the genetic feature X and the genetic feature C or D of the present invention. In an alternative preferable embodiment, the *stevia* plant of the present invention has the genetic feature X, the genetic feature A, and the genetic feature B of the present invention. In an alternative preferable embodiment, the *stevia* plant of the present invention has, the genetic feature X, the genetic feature A, and the genetic feature C or D of the present invention. In an alternative preferable embodiment, the *stevia* plant of the present invention has the genetic feature X, the genetic feature B, and the genetic feature C or D of the present invention. In a more preferable embodiment, the *stevia* plant of the present invention has all of the genetic features X, A, B and C or D of the present invention.

The phrase "position (or portion) corresponding to" means the following. In case a sequence identical to a reference sequence (e.g., SEQ ID NOs: 1 to 6, 150 etc.) is present in the genome, it means a position or a portion in the sequence (e.g., 201, 40, 44, 41, 55-72, 49, 90/108, etc.) present in the genome, and in case a sequence identical to the reference sequence is not present in the genome, it means a position or portion in a sequence in the genome corresponding to the reference sequence, which corresponds to the position or portion in the reference sequence. Whether or not a sequence identical to or corresponding to the reference sequence exists in the genome can be determined by, for example, amplifying genomic DNA of the *stevia* plant of interest with a primer capable of amplifying the reference sequence by PCR, sequencing the amplified product, and performing alignment analysis between the obtained sequence and the reference sequence. Non-limiting examples of a sequence corresponding to a reference sequence include, for example, a nucleotide sequence having a sequence identity of 60% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.1% or more, 98.4% or more, 98.7% or more, 99% or more, 99.2% or more, 99.5% or more, or 99.8% or more to the reference sequence. The position or portion corresponding to the position or portion in the reference sequence in the sequence corresponding to the reference sequence in the genome can be determined by taking into account the nucleotide sequence before and after the position or portion in the reference sequence and the like. For example, a position or portion in the sequence corresponding to the reference sequence in the genome corresponding to a position or portion in the reference sequence can be determined by an alignment analysis of a reference sequence with a sequence corresponding to a reference sequence in the genome.

For instance, when taking "the position corresponding to position 201 of SEQ ID NO: 1" of the genetic feature A of the present invention as an example, in case the genome of a *stevia* plant has a portion consisting of a nucleotide sequence identical to SEQ ID NO: 1, "the position corresponding to position 201 of SEQ ID NO: 1" is position 201 from the 5' end of the portion consisting of a nucleotide sequence identical to SEQ ID NO: 1 in the genome. On the other hand, in case the genome of a *stevia* plant has a portion consisting of a nucleotide sequence which is not identical to, but which corresponds to SEQ ID NO: 1, the genome does not have a portion consisting of a nucleotide sequence identical to SEQ ID NO: 1. Therefore, "the position corresponding to position 201 of SEQ ID NO: 1" does not necessarily correspond to position 201 from the 5' end of the portion corresponding to SEQ ID NO: 1. However, it is possible to identify "the position corresponding to position 201 of SEQ ID NO: 1" in the genome of such a *stevia* plant by taking into account the nucleotide sequence before and after the position 201 of SEQ ID NO: 1, and the like. For instance, one can identify "the position corresponding to position 201 of SEQ ID NO: 1" in the genome of a *stevia* plant by an alignment analysis of the nucleotide sequence of a portion corresponding to SEQ ID NO: 1" in the genome of a *stevia* plant and the nucleotide sequence of SEQ ID NO: 1.

"The portion consisting of a nucleotide sequence corresponding to SEQ ID NO: 1" means, for instance, a portion consisting of a nucleotide sequence having a sequence identity of 60% or more, 70% or more, 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 98.1% or more, 98.4% or more, 98.7% or more, 99% or more, 99.2% or more, 99.5% or more, or 99.8% or more to the nucleotide sequence of SEQ ID NO: 1.

In one embodiment, "the portion consisting of a nucleotide sequence corresponding to SEQ ID NO: 1" includes a portion of the genome of a *stevia* plant which can be amplified by PCR using a forward primer which hybridizes to a complementary sequence of a portion of 15 to 25 base long from the 5' end of SEQ ID NO: 1 and a reverse primer which hybridizes to a portion of 15 to 25 base long from the 3' end of SEQ ID NO: 1.

For simplicity, the genetic feature A of the present invention is used here as an example for explanation, but the same applies to the genetic features X (including genetic features X-1 and X-2), B (including the genetic features B-1 to B-4), C and D of the present invention.

In a specific embodiment, "the portion consisting of a nucleotide sequence corresponding to SEQ ID NO: 150" includes, for instance, a portion of the genome of a *stevia* plant which can be amplified by PCR using a forward primer comprising the nucleotide sequence of SEQ ID NO: 151 and a reverse primer comprising the nucleotide sequence of SEQ ID NO: 152.

In a specific embodiment, "the portion consisting of a nucleotide sequence corresponding to SEQ ID NO: 1" includes, for instance, a portion of the genome of a *stevia* plant which can be amplified by PCR using a forward primer comprising the nucleotide sequence of SEQ ID NO: 7 and a reverse primer comprising the nucleotide sequence of SEQ ID NO: 8.

In a specific embodiment, "the portion consisting of a nucleotide sequence corresponding to SEQ ID NO: 2" includes, for instance, a portion of the genome of a *stevia* plant which can be amplified by PCR using a forward primer comprising the nucleotide sequence of SEQ ID NO: 9 and a reverse primer comprising the nucleotide sequence of SEQ ID NO: 10.

In a specific embodiment, "the portion consisting of a nucleotide sequence corresponding to SEQ ID NO: 3" includes, for instance, a portion of the genome of a *stevia* plant which can be amplified by PCR using a forward primer comprising the nucleotide sequence of SEQ ID NO: 11 and a reverse primer comprising the nucleotide sequence of SEQ ID NO: 12.

In a specific embodiment, "the portion consisting of a nucleotide sequence corresponding to SEQ ID NO: 4" includes, for instance, a portion of the genome of a *stevia* plant which can be amplified by PCR using a forward primer comprising the nucleotide sequence of SEQ ID NO: 13 and a reverse primer comprising the nucleotide sequence of SEQ ID NO: 14.

In a specific embodiment, "the portion consisting of a nucleotide sequence corresponding to SEQ ID NO: 5" includes, for instance, a portion of the genome of a *stevia* plant which can be amplified by PCR using a forward primer comprising the nucleotide sequence of SEQ ID NO: 15 and a reverse primer comprising the nucleotide sequence of SEQ ID NO: 16.

In a specific embodiment, "the portion consisting of a nucleotide sequence corresponding to SEQ ID NO: 6" includes, for instance, a portion of the genome of a *stevia* plant which can be amplified by PCR using a forward primer comprising the nucleotide sequence of SEQ ID NO: 17 and a reverse primer comprising the nucleotide sequence of SEQ ID NO: 18.

In a specific embodiment, "the allele wherein the base at the position corresponding to position 90 of SEQ ID NO: 150 is G" comprises the nucleotide sequence of SEQ ID NO: 153 or 154.

In a specific embodiment, "the allele wherein the base at the position corresponding to position 108 of SEQ ID NO: 150 is G" comprises the nucleotide sequence of SEQ ID NO: 155 or 156.

In a specific embodiment, "the allele wherein the base at the position corresponding to position 201 of SEQ ID NO: 1 is A" comprises the nucleotide sequence of SEQ ID NO: 19, 20 or 21.

In a specific embodiment, "the allele wherein the base at the position corresponding to position 40 of SEQ ID NO: 2 is T" comprises the nucleotide sequence of SEQ ID NO: 22, 23 or 24.

In a specific embodiment, "the allele wherein the base at the position corresponding to position 44 of SEQ ID NO: 3 is T" comprises the nucleotide sequence of SEQ ID NO: 25, 26 or 27.

In a specific embodiment, "the allele wherein the base at the position corresponding to position 41 of SEQ ID NO: 4 is C" comprises the nucleotide sequence of SEQ ID NO: 28, 29 or 30.

In a specific embodiment, "the allele wherein the portion corresponding to positions 55-72 of SEQ ID NO: 5 is deleted" comprises the nucleotide sequence of SEQ ID NO: 31, 32 or 33.

In a specific embodiment, "the allele wherein the base at the position corresponding to position 49 of SEQ ID NO: 6 is A" comprises the nucleotide sequence of SEQ ID NO: 34, 35 or 36.

Here, a position selected from the group consisting of (X-1) a position corresponding to position 90 of SEQ ID NO: 150, (X-2) a position corresponding to position 108 of SEQ ID NO: 150, (A) a position corresponding to position 201 of SEQ ID NO: 1, (B-1) a position corresponding to position 40 of SEQ ID NO: 2, (B-2) a position corresponding to position 44 of SEQ ID NO: 3, (B-3) a position corresponding to position 41 of SEQ ID NO: 4, (B-4) a portion corresponding to positions 55-72 of SEQ ID NO: 5, and (C) a position corresponding to position 49 of SEQ ID NO: 6 may be generically referred to as a "polymorphic site of the present invention" or a "variation site of the present invention".

Also, a variation selected from the group consisting of (X-1) a variation from A to G at a position corresponding to position 90 of SEQ ID NO: 150, (X-2) a variation from T to G at a position corresponding to position 108 of SEQ ID NO: 150, (A) a variation from C to A at a position corresponding to position 201 of SEQ ID NO: 1, (B-1) a variation from A to T at a position corresponding to position 40 of SEQ ID NO: 2, (B-2) a variation from C to T at a position corresponding to position 44 of SEQ ID NO: 3, (B-3) a variation from G to C at a position corresponding to position 41 of SEQ ID NO: 4, (B-4) a deletion of the portion corresponding to positions 55-72 of SEQ ID NO: 5, and (C) a variation from C to A at a position corresponding to position 49 of SEQ ID NO: 6 may be generically referred to as a "polymorphism of the present invention" or a "variation of the present invention".

The above genetic features can be detected by PCR method, TaqMan PCR method, sequencing method, microarray method, Invader method, TILLING method, RAD (random amplified polymorphic DNA) method, restriction fragment length polymorphism (RFLP) method, PCR-SSCP method, AFLP (amplified fragment length polymorphism) method, SSLP (simple sequence length polymorphism) method, CAPS (cleaved amplified polymorphic sequence) method, dCAPS (derived cleaved amplified polymorphic sequence) method, allele-specific oligonucleotide (ASO) method, ARMS method, denaturing gradient gel electrophoresis (DGGE) method, CCM (chemical cleavage of mismatch) method, DOL method, MALDI-TOF/MS method, TDI method, padlock probe method, molecular beacon method, DASH (dynamic allele specific hybridization) method, UCAN method, ECA method, PINPOINT method, PROBE (primer oligo base extension) method, VSET (very short extension) method, Survivor assay, Sniper assay, Luminex assay, GOOD method, LCx method, SNaPshot method, Mass ARRAY method, pyrosequencing method, SNP-IT method, melting curve analysis method, etc., but detection methods are not limited thereto.

In a specific embodiment, each genetic feature of the present invention is detectable using the following combination of a primer set and a restriction enzyme.

In case a candidate plant has the genetic feature X-1, for example, bands of approximately 90 bp long (e.g., SEQ ID NO: 160) and approximately 25 bp (e.g., SEQ ID NO: 161) are obtained by: performing PCR amplification using a forward primer having the nucleotide sequence shown in SEQ ID NO: 157 and a reverse primer having the nucleotide sequence shown in SEQ ID NO: 158 on the genomic DNA of the candidate plant; and treating the obtained PCR product (approximately 115 bp long, e.g., SEQ ID NO: 158) with a restriction enzyme AluI. On the other hand, when only a band of approximately 115 bp long (e.g., SEQ ID NO: 162) is obtained by: obtaining, for example, a PCR product (approximately 115 bp long) of SEQ ID NO: 162 by PCR amplification; and treating this PCR product with a restriction enzyme AluI, the candidate plant does not have the genetic feature X-1.

In case a candidate plant has the genetic feature X-2, for example, bands of approximately 112 bp long (e.g., SEQ ID NO: 165) and approximately 25 bp (e.g., SEQ ID NO: 166) are obtained by: performing PCR amplification using a forward primer having the nucleotide sequence shown in SEQ ID NO: 157 and a reverse primer having the nucleotide sequence shown in SEQ ID NO: 163 on the genomic DNA of the candidate plant; and treating the obtained PCR product (approximately 137 bp long, e.g., SEQ ID NO: 164) with a restriction enzyme ApaI. On the other hand, when only a band of approximately 137 bp long (e.g., SEQ ID NO: 167) is obtained by: obtaining, for example, a PCR product (approximately 137 bp long) of SEQ ID NO: 167 by PCR amplification; and treating this PCR product with a restriction enzyme ApaI, the candidate plant does not have the genetic feature X-2.

In case a candidate plant has the genetic feature A, for example, a band of approximately 96 bp long (e.g., SEQ ID NO: 41) and a band of approximately 100 bp (e.g., SEQ ID NO: 42) are obtained by: performing PCR amplification using a forward primer having the nucleotide sequence shown in SEQ ID NO: 37 and a reverse primer having the nucleotide sequence shown in SEQ ID NO: 38 on the genomic DNA of the candidate plant; and treating the obtained PCR product (approximately 196 bp long, e.g., SEQ ID NO: 39) with a restriction enzyme Hpy188I. On the other hand, when restriction enzyme-treated products of approximately 43 bp (e.g., SEQ ID NO: 43) and approximately 57 bp (e.g., SEQ ID NO: 44) are formed by: obtaining, for example, a PCR product (approximately 196 bp long) of SEQ ID NO: 40 by PCR amplification; and treating the PCR product with a restriction enzyme Hpy188I, the candidate plant does not have the genetic feature A.

In case where a candidate plant has the genetic feature B-1, for example, only a band of approximately 297 bp long (e.g., SEQ ID NO: 47) is obtained by: performing PCR amplification using a forward primer having the nucleotide sequence shown in SEQ ID NO: 45 and a reverse primer having the nucleotide sequence shown in SEQ ID NO: 46 on the genomic DNA of the candidate plant; and treating the obtained PCR product (approximately 297 bp long: e.g., SEQ ID NO: 47) with a KpnI restriction enzyme. On the other hand, when a restriction enzyme-treated product of approximately 258 bp (e.g., SEQ ID NO: 49) is formed by: obtaining, for example, a PCR product (approximately 297 bp long) of SEQ ID NO: 48 by PCR amplification; and treating the PCR product with a restriction enzyme KpnI, the candidate plant does not have the genetic feature B-1.

In case where a candidate plant has the genetic feature B-2, for example, only a band of approximately 383 bp long (e.g., SEQ ID NO: 52) is obtained by: performing PCR amplification using a forward primer having the nucleotide sequence shown in SEQ ID NO: 50 and a reverse primer having the nucleotide sequence shown in SEQ ID NO: 51 on the genomic DNA of the candidate plant; and treating the obtained PCR product (approximately 383 bp long: e.g., SEQ ID NO: 52) with an XbaI restriction enzyme. On the other hand, when a restriction enzyme-treated product of approximately 344 bp long (e.g., SEQ ID NO: 54) is formed by: obtaining, for example, a PCR product (approximately 297 bp long) of SEQ ID NO: 53 by PCR amplification; and treating the PCR product with a restriction enzyme XbaI, the candidate plant does not have the genetic feature B-2.

In case where a candidate plant has the genetic feature B-3, for example, only a band of approximately 390 bp long (e.g., SEQ ID NO: 57) is obtained by: performing PCR amplification using a forward primer having the nucleotide sequence shown in SEQ ID NO: 55 and a reverse primer having the nucleotide sequence shown in SEQ ID NO: 56 on the genomic DNA of the candidate plant; and treating the obtained PCR product (approximately 390 bp long: e.g., SEQ ID NO: 57) with an AflII restriction enzyme. On the other hand, when a restriction enzyme-treated product of approximately 347 bp long (e.g., SEQ ID NO: 59) is formed by: obtaining, for example, a PCR product (approximately 297 bp long) of SEQ ID NO: 58 by PCR amplification; and treating the PCR product with a restriction enzyme AflII, the candidate plant does not have the genetic feature B-3.

In case where a candidate plant has the genetic feature B-4, for example, only a PCR product of approximately 140 bp (e.g., SEQ ID NO: 62) is formed by performing PCR amplification using a forward primer having the nucleotide sequence shown in SEQ ID NO: 60 and a reverse primer having the nucleotide sequence shown in SEQ ID NO: 61 on the genomic DNA of the candidate plant. On the other hand, when PCR products of 140 bp long (e.g., SEQ ID NO: 62) and 158 bp long (e.g., SEQ ID NO: 63) are formed, the candidate plant does not have the genetic feature B-4.

In case a candidate plant has the genetic feature C or D, for example, a band of approximately 367 bp long (e.g., SEQ ID NO: 66) and a band of approximately 321 bp (e.g., SEQ ID NO: 68) are obtained by: performing PCR amplification using a forward primer having the nucleotide sequence shown in SEQ ID NO: 64 and a reverse primer having the nucleotide sequence shown in SEQ ID NO: 65 on the genomic DNA of the candidate plant; and treating the obtained PCR product (approximately 367 bp long: e.g., SEQ ID NO: 66) with a restriction enzyme SpeI. On the other hand, when only a restriction enzyme-treated product of approximately 367 bp long (e.g., SEQ ID NO: 67) is formed by: obtaining, for example, a PCR product (approximately 367 bp long) of SEQ ID NO: 67 by PCR amplification; and treating the PCR product with a restriction enzyme SpeI, the candidate plant has neither of genetic feature C nor D.

The term "approximately" as to bp long described above means±5 bp. The restriction enzyme treatment can be performed according to conditions recommended by the distributor of each restriction enzyme used.

The ability to form flower buds can be evaluated by, for example, any known approach or an approach described in Example 6. Non-limiting examples of the method of evaluating the ability to form flower buds include the following approach:
(1) A test *stevia* plant is cultivated for a predetermined period under short-day conditions.
(2) The number of formed flower buds is counted.

The test *stevia* plant may be cultivated alone or may be cultivated together with the wild type *stevia* plant (control) in the same environment. In the case of cultivating the test *stevia* plant alone, the evaluation approach described above may comprise step of comparing the number of flower buds formed in the test *stevia* plant with the number of flower buds formed in the wild type *stevia* plant cultivated under similar conditions (e.g., based on data obtained in a literature or a separate experiment). In the case of cultivating the test *stevia* plant together with the wild type *stevia* plant, the evaluation approach described above may comprise a step of comparing the number of flower buds formed in the test *stevia* plant with the number of flower buds formed in the wild type *stevia* plant cultivated together therewith.

The short-day conditions involve, as mentioned above, a dark phase set to longer than 10 hours, preferably 11 hours or longer. A specific length of the dark phase may be, for example, 11 hours, 12 hours, 13 hours, 14 hours, 15 hours, 16 hours, 17 hours, or 18 hours. The predetermined cultivation period is not particularly limited as long as the wild type *stevia* plant is capable of forming flower buds under short-day conditions for the period. The cultivation period may be, for example, 2 weeks, 3 weeks, or 4 weeks.

In one embodiment, the plant of the present invention comprises 3% or more of RebD per unit mass of a dried leaf. This means that, for example, RebD is contained at a ratio of 3% by mass or more (e.g., 1.5 mg or more) in a dried leaf having a predetermined mass (e.g., 50 mg). In this embodiment, the ratio of RebD per unit mass of a dried leaf is not limited and may be, for example, 3.0% or more, 3.1% or more, 3.2% or more, 3.3% or more, 3.4% or more, 3.5% or more, 3.6% or more, 3.7% or more, 3.8% or more, 3.9% or more, 4.0% or more, 4.1% or more, 4.2% or more, 4.3% or more, 4.4% or more, 4.5% or more, 4.6% or more, 4.7% or more, 4.8% or more, 4.9% or more, 5.0% or more, 5.1% or more, 5.2% or more, 5.3% or more, 5.4% or more, 5.5% or more, 5.6% or more, 5.7% or more, 5.8% or more, 5.9% or more, 6.0% or more or the like, and is preferably 3.3% or more, more preferably 3.6% or more. The upper limit of the ratio of RebD per unit mass of a dried leaf is not particularly limited and may be, for example, 20%, 15% or 10%. As shown in Examples, the genetic features A to D are highly related to this embodiment.

In this context, the dried leaf refers to a leaf having a water content decreased to 3 to 4% by weight by drying a fresh leaf of the *stevia* plant of the present invention.

In one embodiment, the plant of the present invention comprises 2.6% or more of RebD and 0.4% or more of RebM per unit mass of a dried leaf. This means that, for example, RebD and RebM are contained at ratios of 2.6% by mass or more (e.g., 1.3 mg or more per 50 mg of a dried leaf) and 0.4% by mass or more (e.g., 0.2 mg or more per 50 mg of a dried leaf), respectively, in a dried leaf having a predetermined mass (e.g., 50 mg). In this embodiment, the ratios of RebD and RebM per unit mass of a dried leaf are not limited and may be, for example, (2.6% or more:0.4% or more), (2.8% or more:0.4% or more), (3% or more:0.4% or more), (3.2% or more:0.4% or more), (3.4% or more:0.4% or more), (3.6% or more:0.4% or more), (3.8% or more: 0.4% or more), (4% or more:0.4% or more), (4.2% or more:0.4% or more), (4.4% or more:0.4% or more), (4.6% or more:0.4% or more), (4.8% or more:0.4% or more), (5% or more:0.4% or more), (2.6% or more:0.5% or more), (2.8% or more:0.5% or more), (3% or more:0.5% or more), (3.2% or more:0.5% or more), (3.4% or more:0.5% or more), (3.6% or more:0.5% or more), (3.8% or more:0.5% or more), (4% or more:0.5% or more), (4.2% or more:0.5% or more), (4.4% or more:0.5% or more), (4.6% or more: 0.5% or more), (4.8% or more:0.5% or more), (5% or more:0.5% or more), (2.6% or more:0.6% or more), (2.8% or more:0.6% or more), (3% or more:0.6% or more), (3.2% or more:0.6% or more), (3.4% or more:0.6% or more), (3.6% or more:0.6% or more), (3.8% or more:0.6% or more), (4% or more:0.6% or more), (4.2% or more:0.6% or more), (4.4% or more:0.6% or more), (4.6% or more:0.6% or more), (4.8% or more:0.6% or more), (5% or more:0.6% or more), (2.6% or more:0.7% or more), (2.8% or more: 0.7% or more), (3% or more:0.7% or more), (3.2% or more:0.7% or more), (3.4% or more:0.7% or more), (3.6% or more:0.7% or more), (3.8% or more:0.7% or more), (4% or more:0.7% or more), (4.2% or more:0.7% or more), (4.4% or more:0.7% or more), (4.6% or more:0.7% or more), (4.8% or more:0.7% or more), (5% or more:0.7% or more), (2.6% or more:0.8% or more), (2.8% or more:0.8% or more), (3% or more:0.8% or more), (3.2% or more:0.8% or more), (3.4% or more:0.8% or more), (3.6% or more: 0.8% or more), (3.8% or more:0.8% or more), (4% or more:0.8% or more), (4.2% or more:0.8% or more), (4.4% or more:0.8% or more), (4.6% or more:0.8% or more), (4.8% or more:0.8% or more), (5% or more:0.8% or more) or the like in terms of (ratio of RebD:ratio of RebM), and are preferably (3.6% or more:0.4% or more). The upper limit of the ratio of RebD per unit mass of a dried leaf is not particularly limited and may be, for example, 20%, 15% or 10%. Likewise, the upper limit of the ratio of RebM is not particularly limited and may be, for example, 10%, 5% or 3%. As shown in Examples, the genetic features A to D are highly related to this embodiment.

In one embodiment, the plant of the present invention comprises 3.7% or more in total of RebD and RebM per unit mass of a dried leaf. This means that, for example, the total mass of RebD and RebM contained in a dried leaf having a predetermined mass (e.g., 50 mg) is 3.7% by mass or more (e.g., 1.85 mg or more). In this embodiment, the total ratio of RebD and RebM per unit mass of a dried leaf is not limited and may be, for example, 3.7% or more, 3.8% or more, 3.9% or more, 4.0% or more, 4.1% or more, 4.2% or more, 4.3% or more, 4.4% or more, 4.5% or more, 4.6% or more, 4.7% or more, 4.8% or more, 4.9% or more, 5.0% or more, 5.1% or more, 5.2% or more, 5.3% or more, 5.4% or more, 5.5% or more, 5.6% or more, 5.7% or more, 5.8% or more, 5.9% or more, 6.0% or more, 6.1% or more, 6.2% or more, 6.3% or more, 6.4% or more, 6.5% or more, 6.6% or more, 6.7% or more, 6.8% or more, 6.9% or more, 7.0% or more or the like, and is preferably 4.9% or more. The upper limit of the total ratio of RebD and RebM per unit mass of a dried leaf is not particularly limited and may be, for example, 25%, 20% or 15%. As shown in Examples, the genetic features A to D are highly related to this embodiment.

In one embodiment, in the plant of the present invention, the total mass ratio of RebD and RebM to total steviol glycoside is 37.8% or more. This means that, for example, when the total mass of RebD and RebM contained in a leaf (e.g., a dried leaf or a fresh leaf) is indicated by RebD+RebM/TSG % as the ratio to the total mass of steviol glycosides obtained from the leaf, the value of RebD+RebM/TSG is 37.8% or more. In this embodiment, the value of RebD+RebM/TSG is not limited and may be, for example, 37.8% or more, 37.9% or more, 38.0% or more, 38.1% or more, 38.2% or more, 38.3% or more, 38.4% or more, 38.5% or more, 38.6% or more, 38.7% or more, 38.8% or more, 38.9% or more, 39.0% or more, 39.2% or more, 39.4% or more, 39.6% or more, 39.8% or more, 40.0% or more, 40.2% or more, 40.4% or more, 40.6% or more, 40.8% or more, 41.0% or more, 41.2% or more, 41.4% or more, 41.6% or more, 41.8% or more, 42.0% or more, 42.4% or more, 42.8% or more, 43.2% or more, 43.6% or more, 44.0% or more, 44.4% or more, 44.8% or more, 45.2% or more, 45.6% or more, 46.0% or more or the like, and is preferably 38.1% or more. The upper limit of the mass ratio of RebD+RebM to total steviol glycoside is not particularly limited and may be, for example, 85%, 75%, 65% or 55%. As shown in Examples, the genetic features A to D are highly related to this embodiment.

TSG is a generic name for measurable steviol glycosides and includes neither an unknown steviol glycoside nor a steviol glycoside present at a level less than the detection limit. Preferably, the total steviol glycoside is any combination of two or more members selected from the group consisting of RebA, RebB, RebD, RebE, RebF, RebI, RebJ, RebK, RebM, RebN, RebO, RebQ, RebR, dulcoside A, rubusoside, steviolmonoside, steviolbioside and stevioside. In a certain embodiment, the total steviol glycoside may consist of, for example, RebA, RebB, RebM, RebD, RebF, RebM and stevioside. In another embodiment, the total steviol glycoside may consist of RebA, RebB, RebM, RebD, RebF, RebM, RebN, RebO and stevioside. In a specific embodiment, the total steviol glycoside consists of RebA, RebB, RebC, RebD, RebF, RebM, RebN and RebO.

In one embodiment, the plant of the present invention comprises 0.2% or more of RebM per unit mass of a dried leaf. This means that, for example, the mass of RebM contained in a dried leaf having a predetermined mass (e.g., 50 mg) is 0.2% by mass or more (e.g., 0.1 mg or more). In this embodiment, the total ratio of RebD and RebM per unit mass of a dried leaf is not limited and may be, for example, 0.20% or more, 0.25% or more, 0.30% or more, 0.35% or more, 0.40% or more, 0.45% or more, 0.50% or more, 0.55% or more, 0.60% or more, 0.65% or more, 0.70% or more, 0.75% or more, 0.80% or more, 0.85% or more, 0.90% or more, 0.95% or more, 1.00% or more, 1.05% or more, 1.10% or more, 1.15% or more, 1.20% or more, 1.25% or more, 1.30% or more, 1.35% or more, 1.40% or more, 1.45% or more or the like, and is preferably 0.4% or more. The upper limit of the ratio of RebM per unit mass of a dried leaf is not particularly limited and may be, for example, 15%, 10% or 5%. As shown in Examples, the genetic feature B is highly related to this embodiment.

In one embodiment, in the plant of the present invention, the mass ratio of RebM to total steviol glycoside is 2% or more. This means that, for example, when the mass of RebM contained in a leaf (e.g., a dried leaf or a fresh leaf) is indicated by RebM/TSG % as the ratio to the total mass of steviol glycosides obtained from the leaf, the value of RebM/TSG is 2% or more. In this embodiment, the value of RebM/TSG is not limited and may be, for example, 2% or more, 2.5% or more, 3% or more, 3.5% or more, 4% or more, 4.5% or more, 5% or more, 5.5% or more, 6% or more, 6.5% or more, 7% or more, 7.5% or more, 8% or more, 8.5% or more, 9% or more, 9.5% or more, 10% or more, 10.5% or more, 11% or more, 12% or more, 13% or more, 14% or more, 15% or more, 16% or more, 17% or more, 18% or more, 19% or more, 20% or more or the like, and is preferably 3.5% or more. The upper limit of the mass ratio of RebM to total steviol glycoside is not particularly limited and may be, for example, 50%, 45%, 40% or 35%. As shown in Examples, the genetic feature B is highly related to this embodiment.

In one embodiment, the plant of the present invention, when the amount (g) of rebaudioside M contained per 100 g of a leaf (e.g., a dried leaf or a fresh leaf) of the wild type *stevia* plant is defined as 100%, comprises rebaudioside M at higher content by 300% or more, 400% or more, 500% or more, 600% or more, 700% or more, 800% or more, 900% or more, 1100% or more, 1200% or more, 1300% or more, 1400% or more, 1500% or more, 1600% or more, 1700% or more, 1800% or more, 1900% or more, 2000% or more, 2100% or more, 2200% or more, 2300% or more, 2400% or more, 2500% or more, 2600% or more, 2700% or more, 2800% or more, 2900% or more, 3000% or more as compared with the wild type *stevia* species. As shown in Examples, the genetic feature B is highly related to this embodiment.

In one embodiment, the plant of the present invention comprises 1% or more of RebD per unit mass of a dried leaf. This means that, for example, the mass of RebD contained in a dried leaf having a predetermined mass (e.g., 50 mg) is 1% by mass or more (e.g., 0.5 mg or more). In this embodiment, the ratio of RebD per unit mass of a dried leaf is not limited and may be, for example, 1.00% or more, 1.05% or more, 1.10% or more, 1.15% or more, 1.20% or more, 1.25% or more, 1.30% or more, 1.35% or more, 1.40% or more, 1.45% or more, 1.50% or more, 1.55% or more, 1.60% or more, 1.65% or more, 1.70% or more, 1.75% or more, 1.80% or more, 1.85% or more, 1.90% or more, 1.95% or more, 2.00% or more, 2.05% or more, 2.10% or more, 2.15% or more, 2.20% or more, 2.25% or more, 2.30% or more, 2.35% or more, 2.40% or more, 2.45% or more, 2.50% or more, 2.55% or more, 2.60% or more, 2.65% or more, 2.70% or more, 2.75% or more, 2.80% or more, 2.85% or more, 2.90% or more, 2.95% or more, 3.00% or more, 3.05% or more, 3.10% or more, 3.15% or more, 3.20% or more, 3.25% or more, 3.30% or more, 3.35% or more, 3.40% or more, 3.45% or more, 3.50% or more, 3.55% or more, or 3.57% or more or the like, and is preferably 0.4% or more. The upper limit of the ratio of RebD per unit mass of a dried leaf is not particularly limited and may be, for example, 15%, 10% or 5%. As shown in Examples, the genetic feature B is highly related to this embodiment.

In one embodiment, in the plant of the present invention, when the content of RebM and RebD in a leaf (e.g., a dried leaf or a fresh leaf) is indicated by RebM/RebD ratio, the lower limit of the value of RebM/RebD is 0.2 or more, 0.3 or more, 0.4 or more, 0.5 or more, 0.6 or more, 0.8 or more, 1.0 or more.
On the other hand, the upper limit of the value of RebM/RebD is 0.3 or less, 0.4 or less, 0.5 or less, 0.6 or less, 0.8 or less, 1.0 or less, 1.1 or less, 1.2 or less. The combination of the lower limit and the upper limit is not particularly limited as long as the upper limit value is larger than the lower limit value in the combination. The ratio is preferably 0.2 or more and 1.2 or less, or 0.6 or more and 1.1 or less. As shown in Examples, the genetic feature B is highly related to this embodiment.

In one embodiment, in the plant of the present invention, when the content of RebM and RebD in a leaf (e.g., a dried leaf or a fresh leaf) is indicated by (RebD+RebM)/TSG % as the ratio to the total amount of steviol glycosides, the lower limit of the value of (RebD+RebM)/TSG is 14% or more, 16% or more, 18% or more, 20% or more, 22% or more, 24% or more, 26% or more, 28% or more, 30% or more, 32% or more, 34% or more, 36% or more, 38% or more. On the other hand, the upper limit of the value of (RebD+RebM)/TSG is 18% or less, 20% or less, 22% or less, 24% or less, 26% or less, 28% or less, 30% or less, 32% or less, 34% or less, 36% or less, 38% or less, 40% or less. The combination of the lower limit and the upper limit is not particularly limited as long as the upper limit value is larger than the lower limit value in the combination. The ratio is preferably 14% or more and 40% or less, or 16% or more and 40% or less. As shown in Examples, the genetic feature B is highly related to this embodiment.

RebD and RebM can be extracted in the state of a liquid extract by reacting a fresh leaf or a dried leaf of the plant of the present invention with a suitable solvent (an aqueous solvent such as water or an organic solvent such as an alcohol, ether or acetone). For the extraction conditions, etc., see a method described in Ohta et al., J. Appl. Glycosci., Vol. 57, No. 3, 199-209 (2010) or WO2010/038911, or a method described in Examples mentioned later.

RebD can be further purified from the liquid extract thus obtained by use of a method known in the art such as a gradient of ethyl acetate or any of other organic solvents: water, high performance liquid chromatography (HPLC), gas chromatography, time-of-flight mass spectrometry (TOF-MS), or ultra (high) performance liquid chromatography (UPLC).

The contents of RebD or RebM can be measured by a method described in Ohta et al. (supra) or WO2010/038911, or a method described in Examples mentioned later. Specifically, a fresh leaf can be sampled from the *stevia* plant of the present invention, followed by measurement by LC/MS-MS.

The plant of the present invention may include not only the whole plant but a plant organ (e.g., a leaf, a petal, a stem, a root, and a seed), a plant tissue (e.g., epidermis, phloem, soft tissue, xylem, vascular bundle, palisade tissue, and spongy tissue), various forms of plant cells (e.g., suspended cultured cells), a protoplast, a leaf section, a callus, and the like. The leaf may be the dried leaf mentioned above.

The plant of the present invention may also include a tissue culture or a cultured plant cell. This is because the plant can be regenerated by culturing such a tissue culture or a cultured plant cell. Examples of the tissue culture or the cultured plant cell of the plant of the present invention include, but are not limited to, embryos, meristem cells, pollens, leaves, roots, root apices, petals, protoplasts, leaf sections and calluses.

2. Method of Producing Plant of Present Invention

In an alternative aspect, the present invention provides a method of producing *stevia* plant having a lower ability to form flower buds than that of the wild type, the method comprising a step of crossing the *stevia* plant of the present invention with a second *stevia* plant (hereinafter, may be referred to as the "production method of the present invention").

The "*stevia* plant having a lower ability to form flower buds than that of the wild type" produced by the method has the same phenotype and genetic properties as those of the plant of the present invention.

The ability to form flower buds, the ranges of the contents of RebD and RebM, etc. in the plant obtained by the production method of the present invention are as described above about the plant of the present invention.

In one embodiment, the plant obtained by the production method of the present invention has the genetic feature X of the present invention. In one embodiment, the plant obtained by the production method of the present invention has the genetic feature A of the present invention. In another embodiment, the plant obtained by the production method of the present invention has the genetic feature B of the present invention. In an alternative embodiment, the plant obtained by the production method of the present invention has the genetic feature C or D of the present invention. In a preferable embodiment, the plant obtained by the production method of the present invention has the genetic feature X and the genetic feature A of the present invention. In another preferable embodiment, the plant obtained by the production method of the present invention has the genetic feature X and the genetic feature B of the present invention. In an alternative preferable embodiment, the plant obtained by the production method of the present invention has the genetic feature X and the genetic feature C or D of the present invention. In an alternative preferable embodiment, the plant obtained by the production method of the present invention has the genetic feature X, the genetic feature A, and the genetic feature B of the present invention. In an alternative preferable embodiment, the plant obtained by the production method of the present invention has the genetic feature X, the genetic feature A, and the genetic feature C or D of the present invention. In an alternative preferable embodiment, the plant obtained by the production method of the present invention has the genetic feature X, the genetic feature B, and the genetic feature C or D of the present invention. In a more preferable aspect, the plant obtained by the production method of the present invention has all of the genetic features X, A, B and C or D of the present invention.

In the production method of the present invention, "hybridizing" means that the plant of the present invention (first generation (S1)) is crossed with a second plant (S1) to obtain a progeny plant thereof (plant produced by the production method of the present invention (second generation (S2)). The hybridizing method is preferably backcross. The "backcross" is an approach of further crossing a progeny plant (S2) generated between the plant of the present invention and the second plant, with the plant of the present invention (i.e., a plant having the genetic feature(s) of the present invention) (S1) to produce a plant having the genetic feature(s) of the present invention. When the second plant (S1) for use in the production method of the present invention has the same phenotype and genetic properties as those of the plant of the present invention, the crossing is substantially backcross. The genetic polymorphism of the present invention is inheritable according to the Mendel's law. In association with this, the phenotype correlating with the genetic polymorphism, i.e., the low ability to form flower buds, is also inheritable according to the Mendel's law.

Alternatively, the plant of the present invention can also be produced by selfing. The selfing can be performed by the self-pollination of the stamen pollen of the plant of the present invention with the pistil of the plant of the present invention.

Since the plant produced by the production method of the present invention has the same phenotype and genetic properties as those of the plant of the present invention, the plant produced by the production method of the present invention can be further crossed with a third *stevia* plant to produce a *stevia* plant having a phenotype equivalent to that of the plant of the present invention.

In an alternative embodiment, the plant of the present invention may be produced by regenerating a plant by the culture of the tissue culture or the cultured plant cell mentioned above. The culture conditions are the same as those for culturing a tissue culture or a cultured plant cell of the wild type *stevia* plant and are known in the art (Protocols for In Vitro cultures and secondary metabolite analysis of aromatic and medicinal plants, Method in molecular biology, vo. 1391, pp 113-123).

In a further alternative embodiment, the plant of the present invention may be produced by introducing the variation of the present invention to the genome of a *stevia* plant. The introduction of the variation may be performed by a genetic modification approach or may be performed by a non-genetic modification approach. Examples of the "non-genetic modification approach" include a method of inducing a variation in the gene of a host cell (or a host plant) without transfection with a foreign gene. Examples of such a method include a method of allowing a mutagen to act on a plant cell. Examples of such a mutagen include ethylmethanesulfonic acid (EMS) and sodium azide. For example, the ethylmethanesulfonic acid (EMS) can be used at a concentration such as 0.1%, 0.2%, 0.3%, 0.4%, 0.5%, 0.6%, 0.7%, 0.8%, 0.9% or 1.0% to treat a plant cell. The treatment time is 1 to 48 hours, 2 to 36 hours, 3 to 30 hours, 4 to 28 hours, 5 to 26 hours, 6 to 24 hours. The procedures themselves of the treatment are known in the art and can be performed by dipping a water-absorbed seed obtained through a water absorption process in a treatment solution containing the mutagen at the concentration described above for the treatment time described above.

An alternative example of the non-genetic modification approach can be a method of irradiating a plant cell with radiation or light beam such as X ray, γ ray, or ultraviolet ray. In this case, a cell irradiated using an appropriate dose (ultraviolet lamp intensity, distance, and time) of ultraviolet ray is cultured in a selective medium or the like, and then, a cell, a callus, or a plant having the trait of interest can be selected. In this operation, the irradiation intensity is 0.01 to 100 Gr, 0.03 to 75 Gr, 0.05 to 50 Gr, 0.07 to 25 Gr, 0.09 to 20 Gr, 0.1 to 15 Gr, 0.1 to 10 Gr, 0.5 to 10 Gr, 1 to 10 Gr. The irradiation distance is 1 cm to 200 m, 5 cm to 100 m, 7 cm to 75 m, 9 cm to 50 m, 10 cm to 30 m, 10 cm to 20 m, 10 cm to 10 m. The irradiation time is 1 minute to 2 years, 2 minutes to 1 year, 3 minutes to 0.5 years, 4 minutes to 1 month, 5 minutes to 2 weeks, or 10 minutes to 1 week. The irradiation intensity, distance and time differ depending on the type of radiation or the state of the subject to be irradiated (cell, callus, or plant) and can be appropriately adjusted by those skilled in the art.

Approaches such as cell fusion, another culture (haploid induction), and remote crossing (haploid induction) are also known in the art.

In general, plant cells may involve a mutation during culture. Therefore, it is preferred to regenerate a plant individual, for more stably maintaining the trait.

The scope of the present invention does not exclude a plant obtained by the ex-post facto genetic recombination (e.g., genome editing) with the plant of the present invention as a host (e.g., a plant further provided with another trait by genetic recombination with the plant of the present invention as a host).

A plant having a plurality of different genetic features of the present invention may be produced by crossing plants differing from each other in the genetic feature of the present invention. For example, a plant having the genetic features X and A of the present invention can be obtained by crossing a plant having the genetic feature X of the present invention with a plant having the genetic feature A of the present invention. A plant having the genetic features X and B of the present invention, a plant having the genetic features X and C or D of the present invention, a plant having the genetic features A and B of the present invention, a plant having the genetic features A and C or D of the present invention, a plant having the genetic features B and C or D of the present invention, or the like can be obtained by similar crossing. Also, a plant having the genetic features X, A and B of the present invention can be obtained, for example, by crossing a plant having the genetic features X and A of the present invention with a plant having the genetic feature B of the present invention, by crossing a plant having the genetic features X and B of the present invention with a plant having the genetic feature A of the present invention, or by crossing a plant having the genetic feature X of the present invention with a plant having the genetic features A and B of the present invention. A plant having the genetic features X, B and C or D of the present invention, a plant having the genetic features A, B and C or D of the present invention, or the like can be obtained by similar crossing. The crossing is preferably performed over two or more generations. For heterozygous genetic features or the like, a plant having the desired combination of the genetic features may be obtained in one generation.

3. Method of Screening for Plant of Present Invention

The plant of the present invention or the plant having the same phenotype and genetic properties as those of the plant of the present invention can be screened for by detecting the genetic feature(s) of the present invention from a tissue of this plant. In this context, "screening" means that the plant of the present invention is discriminated from the other plants to select the plant of the present invention.

Thus, in an alternative aspect, the present invention provides a method of screening for a *stevia* plant having a low ability to form flower buds, comprising a step of detecting the presence and/or the absence of at least one of the genetic features X, A, B, C and D of the present invention from the genome of a test plant (hereinafter, may be referred to as the "screening method of the present invention").

In one embodiment, the genetic feature(s) to be detected is the genetic feature X of the present invention. In another embodiment, the genetic feature(s) to be detected is the genetic feature A of the present invention. In an alternative embodiment, the genetic feature(s) to be detected is the genetic feature B of the present invention. In an alternative embodiment, the genetic feature(s) to be detected is the genetic feature C of the present invention. In an alternative embodiment, the genetic feature(s) to be detected is the genetic feature D of the present invention. In a preferable embodiment, the genetic feature(s) to be detected is the genetic feature X and the genetic feature A of the present invention. In another preferable embodiment, the genetic feature(s) to be detected is the genetic feature X and the genetic feature B of the present invention. In an alternative preferable embodiment, the genetic feature(s) to be detected is the genetic feature X and the genetic feature C of the present invention. In an alternative preferable embodiment, the genetic feature(s) to be detected is the genetic feature X, the genetic feature A, and the genetic feature B of the present invention. In an alternative preferable embodiment, the genetic feature(s) to be detected is the genetic feature X, the genetic feature A, and the genetic feature C or D of the present invention. In an alternative preferable embodiment, the genetic feature(s) to be detected is the genetic feature X, the genetic feature B, and the genetic feature C or D of the present invention. In a more preferable embodiment, the genetic feature(s) to be detected is all of the genetic features X, A, B and C or D of the present invention.

The screening method of the present invention may further comprise a step of selecting from among the test plants a plant in which the presence of at least one genetic feature of the above is detected.

The presence of the genetic feature(s) of the present invention can be determined by detecting the presence of an allele selected from the group consisting of:

(X-1) an allele wherein the base at the position corresponding to position 90 of SEQ ID NO: 150 is G (e.g., an allele comprising the nucleotide sequence of SEQ ID NO: 153 or 154);

(X-2) an allele wherein the base at the position corresponding to position 108 of SEQ ID NO: 150 is G (e.g., an allele comprising the nucleotide sequence of SEQ ID NO: 155 or 156);

(A) an allele wherein the base at the position corresponding to position 201 of SEQ ID NO: 1 is A (e.g., an allele comprising the nucleotide sequence of SEQ ID NO: 69);

(B-1) an allele wherein the base at the position corresponding to position 40 of SEQ ID NO: 2 is T (e.g., an allele comprising the nucleotide sequence of SEQ ID NO: 70);

(B-2) an allele wherein the base at the position corresponding to position 44 of SEQ ID NO: 3 is T (e.g., an allele comprising the nucleotide sequence of SEQ ID NO: 71);

(B-3) an allele wherein the base at the position corresponding to position 41 of SEQ ID NO: 4 is C (e.g., an allele comprising the nucleotide sequence of SEQ ID NO: 72);

(B-4) an allele wherein the portion corresponding to positions 55-72 of SEQ ID NO: 5 is deleted (e.g., an allele comprising the nucleotide sequence of SEQ ID NO: 73); and (C) an allele wherein the base at the position corresponding to position 49 of SEQ ID NO: 6 is A (e.g., an allele comprising the nucleotide sequence of SEQ ID NO: 74); and/or by detecting the absence of an allele selected from the group consisting of:

(x-1) an allele wherein the base at the position corresponding to position 90 of SEQ ID NO: 150 is A (e.g., an allele comprising the nucleotide sequence of SEQ ID NO: 168 or 169);

(x-2) an allele wherein the base at the position corresponding to position 108 of SEQ ID NO: 150 is T (e.g., an allele comprising the nucleotide sequence of SEQ ID NO: 170 or 171);

(a) an allele wherein the base at the position corresponding to position 201 of SEQ ID NO: 1 is T (e.g., an allele comprising the nucleotide sequence of SEQ ID NO: 1);

(b-1) an allele wherein the base at the position corresponding to position 44 of SEQ ID NO: 2 is A (e.g., an allele comprising the nucleotide sequence of SEQ ID NO: 2);

(b-2) an allele wherein the base at the position corresponding to position 40 of SEQ ID NO: 3 is C (e.g., an allele comprising the nucleotide sequence of SEQ ID NO: 3);

(b-3) an allele wherein the base at the position corresponding to position 41 of SEQ ID NO: 4 is G (e.g., an allele comprising the nucleotide sequence of SEQ ID NO: 4);

(b-4) an allele wherein the portion corresponding to positions 55-72 of SEQ ID NO: 5 is not deleted (e.g., an allele comprising the nucleotide sequence of SEQ ID NO: 5); and (c) an allele wherein the base at the position corresponding to position 49 of SEQ ID NO: 6 is C (e.g., an allele comprising the nucleotide sequence of SEQ ID NO: 6).

The absence of the genetic feature(s) of the present invention can be determined by detecting the absence of an allele selected from the group consisting of:

(X-1) an allele wherein the base at the position corresponding to position 90 of SEQ ID NO: 150 is G (e.g., an allele comprising the nucleotide sequence of SEQ ID NO: 153 or 154);

(X-2) an allele wherein the base at the position corresponding to position 108 of SEQ ID NO: 150 is G (e.g., an allele comprising the nucleotide sequence of SEQ ID NO: 155 or 156);

(A) an allele wherein the base at the position corresponding to position 201 of SEQ ID NO: 1 is A (e.g., an allele comprising the nucleotide sequence of SEQ ID NO: 69);

(B-1) an allele wherein the base at the position corresponding to position 40 of SEQ ID NO: 2 is T (e.g., an allele comprising the nucleotide sequence of SEQ ID NO: 70);

(B-2) an allele wherein the base at the position corresponding to position 44 of SEQ ID NO: 3 is T (e.g., an allele comprising the nucleotide sequence of SEQ ID NO: 71);

(B-3) an allele wherein the base at the position corresponding to position 41 of SEQ ID NO: 4 is C (e.g., an allele comprising the nucleotide sequence of SEQ ID NO: 72);

(B-4) an allele wherein the portion corresponding to positions 55-72 of SEQ ID NO: 5 is deleted (e.g., an allele comprising the nucleotide sequence of SEQ ID NO: 73); and (C) an allele wherein the base at the position corresponding to position 49 of SEQ ID NO: 6 is A (e.g., an allele comprising the nucleotide sequence of SEQ ID NO: 74); and/or by detecting the presence of an allele selected from the group consisting of:

(x-1) an allele wherein the base at the position corresponding to position 90 of SEQ ID NO: 150 is A (e.g., an allele comprising the nucleotide sequence of SEQ ID NO: 168 or 169);

(x-2) an allele wherein the base at the position corresponding to position 108 of SEQ ID NO: 150 is T (e.g., an allele comprising the nucleotide sequence of SEQ ID NO: 170 or 171);

(a) an allele wherein the base at the position corresponding to position 201 of SEQ ID NO: 1 is T (e.g., an allele comprising the nucleotide sequence of SEQ ID NO: 1);

(b-1) an allele wherein the base at the position corresponding to position 44 of SEQ ID NO: 2 is A (e.g., an allele comprising the nucleotide sequence of SEQ ID NO: 2);

(b-2) an allele wherein the base at the position corresponding to position 40 of SEQ ID NO: 3 is C (e.g., an allele comprising the nucleotide sequence of SEQ ID NO: 3);

(b-3) an allele wherein the base at the position corresponding to position 41 of SEQ ID NO: 4 is G (e.g., an allele comprising the nucleotide sequence of SEQ ID NO: 4);

(b-4) an allele wherein the portion corresponding to positions 55-72 of SEQ ID NO: 5 is not deleted (e.g., an allele comprising the nucleotide sequence of SEQ ID NO: 5); and (c) an allele wherein the base at the position corresponding to position 49 of SEQ ID NO: 6 is C (e.g., an allele comprising the nucleotide sequence of SEQ ID NO: 6).

Specific examples of methods of detecting the genetic features of the present invention include, but not limited to, PCR method, TaqMan PCR method, sequencing method, microarray method, Invader method, TILLING method, RAD method, RFLP method, PCR-SSCP method, AFLP method, SSLP method, CAPS method, dCAPS method, ASO method, ARMS method, DGGE method, CCM method, DOL method, MALDI-TOF/MS method, TDI method, padlock probe method, molecular beacon method, DASH method, UCAN method, ECA method, PINPOINT method, PROBE method, VSET method, Survivor assay, Sniper assay, Luminex assay, GOOD method, LCx method, SNaPshot method, Mass ARRAY method, pyrosequencing method, SNP-IT method, melting curve analysis method, etc.

In the case of PCR method, it is preferable to generate a primer such that the 3' end portion has a sequence complementary to the polymorphic site of the present invention. By using a primer designed in this way, the polymerase extension reaction proceeds because the primer hybridizes completely to the template if the template sample has the polymorphism, whereas if the template does not have the variation of the present invention, the extension reaction does not occur because the nucleotide at the 3' end of the primer mismatches the template. Therefore, PCR amplification is performed using such a primer, and the amplification product is analyzed by agarose gel electrophoresis or the like, and if an amplification product of a predetermined size can be confirmed, the template as the sample has a variation, and if the amplification product is not present, it can be judged that the template does not have a variation.

Alternatively, the genetic feature(s) of the present invention can be detected by designing the primer sequence so that the polymorphism of the present invention and the primer sequence do not overlap and the genetic variation of the present invention can be PCR amplified, and by sequencing the nucleotide sequence of the amplified nucleotide fragment.

For PCR and agarose gel electrophoresis see Sambrook, Fritsch and Maniatis, "Molecular Cloning: A Laboratory Manual" 2nd Edition (1989), Cold Spring Harbor Laboratory Press.

TaqMan PCR method uses fluorescently labeled allele-specific oligos and Taq DNA polymerases (Livak, K. J. Genet). Anal. 14, 143 (1999); Morris T. et al., J. Clin. Microbiol. 34, 2933 (1996)).

The sequencing method is a method of analyzing the presence or absence of a variation by amplifying a region containing the variation by PCR and sequencing the DNA sequence using a Dye Terminator or the like (Sambrook, Fritsch and Maniatis (supra)).

A DNA microarray is one in which one end of a nucleotide probe is immobilized in an array on a support, and includes a DNA chip, a Gene chip, a microchip, a bead array, and the like. By using a probe containing a sequence complementary to the polymorphism of the present invention, the presence or absence of the polymorphism of the present invention can be comprehensively detected. DNA microarray assays such as DNA chips include GeneChip assays (see Affymetrix; U.S. Pat. Nos. 6,045,996; 5,925,525; and 5,858,659). The GeneChip technique utilizes a miniaturized, high density microarray of oligonucleotide probes affixed to a chip.

The invader method combines the hybridization of two reporter probes specific for each allele of a polymorphism such as SNPs and one invader probe to template DNA and the cleavage of DNA by Cleavase enzyme with a special endonuclease activity which cleaves a DNA by recognizing its structure (see, e.g., Livak, K. J. Biomol. Eng. 14, 143-149 (1999); Morris T. et al., J. Clin. Microbiol. 34, 2933 (1996); Lyamichev, V. et al., Science, 260, 778-783 (1993)).

TILLING (Targeting Induced Local Lesions IN Genomes) method is a method in which mutational mismatches in the genomes of a mutagenized mutant population are screened by PCR-amplification and CEL I nuclease-treatment.

In one embodiment, the genetic feature X-1 of the present invention can be detected, without limitations, by dCAPS method using the following primer set and a restriction enzyme.

Primer set:

A primer set comprising a forward primer comprising a sequence (e.g., SEQ ID NO: 157) of any consecutive 15 bases or more which is positioned upstream of position 90 of SEQ ID NO: 150, and a reverse primer comprising a sequence of any consecutive 15 to 25 bases long from the 3' end of a sequence selected from SEQ ID NOs: 158 and 172 to 183. The sequences of the primers can be optimized within a range that satisfies the conditions described above. For the optimization of primer design, see, for example, Sambrook and Russell, "Molecular Cloning: A Laboratory Manual" 3rd Edition (2001), Cold Spring Harbor Laboratory Press. Each of the primers may be 15 to 50 base long, 18 to 48 base long, 20 to 45 base long, 30 to 65 base long, or the like.

Restriction enzyme:

A restriction enzyme appropriate for each of SEQ ID NOs: 158 and 172 to 183 is shown below.

TABLE 1

Restriction enzyme appropriate for sequence contained in reverse primer

| Sequence contained in reverse primer | Restriction enzyme |
|---|---|
| TGGCGCCCCCCTGGGGCGTACACAG (SEQ ID NO: 158) | AluI |
| TGGCGCCCCCCTGGGGCGTACACGG (SEQ ID NO: 172) | BcefI |
| TGGCGCCCCCCTGGGGCGTACAGCG (SEQ ID NO: 173) | Eco47III/HaeII |
| TGGCGCCCCCCTGGGGCGTACGCCG (SEQ ID NO: 174) | TauI |
| TGGCGCCCCCCTGGGGCGTACAGCT (SEQ ID NO: 175) | AceIII |
| TGGCGCCCCCCTGGGGCATACACTG (SEQ ID NO: 176) | ApaBI |
| TGGCGCCCCCCTGGGGCGTACGCAG (SEQ ID NO: 177) | BbvI |
| TGGCGCCCCCCTGGGGCCTACACGG (SEQ ID NO: 178) | BglI |
| TGGCGCCCCCCTGGGAGTACACCT (SEQ ID NO: 179) | BplI/Hin4I |
| TGGCGCCCCCCTGGGGCGTACAACA (SEQ ID NO: 180) | BsbI |
| TGGCGCCCCCCTGGGGCGTACACGT (SEQ ID NO: 181) | BtrI |
| TGGCGCCCCCCTGGGGCGTACGACG (SEQ ID NO: 182) | HgaI |
| TGGCGCCCCCCTGGGGCGTACAAAG (SEQ ID NO: 183) | HindIII |

In a specific embodiment, the genetic feature X-1 of the present invention can be detected by dCAPS method using the following primer set and restriction enzyme.

TABLE 2

Combination of primer set and restriction enzyme

| Sequence of forward primer | Sequence of reverse primer | Restriction enzyme |
|---|---|---|
| SEQ ID NO: 157 | SEQ ID NO: 158 | AluI |
| SEQ ID NO: 157 | SEQ ID NO: 172 | BcefI |
| SEQ ID NO: 157 | SEQ ID NO: 173 | Eco47III/HaeII |
| SEQ ID NO: 157 | SEQ ID NO: 174 | TauI |
| SEQ ID NO: 157 | SEQ ID NO: 175 | AceIII |
| SEQ ID NO: 157 | SEQ ID NO: 176 | ApaBI |
| SEQ ID NO: 157 | SEQ ID NO: 177 | BbvI |
| SEQ ID NO: 157 | SEQ ID NO: 178 | BglI |
| SEQ ID NO: 157 | SEQ ID NO: 179 | BplI/Hin4I |
| SEQ ID NO: 157 | SEQ ID NO: 180 | BsbI |
| SEQ ID NO: 157 | SEQ ID NO: 181 | BtrI |
| SEQ ID NO: 157 | SEQ ID NO: 182 | HgaI |
| SEQ ID NO: 157 | SEQ ID NO: 183 | HindIII |

In one embodiment, the genetic feature X-2 of the present invention can be detected, without limitations, by dCAPS method using the following primer set and restriction enzyme.

Primer set:

A primer set comprising a forward primer comprising a sequence (e.g., SEQ ID NO: 157) of any consecutive 15 bases or more which is positioned upstream of position 108 of SEQ ID NO: 150, and a reverse primer comprising a sequence of any consecutive 15 to 29 bases long from the 3' end of a sequence selected from SEQ ID NOs: 163 and 184 to 191. The sequences of the primers can be optimized within a range that satisfies the conditions described above. For the optimization of primer design, see, for example, Sambrook and Russell (supra). Each of the primers may be 15 to 50 base long, 18 to 48 base long, 20 to 45 base long, 30 to 65 base long, or the like.

Restriction enzyme:

A restriction enzyme appropriate for each of SEQ ID NOs: 163 and 184 to 191 is shown below.

TABLE 3

Restriction enzyme appropriate for sequence contained in reverse primer

| Sequence contained in reverse primer | Restriction enzyme |
|---|---|
| AAAGTCTCTTGTGTTGAAATTCTGGGGCC (SEQ ID NO: 163) | ApaI/BmgI/HgiJII |
| AAAGTCTCTTGTGTTGAAATTCTGGCGCG (SEQ ID NO: 184) | AscI/BglI/BsePI |
| AAAGTCTCTTGTGTTGAAATTCTGGGGCC (SEQ ID NO: 185) | AsuI/DraII |
| AAAGTCTCTTGTGTTGAAATTCTGGCGGC (SEQ ID NO: 186) | CviJI |
| AAAGTCTCTTGTGTTGAAATTCTGGGGCG (SEQ ID NO: 187) | AcyI |
| AAAGTCTCTTGTGTTGAAATTCTGCCGCT (SEQ ID NO: 188) | BsrBI |
| AAAGTCTCTTGTGTTGAAATTCTGGTGCA (SEQ ID NO: 189) | MjaIV |

TABLE 3-continued

Restriction enzyme appropriate for sequence contained in reverse primer

| Sequence contained in reverse primer | Restriction enzyme |
|---|---|
| AAAGTCTCTTGTGTTGAAATTCTGGAGCT (SEQ ID NO: 190) | SacI |
| AAAGTCTCTTGTGTTGAAATTCTGGAGAC (SEQ ID NO: 191) | EcoPI |

In a specific embodiment, the genetic feature X-2 of the present invention can be detected by dCAPS method using the following primer set and restriction enzyme.

TABLE 4

Combination of primer set and restriction enzyme

| Sequence of forward primer | Sequence of reverse primer | Restriction enzyme |
|---|---|---|
| SEQ ID NO: 157 | SEQ ID NO: 163 | ApaI/BmgI/HgiJII |
| SEQ ID NO: 157 | SEQ ID NO: 184 | AscI/BglI/BsePI |
| SEQ ID NO: 157 | SEQ ID NO: 185 | AsuI/DraII |
| SEQ ID NO: 157 | SEQ ID NO: 186 | CviJI |
| SEQ ID NO: 157 | SEQ ID NO: 187 | AcyI |
| SEQ ID NO: 157 | SEQ ID NO: 188 | BsrBI |
| SEQ ID NO: 157 | SEQ ID NO: 189 | MjaIV |
| SEQ ID NO: 157 | SEQ ID NO: 190 | SacI |
| SEQ ID NO: 157 | SEQ ID NO: 191 | EcoPI |

In one embodiment, the genetic feature A of the present invention can be detected, without limitations, by CAPS method using a primer set that can amplify a region comprising a sequence shown in any of SEQ ID NOs: 19 to 21, and a restriction enzyme that cleaves the polynucleotides of SEQ ID NOs: 19 to 21 but does not cleave the polynucleotides of SEQ ID NOs: 75 to 77 or a restriction enzyme (e.g., Hpy188I) that does not cleave the polynucleotides of SEQ ID NOs: 19 to 21 but cleaves the polynucleotides of SEQ ID NOs: 75 to 77. Non-limiting examples of the primer set include the following.

Forward primer:
(SEQ ID NO: 37)
ATGGTTTGGGAATAGCTCTGTTGTT

Reverse primer:
(SEQ ID NO: 38)
AGAACTTTGTTCTTGAACCTCTTG

In one embodiment, the genetic feature B of the present invention can be detected, without limitations, by dCAPS method or the like using the following primer set and a restriction enzyme.

(B-1) a primer set comprising a forward primer comprising the nucleotide sequence shown in SEQ ID NO: 45 and a reverse primer comprising the nucleotide sequence shown in SEQ ID NO: 46;

(B-2) a primer set comprising a forward primer comprising the nucleotide sequence shown in SEQ ID NO: 50 and a reverse primer comprising the nucleotide sequence shown in SEQ ID NO: 51;

(B-3) a primer set comprising a forward primer comprising the nucleotide sequence shown in SEQ ID NO: 55 and a reverse primer comprising the nucleotide sequence shown in SEQ ID NO: 56; and (B-4) a primer set comprising a forward primer comprising the nucleotide sequence shown in SEQ ID NO: 60 and a reverse primer comprising the nucleotide sequence shown in SEQ ID NO: 61.

However, the primer set is not limited to those having the sequences of SEQ ID NOs: 45, 46, 50, 51, 55, 56, 60 or 61. For example, the forward primer can have in its 3' end a sequence from the 3' end of SEQ ID NO: 45, 50, 55 or 60 to 15 bases upstream thereof (see the table below), and the reverse primer can have in its 3' end a sequence from the 3' end of SEQ ID NO: 46, 51, 56 or 61 to 15 bases upstream thereof (see the table below). Such a primer may be 15 to 50 bases long or 20 to 45 bases long.

TABLE 5

Example of primer set

| Genetic feature (primer set name) | Forward primer (sequence from the 3' end to 15 bases upstream thereof) | Reverse primer (sequence from the 3' end to 15 bases upstream thereof) |
|---|---|---|
| B-1 (B-1') | 5'-CAAACAACCGGGTAC-3' (SEQ ID NO: 78) | 5'-AGACATTGGCAACTC-3' (SEQ ID NO: 79) |
| B-2 (B-2') | 5'-ATTTATTGTATCTAG-3' (SEQ ID NO: 80) | 5'-GTACACATGCTACAC-3' (SEQ ID NO: 81) |
| B-3 (B-3') | 5'-ACGAAACCCGCTTAA-3' (SEQ ID NO: 82) | 5'-TAATCCTTGAATTAG-3' (SEQ ID NO: 83) |
| B-4 (B-4') | 5'-ACACGTATACTAATC-3' (SEQ ID NO: 84) | 5'-CATGGTATGTACAAC-3' (SEQ ID NO: 85) |

The primer set is not limited to those having the sequences of SEQ ID NOs: 45, 46, 50, 51, 55, 56, 60 or 61. For example, the forward primer can have or comprise a sequence of any 15 or more consecutive bases in SEQ ID NO: 45, 50, 55 or 60, and the reverse primer can have or comprise a sequence of any 15 or more consecutive bases in SEQ ID NO: 46, 51, 56 or 61.

(B-1") A primer set comprising a forward primer having or comprising a sequence of any 15 or more consecutive bases in SEQ ID NO: 45 and a reverse primer having or comprising a sequence of any 15 or more consecutive bases in SEQ ID NO: 46;

(B-2") a primer set comprising a forward primer having or comprising a sequence of any 15 or more consecutive bases in SEQ ID NO: 50 and a reverse primer having or comprising a sequence of any 15 or more consecutive bases in SEQ ID NO: 51;

(B-3") a primer set comprising a forward primer having or comprising a sequence of any 15 or more consecutive bases in SEQ ID NO: 55 and a reverse primer having or comprising a sequence of any 15 or more consecutive bases in SEQ ID NO: 56; or (B-4") a primer set comprising a forward primer having or comprising a sequence of any 15 or more consecutive bases in SEQ ID NO: 60 and a reverse primer having or comprising a sequence of any 15 or more consecutive bases in SEQ ID NO: 61.

Such a primer may be 15 to 50 bases long, 20 to 45 bases long, or 30 to 65 bases long as long as the arbitrary sequence of 15 or more consecutive bases is present at the 3' end.

Examples of the restriction enzymes to be combined with the above primers include the following.

TABLE 6

Restriction enzymes to be combined with primers

| Primer | Restriction enzyme |
| --- | --- |
| (B-1), (B-1'), (B-1") | KpnI |
| (B-2), (B-2'), (B-2") | XbaI |
| (B-3), (B-3'), (B-3") | AflII |

In one embodiment, the genetic feature C or D of the present invention can be detected by dCAPS method using the following primer set and a restriction enzyme.

Primer set:

A primer set comprising a forward primer comprising a sequence which is positioned at the 3' end and selected from SEQ ID NOs: 86 to 109, and an optional sequence which is added to the 5' end of the sequence and is of any consecutive upstream bases following position 28 of SEQ ID NO: 6 (e.g., a consecutive sequence of any length), and a reverse primer comprising a sequence (e.g., SEQ ID NO: 65 or 110) complementary to a sequence of any consecutive 20 bases or more which is positioned downstream of position 50 of SEQ ID NO: 6. The sequences of the primers can be optimized within a range that satisfies the conditions described above. For the optimization of primer design, see, for example, Sambrook and Russell (supra). Each of the primers may be 15 to 50 base long, 18 to 48 base long, 20 to 45 base long, 30 to 65 base long, or the like.

Restriction enzyme:

A restriction enzyme appropriate for each of SEQ ID NOs: 86 to 109 is shown below. In the sequences described below, "R" represents A or G, and "Y" represents C or T.

TABLE 7

Restriction enzyme appropriate for sequence contained in forward primer

| Sequence contained in forward primer | Restriction enzyme |
| --- | --- |
| TTCAGGTAATAAAAGGCCTT (SEQ ID NO: 86) | DdeI |

TABLE 7-continued

Restriction enzyme appropriate for sequence contained in forward primer

| Sequence contained in forward primer | Restriction enzyme |
| --- | --- |
| TTCAGGTAATAAAAGGCACT (SEQ ID NO: 87) | MaeI/SpeI |
| TTCAGGTAATAAAAGGCTTA (SEQ ID NO: 88) | AflII/MseI |
| TTCAGGTAATAAAAGGCTTG (SEQ ID NO: 89) | Bce83I |
| TTCAGGTAATAAAAGGCCTC (SEQ ID NO: 90) | BseMII |
| TTCAGGTAATAAAAGGCACG (SEQ ID NO: 91) | BsiI |
| TTCAGGTAATAAAAGTCATG (SEQ ID NO: 92) | BspHI/Hpy178III |
| TTCAGGTAATAAAAGGCTRT (SEQ ID NO: 93) | SfeI |
| TTCAGGTAATAAAAGGCTTR (SEQ ID NO: 94) | SmlI |
| TTCAGGTAATAAAAGGCAGC (SEQ ID NO: 95) | EcoP15I |
| TTCAGGTAATAAAAGGCYCG (SEQ ID NO: 96) | AvaI |
| TTCAGGTAATAAAAGTGATC (SEQ ID NO: 97) | BclI |
| TTCAGGTAATAAAAGGGAGG (SEQ ID NO: 98) | BseRI |
| TTCAGGTAATAAAAGGCTGC (SEQ ID NO: 99) | CviRI/PstI |
| TTCAGGTAATAAAAGGAACC (SEQ ID NO: 100) | DrdII |
| TTCAGGTAATAAAAGGCTGA (SEQ ID NO: 101) | Eco57I |
| TTCAGGTAATAAAAGGCTGG (SEQ ID NO: 102) | GsuI |
| TTCAGGTAATAAAAGGGGTG (SEQ ID NO: 103) | HphI |
| TTCAGGTAATAAAAGGTCTG (SEQ ID NO: 104) | Hpy188I |
| TTCAGGTAATAAAAGGGAAG (SEQ ID NO: 105) | MboII |
| TTCAGGTAATAAAAGGTCGT (SEQ ID NO: 106) | Pfl1108I |
| TTCAGGTAATAAAAGTTATA (SEQ ID NO: 107) | PsiI |
| TTCAGGTAATAAAAGGCTCG (SEQ ID NO: 108) | TaqI/XhoI |
| TTCAGGCGATAAAAGGCGTT (SEQ ID NO: 109) | StySKI |
| TTCAGGTAATAAAAGGCATT (SEQ ID NO: 192) | SpeI |

In a specific embodiment, the genetic feature C or D of the present invention can be detected by dCAPS method using the following primer set and restriction enzyme.

TABLE 8

Combination of primer set and restriction enzyme

| Sequence of forward primer | Sequence of reverse primer | Restriction enzyme |
|---|---|---|
| SEQ ID NO: 64 | SEQ ID NO: 65 | SpeI |
| SEQ ID NO: 111 | SEQ ID NO: 65 | DdeI |
| SEQ ID NO: 112 | SEQ ID NO: 65 | MaeI/SpeI |
| SEQ ID NO: 113 | SEQ ID NO: 65 | AflII/MseI |
| SEQ ID NO: 114 | SEQ ID NO: 65 | Bce83I |
| SEQ ID NO: 115 | SEQ ID NO: 65 | BseMII |
| SEQ ID NO: 116 | SEQ ID NO: 65 | BsiI |
| SEQ ID NO: 117 | SEQ ID NO: 65 | BspHI/Hpy178III |
| SEQ ID NO: 118 | SEQ ID NO: 65 | SfeI |
| SEQ ID NO: 119 | SEQ ID NO: 65 | SmlI |
| SEQ ID NO: 120 | SEQ ID NO: 65 | EcoP15I |
| SEQ ID NO: 121 | SEQ ID NO: 65 | AvaI |
| SEQ ID NO: 122 | SEQ ID NO: 65 | BclI |
| SEQ ID NO: 123 | SEQ ID NO: 65 | BseRI |
| SEQ ID NO: 124 | SEQ ID NO: 65 | CviRI/PstI |
| SEQ ID NO: 125 | SEQ ID NO: 65 | DrdII |
| SEQ ID NO: 126 | SEQ ID NO: 65 | Eco57I |
| SEQ ID NO: 127 | SEQ ID NO: 65 | GsuI |
| SEQ ID NO: 128 | SEQ ID NO: 65 | HphI |
| SEQ ID NO: 129 | SEQ ID NO: 65 | Hpy188I |
| SEQ ID NO: 130 | SEQ ID NO: 65 | MboII |
| SEQ ID NO: 131 | SEQ ID NO: 65 | Pfl1108I |
| SEQ ID NO: 132 | SEQ ID NO: 65 | PsiI |
| SEQ ID NO: 133 | SEQ ID NO: 65 | TaqI/XhoI |
| SEQ ID NO: 134 | SEQ ID NO: 65 | StySKI |

The screening methods of the present invention may further comprise a step of evaluating an ability to form flower buds in the test *stevia* plant tissue for which the genetic features of the present invention have been detected. The evaluation of the ability to form flower buds is as described in the section relating to the plant of the present invention. In this embodiment, the screening method of the present invention may be applied to daughter plants obtained by selecting individuals having a lower ability to form flower buds from among the test *stevia* plants in which the genetic feature(s) of the present invention is/are detected, and crossing the selected individuals with another *stevia* plants. Thus, the screening method of the present invention may comprise one or more of the following steps.

(i) Detecting the genetic feature(s) (e.g., the genetic feature X of the present invention) of the present invention from the genome of a test *stevia* plant;

(ii) evaluating the ability to form flower buds in the test *stevia* plant tissue in which the genetic feature(s) has/have been detected;

(iii) selecting an individual having a lower ability to form flower buds from among the test *stevia* plants in which the genetic feature(s) of the present invention has/have been detected;

(iv) crossing the selected individual having a lower ability to form flower buds with another *stevia* plant;

(v) detecting the genetic feature(s) (e.g., the genetic feature X of the present invention) of the present invention from the genome of daughter plants obtained by crossing;

(vi) evaluating the ability to form flower buds in the tissue of the daughter plants in which the genetic feature(s) has/have been detected; and (vii) selecting individuals having a lower ability to form flower buds from among the daughter plants in which the genetic features are detected.

Individuals having a low ability to form flower buds of choice may be, for example, up to 50%, up to 40%, up to 30%, up to 20%, up to 10%, up to 5%, up to 4%, up to 3%, up to 2%, or up to 1% of the test *stevia* plants in which the genetic feature(s) of the present invention has/have been detected, with respect to the low ability to form flower buds. Other *stevia* plants to be crossed may or may not contain the genetic feature(s) of the present invention. In the above embodiment, steps (iv) to (vii) can be repeated a plurality of times. In this way, *stevia* plants having a lower ability to form flower buds can be screened.

In the screening method of the present invention, the test *stevia* plant may be a natural plant or a non-transgenic plant. Non-transgenic plants are as described in the section relating to the plant of the present invention.

In the screening method of the present invention, the test *stevia* plant may include a *stevia* plant subjected to a mutagenesis treatment and a progeny plant thereof. The mutagenesis treatment is as described in the section relating to the plant of the present invention, and includes treatment with a mutagen, treatment with radiation or irradiation with light, and the like.

The present invention also provides the above-mentioned primer set, e.g., the primer set described in Table 2 above, the primer set described in Table 4 above, the primer set comprising the forward primer of SEQ ID NO: 37 and the reverse primer of SEQ ID NO: 38, any one or more primer set(s) selected from the group consisting of the primer sets (B-1) to (B-4), (B-1') to (B-4') and (B-1") to (B-4") above, and/or the primer set described in Table 8 above. The present invention further provides a primer set capable of amplifying a region having a nucleotide sequence selected from the group consisting of SEQ ID NOs: 150, 164, 1 to 6, 69 to 74 by PCR, for example, a forward primer comprising a nucleotide sequence of SEQ ID NO: 151, a primer set with a reverse primer comprising a nucleotide sequence of SEQ ID NO: 152, a forward primer comprising a nucleotide sequence of SEQ ID NO: 7, a primer set with a reverse primer comprising a nucleotide sequence of SEQ ID NO: 8, a forward primer comprising a nucleotide sequence of SEQ ID NO: 9, a primer set with a reverse primer comprising a nucleotide sequence of SEQ ID NO: 10, a forward primer comprising a nucleotide sequence of SEQ ID NO: 11, a primer set with a reverse primer comprising a nucleotide sequence of SEQ ID NO: 12, a forward primer comprising a nucleotide sequence of SEQ ID NO: 13, a primer set with a reverse primer comprising a nucleotide sequence of SEQ ID NO: 14, a forward primer comprising a nucleotide sequence of SEQ ID NO: 15, a primer set with a reverse primer comprising a nucleotide sequence of SEQ ID NO: 16, a forward primer comprising a nucleotide sequence of SEQ ID NO: 17, and a primer set with a reverse primer comprising a nucleotide sequence of SEQ ID NO: 18.

In addition, the present invention provides a probe capable of detecting the presence and/or absence of the genetic features of the present invention, which may be referred to as the "probe of the present invention" hereinafter. The probe of the present invention may have a structure suitable for various detection methods for the presence and/or absence of the genetic feature(s) of the present invention. For example, the probe of the present invention may comprise a nucleotide sequence complementary to a portion of a genome comprising a variation site of the present invention. Non-limiting examples of such probes include those comprising a nucleotide sequence selected from SEQ ID NOs: 153 to 156, 168 to 171, 19 to 36, 75 to 77, 135 to 149. Of these sequences, SEQ ID NOs: 153 to 156, 19 to 36 are specific for alleles comprising the variation of the present invention, and SEQ ID NOs: 168 to 171, 75 to 77, 135 to 149 are specific for alleles not containing the variation of the present invention. The presence of the genetic feature(s) of the present invention may be detected by detection of an allele comprising the variation(s) of the present invention and/or by non-detection of an allele not comprising the variation(s) of the present invention, and the absence of the genetic feature(s) of the invention by non-detection of an allele comprising the variation(s) of the present invention and/or by detection of an allele not comprising the variation(s) of the present invention. The probes of the present invention preferably have a label. Non-limiting examples of such labels include fluorescent labels, luminescent labels, radioactive labels, dyes, enzymes, quenchers, binding moieties with detectable labels, and the like. In a specific embodiment, the probe of the present invention has a nucleotide sequence complementary to the nucleotide sequence selected from SEQ ID NOs: 153 to 156, 168 to 171, 19 to 36, 75 to 77, 135 to 149 and a label.

The present invention further provides a kit, for example, a kit for screening, comprising a primer set comprising a forward primer comprising a sequence (e.g., SEQ ID NO: 157) of any consecutive 15 bases or more which is positioned upstream of position 90 of SEQ ID NO: 150, and a reverse primer comprising a sequence of any consecutive 15 to 25 bases long from the 3' end of a sequence selected from SEQ ID NOs: 158 and 172 to 183, for example, a primer set described in Table 2, and a restriction enzyme appropriate therefor.

The present invention further provides a kit, for example, a kit for screening, comprising a primer set comprising a forward primer comprising a sequence (e.g., SEQ ID NO: 157) of any consecutive 15 bases or more which is positioned upstream of position 108 of SEQ ID NO: 150, and a reverse primer comprising a sequence of any consecutive 15 to 25 bases long from the 3' end of a sequence selected from SEQ ID NOs: 163 and 184 to 191, for example, a primer set described in Table 4, and a restriction enzyme appropriate therefor.

The present invention further provides a kit, for example, a kit for screening, comprising a primer set that can amplify a region comprising a sequence shown in any of SEQ ID NOs: 19 to 21, for example, a primer set comprising the combination of a forward primer comprising the nucleotide sequence of SEQ ID NO: 7 and a reverse primer comprising the nucleotide sequence of SEQ ID NO: 8, and a restriction enzyme that cleaves the polynucleotides of SEQ ID NOs: 19 to 21 but does not cleave the polynucleotides of SEQ ID NOs: 75 to 77 or a restriction enzyme (e.g., Hpy188I) that does not cleave the polynucleotides of SEQ ID NOs: 19 to 21 but cleaves the polynucleotides of SEQ ID NOs: 75 to 77.

The present invention further provides a kit, for example, a kit for screening comprising any one or more primer set(s) selected from the group consisting of the primer sets (B-1) to (B-4), (B-1') to (B-4') and (B-1") to (B-4"), and optionally a restriction enzyme.

In the kit, the restriction enzyme contained in the kit is KpnI in the case of using any one or more primer set(s) selected from the group consisting of the primer sets (B-1), (B-1') and (B-1").

In the kit, the restriction enzyme contained in the kit is XbaI in the case of using any one or more primer set(s) selected from the group consisting of the primer sets (B-2), (B-2') and (B-2").

In the kit, the restriction enzyme contained in the kit is AflII in the case of using any one or more primer set(s) selected from the group consisting of the primer sets (B-3), (B-3') and (B-3").

The present invention further provides a kit, for example, a kit for screening, comprising a primer set comprising a forward primer comprising a sequence which is positioned at the 3' end and selected from SEQ ID NOs: 86 to 109 and 192, and an optional sequence which is added to the 5' end of the sequence and is of any consecutive upstream bases following position 28 of SEQ ID NO: 6 (e.g., a consecutive sequence of any length), and a reverse primer comprising a sequence (e.g., SEQ ID NO: 65 or 110) complementary to a sequence of any consecutive 20 bases or more which is positioned downstream of position 50 of SEQ ID NO: 6, for example, a primer set described in Table 8, and a restriction enzyme appropriate therefor.

In another embodiment of the kit:

in case the primer set comprises a forward primer having or comprising a sequence of any consecutive 15 bases or more in SEQ ID NO: 45, the restriction enzyme comprises KpnI;

in case the primer set comprises a forward primer having or comprising a sequence of any contiguous 15 bases or more in SEQ ID NO: 50, the restriction enzyme comprises XbaI; and in case the primer set comprises a forward primer having or comprising a sequence of any consecutive 15 bases or more in SEQ ID NO: 55, the restriction enzyme comprises AflII.

The present invention also provides a screening kit comprising a primer set capable of amplifying by PCR a region having a nucleotide sequence selected from the group consisting of SEQ ID NOs: 153 to 156, 168 to 171, 1 to 6, 19 to 36, 69 to 77, 135 to 149, and a probe of the present invention.

These primer sets, probes and kits can be used to detect the genetic feature(s) of the present invention, used in the screening methods of the present invention, and the like. These primer sets and kits may also comprise an instruction including an explanation on the detection of genetic feature(s) of the present invention and on the screening method of the present invention, e.g., a written instruction, and media, e.g., a flexible disk, a CD, a DVD, a Blu-ray disk, a memory card, a USB memory, etc., having recorded thereon information regarding the method of use.

4. Method of Producing Extract Derived from Plant and Product Comprising the Extract In a further aspect, the present invention provides a method of producing a *stevia* extract, comprising a step of obtaining an extract from the plant of the present invention, or a seed or a leaf (e.g., dried leaf or fresh leaf) of the plant (hereinafter, may be referred to as the "extract production method of the present invention"). The present invention further provides a method of producing a steviol glycoside purified product, comprising a step of purifying a steviol glycoside from an extract obtained by the extract production method of the present invention (hereinafter, may be referred to as the "steviol glycoside purified product production method of the present invention").

Specifically, the present invention provides a method of producing a steviol glycoside purified product, comprising a step of obtaining an extract containing a steviol glycoside from the *stevia* plant of the present invention, the *stevia* plant screened for by the screening method of the present invention, or the *stevia* plant produced by the method of the present invention, and a step of purifying a steviol glycoside from the obtained extract.

The extract containing a steviol glycoside can be obtained by reacting a fresh leaf or a dried leaf of the plant of the present invention with a suitable solvent (an aqueous solvent such as water or an organic solvent such as an alcohol, ether or acetone). For the extraction conditions, etc., see a method described in Ohta et al. (supra) or WO2010/038911, or a method described in Examples mentioned later.

Individual steviol glycoside can be purified from the extract containing a steviol glycoside by use of a method known in the art such as a gradient of ethyl acetate or any of other organic solvents:water, high performance liquid chromatography (HPLC), gas chromatography, time-of-flight mass spectrometry (TOF-MS), or ultra (high) performance liquid chromatography (UPLC).

Examples of the steviol glycoside include RebA, RebB, RebC, RebD, RebE, RebF, RebI, RebJ, RebK, RebM, RebN, RebO, RebQ, RebR, dulcoside A, rubusoside, steviolmonoside, steviolbioside, and stevioside. In one embodiment, the steviol glycoside includes RebA, RebB, RebC, RebD, RebE, RebF, RebM, RebN, RebO, stevioside, steviolbioside, rubusoside, dulcoside A or a combination thereof. In a preferable embodiment, the steviol glycoside includes RebD, RebM or a combination thereof.

One form of the extract obtained by the extract production method of the present invention (hereinafter, may be referred to as the "extract of the present invention") comprises RebD or RebM, or both at higher content as compared with the wild type *stevia* species.

The extract of the present invention may comprise RebD or RebM, or both at a content higher by 300% or more, 400% or more, 500% or more, 600% or more, 700% or more, 800% or more, 900% or more, 1100% or more, 1200% or more, 1300% or more, 1400% or more, 1500% or more, 1600% or more, 1700% or more, 1800% or more, 1900% or more, 2000% or more, 2100% or more, 2200% or more, 2300% or more, 2400% or more, 2500% or more, 2600% or more, 2700% or more, 2800% or more, 2900% or more, 3000% or more, 3100% or more, 3200% or more, 3300% or more, 3400% or more, 3500% or more, 3600% or more, 3700% or more, 3800% or more, 3900% or more, 4000% or more, 4100% or more, 4200% or more, 4300% or more, 4400% or more, 4500% or more, 4600% or more, 4700% or more, 4800% or more, 4900% or more, 5000% or more as compared with an extract obtained from the wild type *stevia* species. The extract of the present invention and the extract obtained from the wild type *stevia* species may be those obtained by the same process.

The extract of the present invention thus obtained and/or the steviol glycoside purified product (e.g., RebD and/or RebM) obtained by the method of producing a steviol glycoside purified product according to the present invention can be mixed with other component(s) to produce a medicament, flavor or food or beverage containing a steviol glycoside. Accordingly, in an alternative aspect, the present invention provides a method of producing a medicament, a flavor or a food or beverage, comprising a step of mixing the extract of the present invention and/or the steviol glycoside purified product obtained by the method of producing a steviol glycoside purified product according to the present invention with other component(s). The present invention further provides a medicament, flavor or food or beverage containing a steviol glycoside, obtained by the production method. In this context, the food or beverage means a drink and a food. Thus, in a certain embodiment, the present invention provides a medicament, flavor, drink or food and also provides a method of producing the medicament, the flavor, the drink or the food.

5. Nucleotide Sequence Related to Plant of Present Invention

In another aspect, the present invention provides a nucleotide sequence related to the *stevia* plant of the present invention.

The nucleotide sequence related to a *stevia* plant having the genetic feature X-1 comprises or consists of a nucleotide sequence selected from SEQ ID NOs: 153 and 154. The nucleotide sequence related to a *stevia* plant having the genetic feature X-2 comprises or consists of a nucleotide sequence selected from SEQ ID NOs: 155 and 156. The nucleotide sequence related to a *stevia* plant having the genetic feature A comprises or consists of a nucleotide sequence selected from SEQ ID NOs: 19 to 21 and 69. The nucleotide sequence related to a *stevia* plant having the genetic feature B-1 comprises or consists of a nucleotide sequence selected from SEQ ID NOs: 22 to 24 and 70. The nucleotide sequence related to a *stevia* plant having the genetic feature B-2 comprises or consists of a nucleotide sequence selected from SEQ ID NOs: 25 to 27 and 71. The nucleotide sequence related to a *stevia* plant having the genetic feature B-3 comprises or consists of a nucleotide sequence selected from SEQ ID NOs: 28 to 30 and 72. The nucleotide sequence related to a *stevia* plant having the genetic feature B-4 comprises or consists of a nucleotide sequence selected from SEQ ID NOs: 31 to 33, 62 and 73. The nucleotide sequence related to a *stevia* plant having the genetic feature C or D comprises or consists of a nucleotide sequence selected from SEQ ID NOs: 34 to 36 and 74.

EXAMPLES

Hereinafter, the present invention will be described with reference to Experimental Examples, Examples, etc. However, the present invention is not limited by these specific embodiments.

[Example 1] Verification of Relationship Between RebM Content and Genetic Feature B-(1)

Individuals derived from commercially available *stevia* seeds were subjected to selection based on the development and growth condition, the foliar morphology, the contents of total steviol glycoside (TSG), RebA, RebD, and RebM, etc. to obtain two segregating populations, i.e., individual groups I and II. 62 individuals from the individual group I and 109 individuals from the individual group II were used in verification. Each individual group was divided on the basis of RebM content into 3 groups: 0.2% or more, 0.1% or more to less than 0.2%, and 0% or more to less than 0.1%, and examined for the presence or absence of the genetic feature B-1. Specifically, PCR was performed using the primers given below. A restriction enzyme (KpnI) was added to the PCR product, and enzymatic reaction was performed at 37° C. for treatment with the restriction enzyme. After the restriction enzyme treatment, electrophoresis was performed using a microchip type electrophoresis apparatus LabChip GX Touch HT. The marker was identified on the basis of a band pattern after the electrophoresis.

The primer sequences are as follows.

```
Fw primer:
                                        (SEQ ID NO: 45)
5'-TAATCATCCAAACCCTAATCTCGCCAAACAACCGGGTAC-3'

Rv primer:
                                        (SEQ ID NO: 46)
5'-GAGGAAGACATTGGCAACTC-3'
```

When a restriction enzyme-treated product of approximately 260 bp (e.g., SEQ ID NO: 49) was not formed by the KpnI restriction enzyme treatment of the obtained PCR product (approximately 297 bp long), the test subject was regarded as being positive for B-1. As a result, the group containing 0.2% or more or RebM was preferentially detected with the genetic feature of the present invention. These results demonstrated that the frequency of appearance of positive individuals was statistically significantly different among groups (goodness of fit test by the chi square test; the null hypothesis stated that the frequency distribution was even without the association of the marker test results with the phenotype; for the test results, see the tables below).

TABLE 9

Results of test on individual group I (62 individuals)

| RebM content (%) | Test results | | |
| --- | --- | --- | --- |
|  | Positive | Negative | Total |
| 0.2 or more | 29 | 8 | 37 |
| 0.1 or more and less than 0.2 | 0 | 20 | 20 |
| 0 or more and less than 0.1 | 0 | 5 | 5 |
| Total | 29 | 33 | 62 |

Chi square test result (df = 2) 36.81**

TABLE 10

Results of test on individual group II (109 individuals)

| RebM content (%) | Test results | | |
| --- | --- | --- | --- |
|  | Positive | Negative | Total |
| 0.2 or more | 18 | 1 | 19 |
| 0.1 or more and less than 0.2 | 35 | 3 | 38 |
| 0 or more and less than 0.1 | 5 | 47 | 52 |
| Total | 58 | 51 | 109 |

Chi square test result (df = 2) 75.94**

[Example 2] Verification of Relationship Between RebM Content and Genetic Feature B (2)

As a result of selecting a plant with high RebM content using the genetic feature B, individuals having a RebM ratio of 2% or more were also able to be selected in segregating populations other than the populations for verification, as shown in the table below, confirming that these genetic markers are capable of serving as practical selection markers. The results of selecting a plant with high RebM content are shown in the table below. In the table, the circle mark represents that the genetic feature B test results were positive.

The genetic feature B-1 was detected in the same way as in Example 1, and the genetic features B-2 to B-4 were detected as follows.

For the detection of the genetic feature B-2, PCR was performed using the primers given below. A restriction enzyme (XbaI) was added to the PCR product, and enzymatic reaction was performed at 37° C. for treatment with the restriction enzyme. After the restriction enzyme treatment, electrophoresis was performed using a microchip type electrophoresis apparatus LabChip GX Touch HT. The marker was identified on the basis of a band pattern after the electrophoresis.

The primer sequences are as follows.

```
Fw primer:
                                        (SEQ ID NO: 50)
5'-AAGGTTCTTTATTTTTAAACTTATGTTAATTTATTGTATCTAG-3'

Rv primer:
                                        (SEQ ID NO: 51)
5'-CCTTATGTACACATGCTACAC-3'
```

When a restriction enzyme-treated product of approximately 344 bp (e.g., SEQ ID NO: 54) was not formed by the XbaI restriction enzyme treatment of the obtained PCR product (approximately 383 bp long), the test subject was regarded as being positive for the genetic feature B-2.

For the detection of the genetic feature B-3, PCR was performed using the primers given below. A restriction enzyme (AflII) was added to the PCR product, and enzymatic reaction was performed at 37° C. for treatment with the restriction enzyme. After the restriction enzyme treatment, electrophoresis was performed using a microchip type electrophoresis apparatus LabChip GX Touch HT. The marker was identified on the basis of a band pattern after the electrophoresis.

The primer sequences are as follows.

```
Fw primer:
                                        (SEQ ID NO: 55)
5'-CGATGGTTTTTGCTACATGAAAACCCTAGAAGACGAAACCCGC
TTAA-3'

Rv primer:
                                        (SEQ ID NO: 56)
5'-ACCAGCAATAATCCTTGAATTAG-3'
```

When a restriction enzyme-treated product of approximately 347 bp (e.g., SEQ ID NO: 59) was not formed by the AflII restriction enzyme treatment of the obtained PCR product (approximately 390 bp long), the test subject was regarded as being positive for the genetic feature B-3.

For the detection of the genetic feature B-4, PCR was performed using the primers given below. The PCR product was electrophoresed using a microchip type electrophoresis apparatus LabChip GX Touch HT. The marker was identified on the basis of a band pattern after the electrophoresis.

The primer sequences are as follows.

```
    Fw primer:
                                        (SEQ ID NO: 60)
    5'-CGCAAACACGTATACTAATC-3'

Rv primer:
                                        (SEQ ID NO: 61)
    5'-TTTAGCATGGTATGTACAAC-3'
```

When only a PCR product of approximately 140 bp (e.g., SEQ ID NO: 62) was formed, the test subject was regarded as being positive for B-4.

TABLE 11

| | | RebA | | RebD | | RebM | |
|---|---|---|---|---|---|---|---|
| | TSG (%) | Content (%) | RA/TSG | Content (%) | RD/TSG | Content (%) | RM/TSG |
| S1 | 18.45 | 13.23 | 71.73% | 1.77 | 9.58% | 1.46 | 7.92% |
| S2 | 15.10 | 7.20 | 47.64% | 3.57 | 23.64% | 1.29 | 8.56% |
| S3 | 8.96 | 5.59 | 62.37% | 1.42 | 15.85% | 1.19 | 13.31% |
| S4 | 9.12 | 6.07 | 66.53% | 1.09 | 11.91% | 1.11 | 12.14% |
| S5 | 7.40 | 4.16 | 56.20% | 1.42 | 19.23% | 1.07 | 14.49% |
| S6 | 7.27 | 4.46 | 61.32% | 1.13 | 15.50% | 1.03 | 14.11% |
| S8 | 9.53 | 6.31 | 66.22% | 1.32 | 13.83% | 0.97 | 10.13% |
| S9 | 8.77 | 5.26 | 59.97% | 1.61 | 18.30% | 0.96 | 11.00% |
| S12 | 9.26 | 5.47 | 59.06% | 1.97 | 21.30% | 0.94 | 10.10% |
| S13 | 9.76 | 6.23 | 63.82% | 1.57 | 16.09% | 0.92 | 9.45% |
| S14 | 8.11 | 5.21 | 64.25% | 1.15 | 14.20% | 0.90 | 11.13% |
| S15 | 8.28 | 5.32 | 64.24% | 1.27 | 15.32% | 0.90 | 10.89% |
| S16 | 11.61 | 6.54 | 56.35% | 2.25 | 19.42% | 0.90 | 7.75% |
| S17 | 7.05 | 4.32 | 61.28% | 1.14 | 16.16% | 0.89 | 12.66% |
| S18 | 8.66 | 5.19 | 59.91% | 1.68 | 19.34% | 0.89 | 10.27% |
| S19 | 9.83 | 5.46 | 55.57% | 2.16 | 21.96% | 0.87 | 8.88% |
| S21 | 8.27 | 5.30 | 64.08% | 1.33 | 16.11% | 0.85 | 10.30% |
| S22 | 7.86 | 3.92 | 49.84% | 2.15 | 27.30% | 0.85 | 10.79% |
| S23 | 9.22 | 6.03 | 65.43% | 1.42 | 15.41% | 0.85 | 9.19% |
| S25 | 9.37 | 6.39 | 68.22% | 1.35 | 14.36% | 0.74 | 7.93% |
| S26 | 6.70 | 3.60 | 53.75% | 1.68 | 25.08% | 0.66 | 9.78% |
| S27 | 8.91 | 3.21 | 36.02% | 2.77 | 31.11% | 0.53 | 5.96% |
| S28 | 18.28 | 11.97 | 65.48% | 2.52 | 13.81% | 0.46 | 2.51% |
| S29 | 15.09 | 9.78 | 64.80% | 1.84 | 12.20% | 0.35 | 2.34% |
| S30 | 13.09 | 7.83 | 59.84% | 2.16 | 16.49% | 0.31 | 2.36% |
| S31 | 13.66 | 9.24 | 67.64% | 1.66 | 12.18% | 0.30 | 2.21% |
| S32 | 14.04 | 8.61 | 61.33% | 2.32 | 16.50% | 0.30 | 2.12% |
| S33 | 12.66 | 7.89 | 62.34% | 1.58 | 12.49% | 0.29 | 2.25% |
| S34 | 12.68 | 7.86 | 61.98% | 1.82 | 14.31% | 0.29 | 2.25% |
| S35 | 10.48 | 6.28 | 59.95% | 1.68 | 16.06% | 0.27 | 2.57% |
| S36 | 5.50 | 1.94 | 35.25% | 1.61 | 29.18% | 0.24 | 4.39% |
| S37 | 6.93 | 2.06 | 29.74% | 1.66 | 23.99% | 0.21 | 3.02% |
| S38 | 7.97 | 2.65 | 33.26% | 1.72 | 21.59% | 0.19 | 2.37% |
| S39 | 11.68 | 7.57 | 64.83% | 0.10 | 0.85% | 0.04 | 0.33% |
| S40 | 13.20 | 8.94 | 67.72% | 0.09 | 0.71% | 0.04 | 0.27% |
| S41 | 11.57 | 6.90 | 59.66% | 0.11 | 0.91% | 0.03 | 0.26% |
| S42 | 10.43 | 6.04 | 57.89% | 0.11 | 1.03% | 0.03 | 0.25% |
| S43 | 11.30 | 3.48 | 30.82% | 0.08 | 0.69% | 0.01 | 0.06% |

| | RebA + RebM | | RebD + RebM | | | | | | | |
|---|---|---|---|---|---|---|---|---|---|---|
| | Content (%) | RAM/TSG | Content (%) | RDM/TSG | RebM/ RebA | RebM/ RebD | B-1 | B-2 | B-3 | B-4 |
| S1 | 14.69 | 79.65% | 3.23 | 17.51% | 0.11 | 0.83 | ○ | ○ | ○ | ○ |
| S2 | 8.49 | 56.20% | 4.86 | 32.19% | 0.18 | 0.36 | ○ | ○ | ○ | ○ |
| S3 | 6.78 | 75.68% | 2.61 | 29.16% | 0.21 | 0.84 | ○ | ○ | ○ | ○ |
| S4 | 7.18 | 78.67% | 2.19 | 24.05% | 0.18 | 1.02 | ○ | ○ | ○ | ○ |
| S5 | 5.23 | 70.69% | 2.50 | 33.73% | 0.26 | 0.75 | ○ | ○ | ○ | ○ |
| S6 | 5.49 | 75.43% | 2.15 | 29.61% | 0.23 | 0.91 | ○ | ○ | ○ | ○ |
| S8 | 7.28 | 76.36% | 2.28 | 23.96% | 0.15 | 0.73 | ○ | ○ | ○ | ○ |
| S9 | 6.22 | 70.97% | 2.57 | 29.30% | 0.18 | 0.60 | | | | |
| S12 | 6.41 | 69.16% | 2.91 | 31.40% | 0.17 | 0.47 | ○ | ○ | ○ | ○ |
| S13 | 7.15 | 73.27% | 2.49 | 25.54% | 0.15 | 0.59 | ○ | ○ | ○ | ○ |
| S14 | 6.11 | 75.38% | 2.05 | 25.33% | 0.17 | 0.78 | ○ | ○ | ○ | ○ |
| S15 | 6.22 | 75.13% | 2.17 | 26.21% | 0.17 | 0.71 | ○ | ○ | ○ | ○ |
| S16 | 7.44 | 64.10% | 3.15 | 27.17% | 0.14 | 0.40 | ○ | ○ | ○ | ○ |
| S17 | 5.21 | 73.94% | 2.03 | 28.82% | 0.21 | 0.78 | ○ | ○ | ○ | ○ |
| S18 | 6.08 | 70.18% | 2.57 | 29.61% | 0.17 | 0.53 | ○ | ○ | ○ | ○ |
| S19 | 6.33 | 64.44% | 3.03 | 30.84% | 0.16 | 0.40 | ○ | ○ | ○ | ○ |
| S21 | 6.15 | 74.38% | 2.18 | 26.41% | 0.16 | 0.64 | ○ | ○ | ○ | ○ |
| S22 | 4.77 | 60.63% | 2.99 | 38.09% | 0.22 | 0.40 | ○ | ○ | ○ | ○ |
| S23 | 6.88 | 74.62% | 2.27 | 24.61% | 0.14 | 0.60 | ○ | ○ | ○ | ○ |
| S25 | 7.13 | 76.15% | 2.09 | 22.30% | 0.12 | 0.55 | ○ | ○ | ○ | ○ |
| S26 | 4.26 | 63.54% | 2.33 | 34.86% | 0.18 | 0.39 | ○ | ○ | ○ | ○ |
| S27 | 3.74 | 41.98% | 3.30 | 37.07% | 0.17 | 0.19 | ○ | ○ | ○ | ○ |
| S28 | 12.43 | 67.99% | 2.98 | 16.33% | 0.04 | 0.18 | ○ | ○ | ○ | ○ |
| S29 | 10.13 | 67.15% | 2.20 | 14.55% | 0.04 | 0.19 | ○ | ○ | ○ | ○ |
| S30 | 8.14 | 62.20% | 2.47 | 18.85% | 0.04 | 0.14 | ○ | ○ | ○ | ○ |
| S31 | 9.54 | 69.85% | 1.97 | 14.39% | 0.03 | 0.18 | ○ | ○ | ○ | ○ |

TABLE 11-continued

| | | | | | | | | | | |
|---|---|---|---|---|---|---|---|---|---|---|
| S32 | 8.91 | 63.45% | 2.61 | 18.62% | 0.03 | 0.13 | ○ | ○ | ○ | ○ |
| S33 | 8.18 | 64.60% | 1.87 | 14.74% | 0.04 | 0.18 | ○ | ○ | ○ | ○ |
| S34 | 8.15 | 64.22% | 2.10 | 16.56% | 0.04 | 0.16 | ○ | ○ | ○ | ○ |
| S35 | 6.55 | 62.52% | 1.95 | 18.64% | 0.04 | 0.16 | ○ | ○ | ○ | ○ |
| S36 | 2.18 | 39.64% | 1.85 | 33.57% | 0.12 | 0.15 | ○ | ○ | ○ | ○ |
| S37 | 2.27 | 32.77% | 1.87 | 27.01% | 0.10 | 0.13 | ○ | ○ | ○ | ○ |
| S38 | 2.84 | 35.63% | 1.91 | 23.97% | 0.07 | 0.11 | ○ | ○ | ○ | ○ |
| S39 | 7.61 | 65.15% | 0.14 | 1.17% | 0.01 | 0.38 | | | | |
| S40 | 8.97 | 67.99% | 0.13 | 0.98% | 0.00 | 0.38 | | | | |
| S41 | 6.93 | 59.92% | 0.14 | 1.17% | 0.00 | 0.28 | | | | |
| S42 | 6.06 | 58.14% | 0.13 | 1.28% | 0.00 | 0.24 | | | | |
| S43 | 3.49 | 30.88% | 0.09 | 0.75% | 0.00 | 0.09 | | | | |

[Example 3] Verification of Relationship Between Stevia Plant with High TSG Content and Genetic Feature C (1) Isolation of Individual with High Sweet Content (M0 Generation)

Approximately 2000 (based on weight) wild type *stevia* seeds (commercial variety; introduced in August 2014) were divided into 3 groups, each of which was genetically modified by a treatment with 0.1%, 0.2% or 0.3% ethylmethanesulfonic acid (EMS).

The seeds thus treated with EMS and untreated seeds were seeded in a greenhouse within the Suntory research center to obtain EMS-treated generation (M0 generation) seedlings. No difference in the rate of germination was seen among the treatment concentrations.

An appropriate amount of fresh leaves was sampled from the EMS-treated generation (M0 generation) and untreated individuals, and the concentration of a sweet component was quantitatively determined by LC/MS-MS (Shimadzu LCMS8050). Specifically, 0.25 g of fresh leaves was dried by freeze drying, and 0.05 g of homogenized dry matter thereof was added into pure water. Extraction by ultrasonic treatment for 20 minutes, and centrifugation and filtration were performed to obtain 0.33 ml of a liquid extract. The concentrations of RebA, RebB, RebC, RebD, RebF, RebM, RebN and RebO were quantitatively determined by LC/MS-MS analysis on this liquid extract in a LCMS8050 ion mode (Shimadzu LCMS8050), and the total sum thereof was regarded as the concentration of the sweet component. Individuals having a sweet component concentration of approximately 20% were used as parent individuals 1 (P1). Also, individuals which were derived from other populations of *stevia* plants and had a sweet component concentration of 5% in a dried leaf were selected as parent individuals 2 (P2).

(2) Isolation of High Sweet Content Individual (M1 Generation) and Gene Analysis The first treated generation (M1 generation) seeds were produced by the crossing of the parent individuals 1 (P1) with the parent individuals 2 (P2), and seeded in a greenhouse within the Suntory research center to obtain M1 generation seedlings (segregating population of 1603 individuals). An appropriate amount of fresh leaves was sampled from the M1 generation individuals, and the concentration of a sweet component was quantitatively determined by LC/MS-MS (Shimadzu LCMS8050) in the same way as above. The results are shown in FIG. 1.

Genomic DNA was extracted from fresh leaves of 30 individuals with highest content of the sweet component (high sweet content individuals) and 30 individuals with lowest content of the sweet component (low sweet content individuals), and examined for a variation present only in any one of the individual groups. Among variations detected by the genomic analysis, 306 variations which had a sufficient amount of genomic information (sequence coverage: ×5 or more), had no continuation of variations, and were free from a sequence insertion or deletion were each studied for an individual in which the variation was present. As a result, a variation from C to A (C49A) at position 49 of SEQ ID NO: 1 was found to be present in the high sweet content individuals, but be absent in the low sweet content individuals.

(3) Verification of Relationship Between Variation C49A and Sweet Content

*Stevia* plants heterozygously having the variation C49A were crossed with *stevia* plants lacking the variation C49A to obtain two segregating populations (segregating population A (443 individuals) and segregating population B (446 individuals)). The presence or absence of the variation C49A in each individual of both the segregating populations, and a sweet content were examined. The dCAPS method was used in the examination of the presence or absence of the variation C49A. Genomic DNA was extracted from each individual, and PCR was performed using the primers given below. A restriction enzyme (SpeI) was added to the PCR product, and enzymatic reaction was performed at 37° C. After the restriction enzyme treatment, electrophoresis was performed using a microchip type electrophoresis apparatus LabChip GX Touch HT (PerkinElmer). The marker was identified on the basis of a band pattern after the electrophoresis.

Forward primer:
(SEQ ID NO: 112)
5'-TTATTTAATGATCCAATGGAGGGGGTGATTCAGGTAATAAAAGG
CACT-3'

Reverse primer:
(SEQ ID NO: 65)
5'-TGAGGGTTCTCAATTGATTTCCGATTGG-3'

When a restriction enzyme-treated product of approximately 321 bp (e.g., SEQ ID NO: 68) was formed by the SpeI restriction enzyme treatment of the obtained PCR product of approximately 367 bp (e.g., SEQ ID NO: 66 or 67), the test subject was regarded as being positive for the variation C49A.

The quantitative determination of the sweet content was performed in the same way as in (1).

Figure 2:
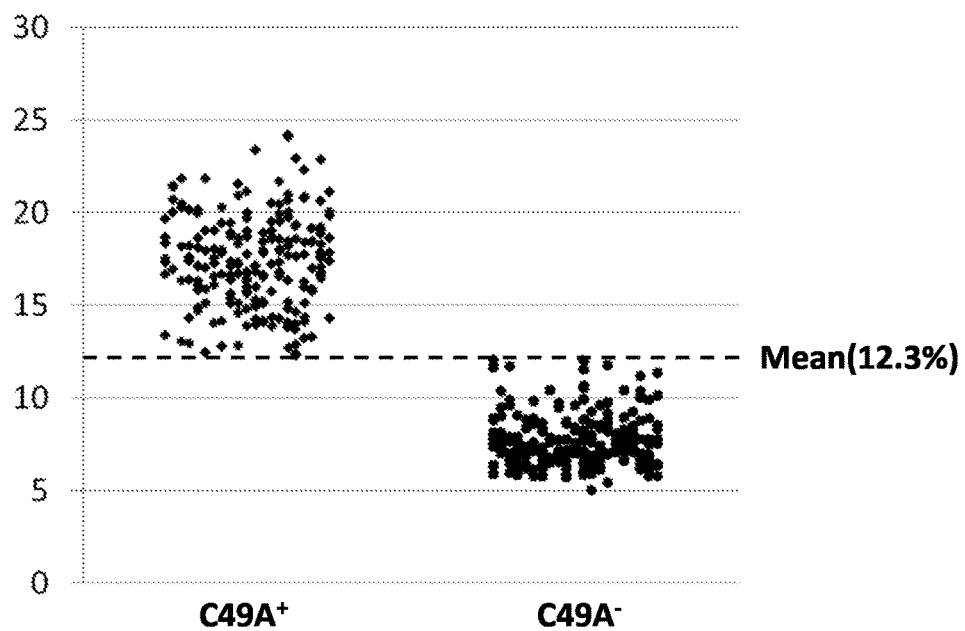
FIG. 2 is a diagram showing a distribution of sweet component contents in variation C49A positive individuals (C49A$^+$) and negative individuals (C49A$^-$) of segregating population A. The ordinate depicts a sweet component concentration (%) in a dried leaf, and the dotted line depicts an average sweet component concentration of all the individuals belonging to segregating population A.
Figure 3:
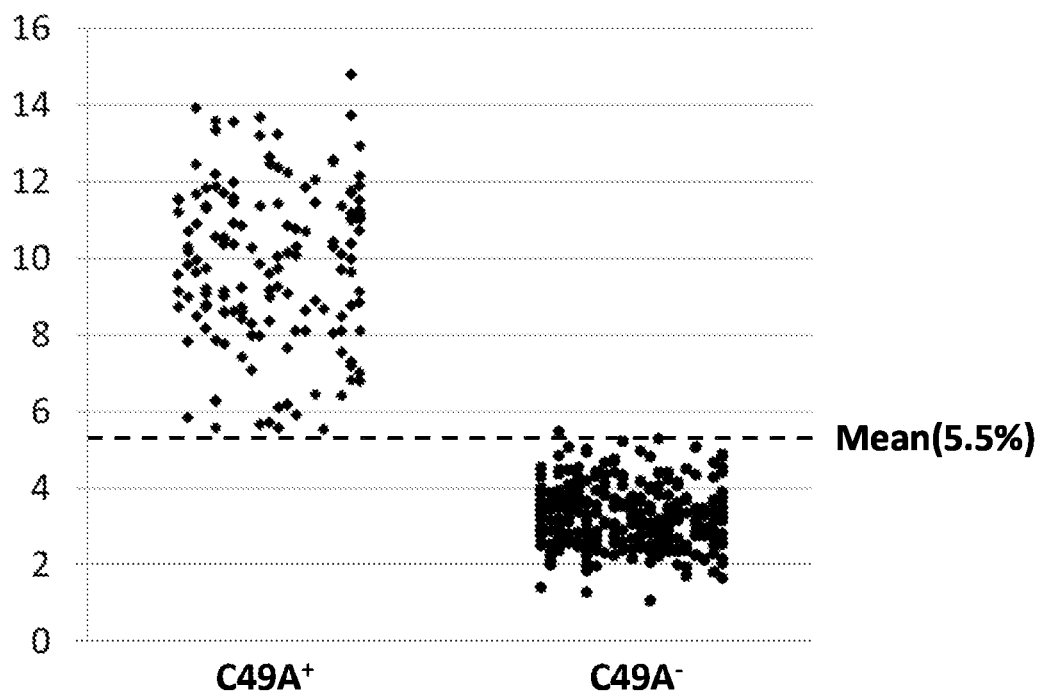
FIG. 3 is a diagram showing a distribution of sweet component contents in variation C49A positive individuals (C49A$^+$) and negative individuals (C49A$^-$) of segregating population B. The ordinate depicts a sweet component concentration (%) in a dried leaf, and the dotted line depicts an average sweet component concentration of all the individuals belonging to segregating population B.

The distribution of sweet contents of variation C49A positive individuals and negative individuals of each segregating population is shown in FIGS. 2 and 3. As is evident from these results, the sweet contents of the variation C49A positive individuals were higher than the average sweet content of each whole segregating population.

The average and median sweet contents of the variation C49A positive individuals and negative individuals in each segregating population are summarized below.

TABLE 12

Average and median sweet component concentrations (%) in dried leaves of each segregating population

|  |  | Average (%) | Median (%) |
|---|---|---|---|
| Segregating population A | Total | 12.3 | 10.4 |
|  | C49A+ | 17.4 | 17.3 |
|  | C49A− | 7.7 | 7.5 |
| Segregating population B | Total | 5.5 | 3.7 |
|  | C49A+ | 9.8 | 10.0 |
|  | C49A− | 3.3 | 3.2 |

C: Heterozygous for the allele wherein the base at the position corresponding to position 49 of SEQ ID NO: 6 is A.

As shown in Example 3, the genetic feature is related to the high TSG-content characteristics.

Both P1 and P2 are progeny of individuals genetically modified by ethylmethanesulfonic acid (EMS) treatment.

An appropriate amount of fresh leaves was sampled from the P1, P2 and S1 generation individuals, 0.25 g of fresh leaves was dried by freeze drying, and 0.05 g of homogenized dry matter thereof was added into pure water. Extraction by ultrasonic treatment for 20 minutes, and centrifugation and filtration were performed to obtain 0.33 ml of a liquid extract. The concentrations (% by mass with respect to a dried leaf) of RebA, RebB, RebC, RebD, RebF, RebM, RebN and RebO were quantitatively determined by LC/MS-MS analysis on this liquid extract in a LCMS8050 ion mode (Shimadzu LCMS8050), and the total sum thereof was regarded as the concentration of total steviol glycoside (TSG). The results are shown in the table below.

TABLE 13

Glycoside concentration in crossing parents and S1 generation individuals

| ID number | RebA (% by mass) | RebD (% by mass) | RebD/TSG (%) | RebM (% by mass) | RebM/TSG (%) | RebD + RebM (% by mass) | RebD + RebM/TSG (%) | TSG (% by mass) |
|---|---|---|---|---|---|---|---|---|
| P1 | 16.9 | 1.0 | 2.8 | 0.1 | 0.3 | 1.1 | 3.1 | 36 |
| P2 | 2.8 | 0.5 | 12.2 | 0.4 | 9.8 | 0.9 | 22.0 | 4.1 |
| S1-1 | 3.5 | 3.9 | 33.9 | 0.6 | 5.2 | 4.5 | 39.1 | 11.5 |
| S1-2 | 4.0 | 3.6 | 31.9 | 0.7 | 6.2 | 4.3 | 38.1 | 11.3 |
| S1-3 | 6.1 | 3.4 | 27.9 | 0.8 | 6.6 | 4.2 | 34.4 | 12.2 |
| S1-4 | 6.8 | 2.5 | 20.5 | 0.6 | 4.9 | 3.1 | 25.4 | 12.2 |
| S1-5 | 6.8 | 2.4 | 20.5 | 0.7 | 6.0 | 3.1 | 26.5 | 11.7 |
| S1-6 | 7.2 | 1.5 | 13.6 | 1.0 | 9.1 | 2.5 | 22.7 | 11 |
| S1-7 | 9.2 | 0.8 | 6.7 | 0.5 | 4.2 | 1.3 | 10.9 | 11.9 |
| S1-8 | 6.2 | 0.8 | 5.6 | 0.1 | 0.7 | 0.9 | 6.3 | 14.4 |
| S1-9 | 6.5 | 0.8 | 5.1 | 0.1 | 0.6 | 0.9 | 5.7 | 15.7 |

[Example 4] Verification of Relationship Between Stevia Plant with High RebD Content and Genetic Features A to C 1. Production of Test Lines Male stocks (P1) having a high TSG-content genetic feature were crossed with female stocks (P2) having a high RebM-content genetic feature to produce the first filial generation (S1 generation) seeds. The seeds were seeded in a greenhouse within the Suntory research center to obtain S1 generation seedlings.

The high RebM-content genetic feature has at least one of the following features.

B-1: Homozygous for the allele wherein the base at the position corresponding to position 40 of SEQ ID NO: 2 is T.

B-2: Homozygous for the allele wherein the base at the position corresponding to position 44 of SEQ ID NO: 3 is T.

B-3: Homozygous for the allele wherein the base at the position corresponding to position 41 of SEQ ID NO: 4 is C.

B-4: Homozygous for the allele wherein the portion corresponding to positions 55-72 of SEQ ID NO: 5 is deleted.

As shown in Examples 1 and 2, these genetic features are related to the high RebM-content characteristics.

The high TSG-content genetic feature has the following feature.

As shown in the results, high RebD-content individuals having a RebD content exceeding 3.3% by mass based on a dried leaf were obtained (S1-1 to S1-3) by the crossing of P1 with P2.

[Example 5] Detection of Genetic Feature Unique to Stevia Plant with High RebD Content Genomic DNA was extracted from the fresh leaves of each individual tested in Example 4, and examined for the condition retaining the genetic features B-1 and C.

For the detection of the genetic feature B-1, PCR was performed using the primers given below. A restriction enzyme (KpnI) was added to the PCR product, and enzymatic reaction was performed at 37° C. for treatment with the restriction enzyme. After the restriction enzyme treatment, electrophoresis was performed using a microchip type electrophoresis apparatus LabChip GX Touch HT. The marker was identified on the basis of a band pattern after the electrophoresis.

The primer sequences are as follows.

Fw primer:
(SEQ ID NO: 45)
5'-TAATCATCCAAACCCTAATCTCGCCAAACAACCGGGTAC-3'

-continued

Rv primer:
(SEQ ID NO: 46)
5'-GAGGAAGACATTGGCAACTC-3'

When a restriction enzyme-treated product of approximately 260 bp (e.g., SEQ ID NO: 49) was not formed by the KpnI restriction enzyme treatment of the obtained PCR product (approximately 297 bp long), the test subject was regarded as being positive for the genetic feature B-1.

For the detection of the genetic feature C, PCR was performed using the primers given below. A restriction enzyme (SpeI) was added to the PCR product, and enzymatic reaction was performed at 37° C. for treatment with the restriction enzyme. After the restriction enzyme treatment, electrophoresis was performed using a microchip type electrophoresis apparatus LabChip GX Touch HT (PerkinElmer). The marker was identified on the basis of a band pattern after the electrophoresis.

Forward primer:
(SEQ ID NO: 112)
5'-TTATTTAATGATCCAATGGAGGGGGTGATTCAGGTAATAAAAG
GCACT-3'

Reverse primer:
(SEQ ID NO: 65)
5'-TGAGGGTTCTCAATTGATTTCCGATTGG-3'

When a restriction enzyme-treated product of approximately 321 bp (e.g., SEQ ID NO: 68) was formed by the SpeI restriction enzyme treatment of the obtained PCR product of approximately 367 bp (e.g., SEQ ID NO: 66 or 67), the test subject was regarded as being positive for the genetic feature C.

The results are shown in Table 14 below. In the table, the circle mark represents that the corresponding variation was detected, and the x mark represents that the corresponding variation was not detected.

TABLE 14

| ID number | Genetic feature | |
|---|---|---|
| | B-1 | C |
| P1 | x | ○ |
| P2 | ○ | x |
| S1-1 | ○ | ○ |
| S1-2 | ○ | ○ |
| S1-3 | ○ | ○ |
| S1-4 | ○ | ○ |
| S1-5 | ○ | ○ |
| S1-6 | ○ | ○ |
| S1-7 | ○ | ○ |
| S1-8 | x | ○ |
| S1-9 | x | ○ |

As shown in the results, the individuals retaining the genetic feature B-1 tended to have a higher RebM content than that of the individuals not retaining the genetic feature B-1, and the individuals retaining the genetic feature C tended to have higher TSG content than that of the individuals not retaining the genetic feature C. This supports the results shown in the earlier applications by the present applicant.

In order to find a marker for identifying individuals with high RebD content, genomic DNA was extracted from the fresh leaves of each individual and sequenced with NGS (HiSeq 2500, Illumina, Inc.). As a result, the following genetic feature was found only in the individuals with high RebD content.

A: Homozygous for the allele wherein the base at the position corresponding to position 201 of SEQ ID NO: 1 is A.

As shown in the results, all the individuals with high RebD content (S1-1 to S1-3) retained the genetic features A, B-1 and C and tended to have a higher RebD content than that of the individuals not retaining the genetic feature A.

[Example 6] Verification of Relationship Between Ability to Form Flower Buds and Genetic Feature X After cutting of two wild type *stevia* plant lines (W101 and W102) and one variant *stevia* plant line (M101) which was progeny of individuals genetically modified by a mutagenesis treatment with ethylmethanesulfonic acid (EMS), plants each having 8 true leaves were placed under each condition shown in the table below. Three weeks later, the number of flower buds was counted. The results are shown in the table below (an average value from 3 stocks of each treatment plot, the smallest to largest values within the parentheses).

TABLE 15

| Line | 16-hour lighting | 12-hour lighting | 8-hour lighting |
|---|---|---|---|
| W101 | 0 | 8.0 (7-9) | 16.3 (15-18) |
| W102 | 0 | 6.6 (6-8) | 15.3 (13-18) |
| M101 | 0 | 0 (0-0) | 2.0 (0-4) |

As shown in the results, the ability of M101 to form flower buds was markedly low as compared with the wild type line. In order to examine a genetic feature related to this phenotype, the gene sequences of these lines were determined and compared. As a result, the genetic features X-1 and X-2 were found only in M101.

INDUSTRIAL APPLICABILITY

The present invention enables the provision of a *stevia* plant with high yields of leaves and steviol glycosides and can therefore achieve efficient production of steviol glycosides. The present invention can achieve the selection of individuals having a low ability to form flower buds before flower bud formation and therefore enables improvement in breeding efficiency.

The invention claimed is:

1. A *stevia* plant which is heterozygous or homozygous for the allele wherein the base at the position corresponding to position 90 of SEQ ID NO: 150 is G, and/or is heterozygous or homozygous for the allele wherein the base at the position corresponding to position 108 of SEQ ID NO: 150 is G.

2. The plant according to claim 1, further having at least one of the following genetic features (1) to (7):
   (1) homozygous for the allele wherein the base at the position corresponding to position 40 of SEQ ID NO: 2 is T;
   (2) homozygous for the allele wherein the base at the position corresponding to position 44 of SEQ ID NO: 3 is T;
   (3) homozygous for the allele wherein the base at the position corresponding to position 48 of SEQ ID NO: 4 is C;
   (4) homozygous for the allele wherein the portion corresponding to positions 55-72 of SEQ ID NO: 5 is deleted;
   (5) homozygous for the allele wherein the base at the position corresponding to position 201 of SEQ ID NO: 1 is A;
   (6) heterozygous for the allele wherein the base at the position corresponding to position 49 of SEQ ID NO: 6 is A;
   (7) homozygous for the allele wherein the base at the position corresponding to position 49 of SEQ ID NO: 6 is A; and
   wherein the plant optionally has at least one of the following features (a) and (b):
   (a) comprising 3% or more of RebD per unit mass of a dried leaf; and
   (b) comprising 0.2% or more of RebM per unit mass of a dried leaf.

3. The plant according to claim 1, wherein the plant has not been subjected to transfection with a foreign gene.

4. The plant according to claim 1, wherein the plant comprises a *stevia* plant subjected to a mutagenesis treatment and a progeny plant thereof.

5. A seed, a tissue, a tissue culture or a cell of the plant according to claim 1.

6. The tissue, tissue culture or cell according to claim 5, which is selected from an embryo, a meristem cell, a pollen, a leaf, a root, a root apex, a petal, a protoplast, a leaf section and a callus.

7. A method of producing the *stevia* plant according to claim 1, the method comprising crossing the plant according to claim 1 with a second *stevia* plant.

8. The method according to claim 7, wherein the second plant is heterozygous or homozygous for the allele wherein the base at the position corresponding to position 90 of SEQ ID NO: 150 is G, and/or being heterozygous or homozygous for the allele wherein the base at the position corresponding to position 108 of SEQ ID NO: 150 is G.

9. A method of producing a *stevia* extract, comprising obtaining an extract from the plant according to claim 1, or from the seed, tissue, tissue culture or cell of the plant.

10. A method of producing a steviol glycoside purified product, comprising:
    obtaining an extract from the plant according to claim 1, or from the seed, tissue, tissue culture or cell of the plant; and
    purifying a steviol glycoside from the obtained extract, wherein the steviol glycoside optionally comprises rebaudioside A, rebaudioside B, rebaudioside C, rebaudioside D, rebaudioside E, rebaudioside F, rebaudioside M, rebaudioside N, rebaudioside O, stevioside, steviolbioside, rubusoside, dulcoside A or a combination thereof.

11. A method of producing a food or beverage, a sweetener composition, a flavor or a medicament, comprising:
    obtaining an extract from the plant according to claim 1, or from a seed, tissue, tissue culture or cell of the plant; and
    adding the extract to a raw material for the food or beverage, sweetener composition, flavor or medicament.

12. A method of producing a *stevia* plant according to claim 1, comprising
    introducing a variation from A to G to a position corresponding to position 90 of SEQ ID NO: 150, and/or
    introducing a variation from T to G to a position corresponding to position 108 of SEQ ID NO: 150.

13. A method of producing a food or beverage, a sweetener composition, a flavor or a medicament, comprising:
    obtaining an extract from the plant according to claim 1, or from a seed, tissue, tissue culture or cell of the plant;
    purifying a steviol glycoside from the extract; and
    adding the steviol glycoside to a raw material for the food or beverage, sweetener composition, flavor or medicament.

14. The plant according to claim 2, wherein the plant has at least one of the following features (a) and (b):
    (a) comprising 3% or more of RebD per unit mass of a dried leaf; and
    (b) comprising 0.2% or more of RebM per unit mass of a dried leaf.

15. The plant according to claim 1, further having at least the following genetic features:
    homozygous for the allele wherein the base at the position corresponding to position 40 of SEQ ID NO: 2 is T; homozygous for the allele wherein the base at the position corresponding to position 44 of SEQ ID NO: 3 is T; homozygous for the allele wherein the base at the position corresponding to position 48 of SEQ ID NO: 4 is C; and homozygous for the allele wherein the portion corresponding to positions 55-72 of SEQ ID NO: 5 is deleted;
    wherein the plant optionally has at least one of the following features (a) and (b):

(a) comprising 3% or more of RebD per unit mass of a dried leaf; and
(b) comprising 0.2% or more of RebM per unit mass of a dried leaf.

16. The plant according to claim 1, further having at least the following genetic feature:
homozygous for the allele wherein the base at the position corresponding to position 201 of SEQ ID NO: 1 is A;
wherein the plant optionally has at least one of the following features (a) and (b):
(a) comprising 3% or more of RebD per unit mass of a dried leaf; and
(b) comprising 0.2% or more of RebM per unit mass of a dried leaf.

17. The plant according to claim 1, further having at least following genetic feature:
heterozygous or homozygous for the allele wherein the base at the position corresponding to position 49 of SEQ ID NO: 6 is A;
wherein the plant optionally has at least one of the following features (a) and (b):
(a) comprising 3% or more of RebD per unit mass of a dried leaf; and
(b) comprising 0.2% or more of RebM per unit mass of a dried leaf.

* * * * *

SEQUENCE LISTING

<160> NUMBER OF SEQ ID NOS: 192

<210> SEQ ID NO 1
<211> LENGTH: 399
<212> TYPE: DNA
<213> ORGANISM: Stevia rebaudiana

<400> SEQUENCE: 1

| agactcgatc | gcagcctcga | tcggcgagtc | ggcgattgag | atgatgattc | attcaacaaa | 60 |
| cacatggttt | gggaatagct | ctgttgttgc | ctcggtcggc | gaatctacaa | acaagagggt | 120 |
| cttcgcttcc | atgtcgaacc | atttgaaaac | caaagctctg | ataccaaat | gatgcagtta | 180 |
| atgaatacaa | ccaaatggct | cagaacaact | gattaatcaa | actcttaaaa | ggaaccaaga | 240 |
| ggttcaagaa | caaagttctt | ataaactcaa | attcaatcaa | aaaactgatt | tgaaacttaa | 300 |
| tttcaagtgt | ttaaatagaa | acatttcta | aacagataaa | gactaaaatt | caaataatta | 360 |
| aataaagata | aactataatt | tgaattaaga | gatgatatg  |            |            | 399 |

<210> SEQ ID NO 2
<211> LENGTH: 137
<212> TYPE: DNA
<213> ORGANISM: Stevia rebaudiana

<400> SEQUENCE: 2

| taatcatcca | aaccctaatc | tcgccaaaca | accgaatacc | gatccaaacc | ctgaaatgag | 60 |
| cacaactctt | gaacctgatc | acgagaatga | agagcacaaa | catgttatga | cacatgtaaa | 120 |
| cgatggtttt | tgctaca    |            |            |            |            | 137 |

<210> SEQ ID NO 3
<211> LENGTH: 141
<212> TYPE: DNA
<213> ORGANISM: Stevia rebaudiana

<400> SEQUENCE: 3

| aaggttcttt | attttaaac | ttatgttaat | ttattgtatc | ttgaagttaa | tcaagagatg | 60 |
| ctctcttgga | gaaattttat | ggtcataaaa | cctatatcaa | agagatgctc | tcttggtata | 120 |
| ttccatactt | aaaatatcta | t          |            |            |            | 141 |

<210> SEQ ID NO 4
<211> LENGTH: 137
<212> TYPE: DNA
<213> ORGANISM: Stevia rebaudiana

<400> SEQUENCE: 4

| cgatggtttt | tgctacatga | aaaccctaga | agacgaaacc | cgtttaagtg | taaatcttga | 60 |
| aaacacattc | tttgatgaag | aaccccttc | gtatccggat | cttatggact | tttctgcatc | 120 |
| gaaaaggac | gaatacg    |            |            |            |            | 137 |

<210> SEQ ID NO 5
<211> LENGTH: 158
<212> TYPE: DNA
<213> ORGANISM: Stevia rebaudiana

<400> SEQUENCE: 5

| cgcaaacacg | tatactaatc | acgtaacata | tttttattt | ctaaattaaa | attttataac | 60 |
| aatatcatac | ttgaattaaa | gataacataa | tatttatttt | tagagtgtaa | cttctaaaaa | 120 |
| atatcaacct | acgaaaaagt | tgtacatacc | atgctaaa  |            |            | 158 |

<210> SEQ ID NO 6
<211> LENGTH: 367
<212> TYPE: DNA
<213> ORGANISM: Stevia rebaudiana -continued

<400> SEQUENCE: 6

```
ttatttaatg atccaatgga gggggtgatt caggtaataa aaggcattcg tatggaatat      60
accaaaacat tgcgattcgt tattagcatg gatctttcaa gtaataaact tatcggagaa     120
ataccagttg agttaactgc ccttcatgcc ttggtgagtc tcaatttgtc taataatcat     180
cttattggac acattccgaa tagcattgga aacatgaaag ctttaaattc tctagatttc     240
tcgagaaacg agttaaatgg gttgatccct ccaagcattg gagctttgaa ttttttgagt     300
catttaaatt tgtcaaacaa caacttatca ggaccaattc caatcggaaa tcaattgaga     360
accctca                                                               367
```

<210> SEQ ID NO 7
<211> LENGTH: 14
<212> TYPE: DNA
<213> ORGANISM: Artificial Sequence
<220> FEATURE:
<223> OTHER INFORMATION: Synthetic DNA

<400> SEQUENCE: 7

```
atggtttggg aata                                                        14
```

<210> SEQ ID NO 8
<211> LENGTH: 15
<212> TYPE: DNA
<213> ORGANISM: Artificial Sequence
<220> FEATURE:
<223> OTHER INFORMATION: Synthetic DNA

<400> SEQUENCE: 8

```
agaactttgt tcttg                                                       15
```

<210> SEQ ID NO 9
<211> LENGTH: 15
<212> TYPE: DNA
<213> ORGANISM: Artificial Sequence
<220> FEATURE:
<223> OTHER INFORMATION: Synthetic DNA

<400> SEQUENCE: 9

```
taatcatcca aaccc                                                       15
```

<210> SEQ ID NO 10
<211> LENGTH: 15
<212> TYPE: DNA
<213> ORGANISM: Artificial Sequence
<220> FEATURE:
<223> OTHER INFORMATION: Synthetic DNA

<400> SEQUENCE: 10

```
tgtagcaaaa accat                                                       15
```

<210> SEQ ID NO 11
<211> LENGTH: 15
<212> TYPE: DNA
<213> ORGANISM: Artificial Sequence
<220> FEATURE:
<223> OTHER INFORMATION: Synthetic DNA

<400> SEQUENCE: 11

```
aaggttcttt atttt                                                       15
```

<210> SEQ ID NO 12
<211> LENGTH: 15

```
<212> TYPE: DNA
<213> ORGANISM: Artificial Sequence
<220> FEATURE:
<223> OTHER INFORMATION: Synthetic DNA

<400> SEQUENCE: 12
atagatattt taagt                                                    15

<210> SEQ ID NO 13
<211> LENGTH: 15
<212> TYPE: DNA
<213> ORGANISM: Artificial Sequence
<220> FEATURE:
<223> OTHER INFORMATION: Synthetic DNA

<400> SEQUENCE: 13
cgatggtttt tgcta                                                    15

<210> SEQ ID NO 14
<211> LENGTH: 15
<212> TYPE: DNA
<213> ORGANISM: Artificial Sequence
<220> FEATURE:
<223> OTHER INFORMATION: Synthetic DNA

<400> SEQUENCE: 14
cgtattcgtc ctttt                                                    15

<210> SEQ ID NO 15
<211> LENGTH: 15
<212> TYPE: DNA
<213> ORGANISM: Artificial Sequence
<220> FEATURE:
<223> OTHER INFORMATION: Synthetic DNA

<400> SEQUENCE: 15
cgcaaacacg tatac                                                    15

<210> SEQ ID NO 16
<211> LENGTH: 15
<212> TYPE: DNA
<213> ORGANISM: Artificial Sequence
<220> FEATURE:
<223> OTHER INFORMATION: Synthetic DNA

<400> SEQUENCE: 16
tttagcatgg tatgt                                                    15

<210> SEQ ID NO 17
<211> LENGTH: 14
<212> TYPE: DNA
<213> ORGANISM: Artificial Sequence
<220> FEATURE:
<223> OTHER INFORMATION: Synthetic DNA

<400> SEQUENCE: 17
ttatttaatg atcc                                                     14

<210> SEQ ID NO 18
<211> LENGTH: 15
<212> TYPE: DNA
<213> ORGANISM: Artificial Sequence
<220> FEATURE:
<223> OTHER INFORMATION: Synthetic DNA

<400> SEQUENCE: 18
```

```
tgagggttct caatt                                                15
```

<210> SEQ ID NO 19
<211> LENGTH: 21
<212> TYPE: DNA
<213> ORGANISM: Stevia rebaudiana

<400> SEQUENCE: 19

```
ccaaatggct aagaacaact g                                         21
```

<210> SEQ ID NO 20
<211> LENGTH: 41
<212> TYPE: DNA
<213> ORGANISM: Stevia rebaudiana

<400> SEQUENCE: 20

```
atgaatacaa ccaaatggct aagaacaact gattaatcaa a                   41
```

<210> SEQ ID NO 21
<211> LENGTH: 61
<212> TYPE: DNA
<213> ORGANISM: Stevia rebaudiana

<400> SEQUENCE: 21

```
gatgcagtta atgaatacaa ccaaatggct aagaacaact gattaatcaa actcttaaaa   60
g                                                                   61
```

<210> SEQ ID NO 22
<211> LENGTH: 21
<212> TYPE: DNA
<213> ORGANISM: Stevia rebaudiana

<400> SEQUENCE: 22

```
aaccgaatac tgatccaaac c                                         21
```

<210> SEQ ID NO 23
<211> LENGTH: 41
<212> TYPE: DNA
<213> ORGANISM: Stevia rebaudiana

<400> SEQUENCE: 23

```
ctcgccaaac aaccgaatac tgatccaaac cctgaaatga g                   41
```

<210> SEQ ID NO 24
<211> LENGTH: 61
<212> TYPE: DNA
<213> ORGANISM: Stevia rebaudiana

<400> SEQUENCE: 24

```
aaaccctaat ctcgccaaac aaccgaatac tgatccaaac cctgaaatga gcacaactct   60
t                                                                   61
```

<210> SEQ ID NO 25
<211> LENGTH: 21
<212> TYPE: DNA
<213> ORGANISM: Stevia rebaudiana

<400> SEQUENCE: 25

```
ttgtatcttg tagttaatca a                                         21
```

<210> SEQ ID NO 26
<211> LENGTH: 41

<212> TYPE: DNA
<213> ORGANISM: Stevia rebaudiana

<400> SEQUENCE: 26
tgttaattta ttgtatcttg tagttaatca agagatgctc t          41

<210> SEQ ID NO 27
<211> LENGTH: 61
<212> TYPE: DNA
<213> ORGANISM: Stevia rebaudiana

<400> SEQUENCE: 27
tttaaactta tgttaattta ttgtatcttg tagttaatca agagatgctc tcttggagaa    60
a                                                                   61

<210> SEQ ID NO 28
<211> LENGTH: 21
<212> TYPE: DNA
<213> ORGANISM: Stevia rebaudiana

<400> SEQUENCE: 28
acccgtttaa ctgtaaatct t          21

<210> SEQ ID NO 29
<211> LENGTH: 41
<212> TYPE: DNA
<213> ORGANISM: Stevia rebaudiana

<400> SEQUENCE: 29
agaagacgaa acccgtttaa ctgtaaatct tgaaaacaca t          41

<210> SEQ ID NO 30
<211> LENGTH: 61
<212> TYPE: DNA
<213> ORGANISM: Stevia rebaudiana

<400> SEQUENCE: 30
tgaaacccct agaagacgaa acccgtttaa ctgtaaatct tgaaaacaca ttctttgatg    60
a                                                                   61

<210> SEQ ID NO 31
<211> LENGTH: 20
<212> TYPE: DNA
<213> ORGANISM: Stevia rebaudiana

<400> SEQUENCE: 31
attaaaattt gaattaaaga          20

<210> SEQ ID NO 32
<211> LENGTH: 40
<212> TYPE: DNA
<213> ORGANISM: Stevia rebaudiana

<400> SEQUENCE: 32
ttatttctaa attaaaattt gaattaaaga taacataata          40

<210> SEQ ID NO 33
<211> LENGTH: 60
<212> TYPE: DNA
<213> ORGANISM: Stevia rebaudiana

<400> SEQUENCE: 33

```
aacatatttt ttatttctaa attaaaattt gaattaaaga taacataata tttattttta    60
```

<210> SEQ ID NO 34
<211> LENGTH: 21
<212> TYPE: DNA
<213> ORGANISM: Stevia rebaudiana

<400> SEQUENCE: 34

```
aaaaggcatt agtatggaat a                                              21
```

<210> SEQ ID NO 35
<211> LENGTH: 41
<212> TYPE: DNA
<213> ORGANISM: Stevia rebaudiana

<400> SEQUENCE: 35

```
ttcaggtaat aaaaggcatt agtatggaat ataccaaaac a                        41
```

<210> SEQ ID NO 36
<211> LENGTH: 61
<212> TYPE: DNA
<213> ORGANISM: Stevia rebaudiana

<400> SEQUENCE: 36

```
gaggggggtga ttcaggtaat aaaaggcatt agtatggaat ataccaaaac attgcgattc   60
g                                                                    61
```

<210> SEQ ID NO 37
<211> LENGTH: 25
<212> TYPE: DNA
<213> ORGANISM: Artificial Sequence
<220> FEATURE:
<223> OTHER INFORMATION: Synthetic DNA

<400> SEQUENCE: 37

```
atggtttggg aatagctctg ttgtt                                          25
```

<210> SEQ ID NO 38
<211> LENGTH: 24
<212> TYPE: DNA
<213> ORGANISM: Artificial Sequence
<220> FEATURE:
<223> OTHER INFORMATION: Synthetic DNA

<400> SEQUENCE: 38

```
agaactttgt tcttgaacct cttg                                           24
```

<210> SEQ ID NO 39
<211> LENGTH: 196
<212> TYPE: DNA
<213> ORGANISM: Artificial Sequence
<220> FEATURE:
<223> OTHER INFORMATION: Synthetic DNA

<400> SEQUENCE: 39

```
atggtttggg aatagctctg ttgttgcctc ggtcggcgaa tctacaaaca agagggtctt    60
cgcttccatg tcgaaccatt tgaaaaccaa agctctgaat accaaatgat gcagttaatg   120
aatacaacca aatggctaag aacaactgat taatcaaact cttaaaagga accaagaggt   180
tcaagaacaa agttct                                                   196
```

<210> SEQ ID NO 40
<211> LENGTH: 196

```
<212> TYPE: DNA
<213> ORGANISM: Artificial Sequence
<220> FEATURE:
<223> OTHER INFORMATION: Synthetic DNA

<400> SEQUENCE: 40
atggtttggg aatagctctg ttgttgcctc ggtcggcgaa tctacaaaca agagggtctt      60
cgcttccatg tcgaaccatt tgaaaaccaa agctctgaat accaaatgat gcagttaatg     120
aatacaacca atggctcag aacaactgat taatcaaact cttaaaagga accaagaggt      180
tcaagaacaa agttct                                                     196

<210> SEQ ID NO 41
<211> LENGTH: 96
<212> TYPE: DNA
<213> ORGANISM: Artificial Sequence
<220> FEATURE:
<223> OTHER INFORMATION: Synthetic DNA

<400> SEQUENCE: 41
atggtttggg aatagctctg ttgttgcctc ggtcggcgaa tctacaaaca agagggtctt      60
cgcttccatg tcgaaccatt tgaaaaccaa agctct                                96

<210> SEQ ID NO 42
<211> LENGTH: 100
<212> TYPE: DNA
<213> ORGANISM: Artificial Sequence
<220> FEATURE:
<223> OTHER INFORMATION: Synthetic DNA

<400> SEQUENCE: 42
gaataccaaa tgatgcagtt aatgaataca accaaatggc taagaacaac tgattaatca      60
aactcttaaa aggaaccaag aggttcaaga acaaagttct                           100

<210> SEQ ID NO 43
<211> LENGTH: 43
<212> TYPE: DNA
<213> ORGANISM: Artificial Sequence
<220> FEATURE:
<223> OTHER INFORMATION: Synthetic DNA

<400> SEQUENCE: 43
gaataccaaa tgatgcagtt aatgaataca accaaatggc tca                        43

<210> SEQ ID NO 44
<211> LENGTH: 57
<212> TYPE: DNA
<213> ORGANISM: Artificial Sequence
<220> FEATURE:
<223> OTHER INFORMATION: Synthetic DNA

<400> SEQUENCE: 44
gaacaactga ttaatcaaac tcttaaaagg aaccaagagg ttcaagaaca aagttct         57

<210> SEQ ID NO 45
<211> LENGTH: 39
<212> TYPE: DNA
<213> ORGANISM: Artificial Sequence
<220> FEATURE:
<223> OTHER INFORMATION: Synthetic DNA

<400> SEQUENCE: 45
taatcatcca aaccctaatc tcgccaaaca accgggtac                             39
```

<210> SEQ ID NO 46
<211> LENGTH: 20
<212> TYPE: DNA
<213> ORGANISM: Artificial Sequence
<220> FEATURE:
<223> OTHER INFORMATION: Synthetic DNA

<400> SEQUENCE: 46
gaggaagaca ttggcaactc                                                  20

<210> SEQ ID NO 47
<211> LENGTH: 297
<212> TYPE: DNA
<213> ORGANISM: Artificial Sequence
<220> FEATURE:
<223> OTHER INFORMATION: Synthetic DNA

<400> SEQUENCE: 47
taatcatcca aaccctaatc tcgccaaaca accgggtact gatccaaacc ctgaaatgag       60
cacaactctt gaacctgatc acgagaatga agagcacaaa catgttatga cacatgtaaa      120
cgatggtttt tgctacatga aaaccctaga agacgaaacc cgtttaactg taaatcttga      180
aaacacattc tttgatgaaa aacccctttc gtatccggat cttatggact tttctgcatc      240
gaaaacggac gaatacgact tctatgatga acttgaagag ctgccaatgt cttcctc        297

<210> SEQ ID NO 48
<211> LENGTH: 297
<212> TYPE: DNA
<213> ORGANISM: Artificial Sequence
<220> FEATURE:
<223> OTHER INFORMATION: Synthetic DNA

<400> SEQUENCE: 48
taatcatcca aaccctaatc tcgccaaaca accgggtacc gatccaaacc ctgaaatgag       60
cacaactctt gaacctgatc acgagaatga agagcacaaa catgttatga cacatgtaaa      120
cgatggtttt tgctacatga aaaccctaga agacgaaacc cgtttaagtg taaatcttga      180
aaacacattc tttgatgaag aacccctttc gtatccggat cttatggact tttctgcatc      240
gaaaaaggac gaatacgact tctatgatga acttgaagag ttgccaatgt cttcctc        297

<210> SEQ ID NO 49
<211> LENGTH: 258
<212> TYPE: DNA
<213> ORGANISM: Artificial Sequence
<220> FEATURE:
<223> OTHER INFORMATION: Synthetic DNA

<400> SEQUENCE: 49
cgatccaaac cctgaaatga gcacaactct tgaacctgat cacgagaatg aagagcacaa       60
acatgttatg acacatgtaa acgatggttt tgctacatg aaaaccctag aagacgaaac      120
ccgtttaagt gtaaatcttg aaaacacatt ctttgatgaa gaaccccttt cgtatccgga      180
tcttatggac ttttctgcat cgaaaaagga cgaatacgac ttctatgatg aacttgaaga      240
gttgccaatg tcttcctc                                                   258

<210> SEQ ID NO 50
<211> LENGTH: 43
<212> TYPE: DNA
<213> ORGANISM: Artificial Sequence
<220> FEATURE:
<223> OTHER INFORMATION: Synthetic DNA

<400> SEQUENCE: 50
aaggttcttt atttttaaac ttatgttaat ttattgtatc tag        43

<210> SEQ ID NO 51
<211> LENGTH: 21
<212> TYPE: DNA
<213> ORGANISM: Artificial Sequence
<220> FEATURE:
<223> OTHER INFORMATION: Synthetic DNA

<400> SEQUENCE: 51
ccttatgtac acatgctaca c        21

<210> SEQ ID NO 52
<211> LENGTH: 383
<212> TYPE: DNA
<213> ORGANISM: Artificial Sequence
<220> FEATURE:
<223> OTHER INFORMATION: Synthetic DNA

<400> SEQUENCE: 52
aaggttcttt atttttaaac ttatgttaat ttattgtatc tagtagttaa tcaagagatg        60
ctctcttgga gaaattttat ggtcataaaa cctatatcaa agagatgctc tcttggtata       120
ttccatactt aaaatatcta ttttggaaaa aaagtgtagc atcttcctgc ttttagtagg       180
tgtcaatcat tattaaattt cacaaaaccg tgcaagaatc ccagtttccc tatagtttgt       240
atacgttcct gatctagtat tttacttatg tttcaaatca atccaatcat gcttgtgtcc       300
gaaaattaaa aaacaagggt attggatgcc ctgtaccact attattaact tttcagaaaa       360
acgtgtagca tgtgtacata agg        383

<210> SEQ ID NO 53
<211> LENGTH: 383
<212> TYPE: DNA
<213> ORGANISM: Artificial Sequence
<220> FEATURE:
<223> OTHER INFORMATION: Synthetic DNA

<400> SEQUENCE: 53
aaggttcttt atttttaaac ttatgttaat ttattgtatc tagaagttaa tcaagagatg        60
ctctcttgga gaaattttat ggtcataaaa cctatatcaa agagatgctc tcttggtata       120
ttccatactt aaaatatcta ttttggaaaa aaagtgtagc atcttcctgc ttttagtagg       180
tgtcaatcat tattaaattt cacaaaaccg tgcaagaatc ccagtttccc tatagtttgt       240
atacgttcct gatctagtat tttacttatg tttcaaatca gtccaatcat gcttgtgtcc       300
gaaaattaaa aaacaagggt attggatgcc ctgtaccact attattaact tttcagaaaa       360
acgtgtagca tgtgtacata agg        383

<210> SEQ ID NO 54
<211> LENGTH: 344
<212> TYPE: DNA
<213> ORGANISM: Artificial Sequence
<220> FEATURE:
<223> OTHER INFORMATION: Synthetic DNA

<400> SEQUENCE: 54
ctagaagtta atcaagagat gctctcttgg agaaattttta tggtcataaa acctatatca        60
aagagatgct ctcttggtat attccatact taaaatatct attttggaaa aaagtgtag       120

```
catcttcctg cttttagtag gtgtcaatca ttattaaatt tcacaaaacc gtgcaagaat    180
cccagtttcc ctatagtttg tatacgttcc tgatctagta ttttacttat gtttcaaatc    240
agtccaatca tgcttgtgtc cgaaaattaa aaaacaaggg tattggatgc cctgtaccac    300
tattattaac ttttcagaaa aacgtgtagc atgtgtacat aagg                     344
```

<210> SEQ ID NO 55
<211> LENGTH: 47
<212> TYPE: DNA
<213> ORGANISM: Artificial Sequence
<220> FEATURE:
<223> OTHER INFORMATION: Synthetic DNA

<400> SEQUENCE: 55

```
cgatggtttt tgctacatga aaaccctaga agacgaaacc cgcttaa                   47
```

<210> SEQ ID NO 56
<211> LENGTH: 23
<212> TYPE: DNA
<213> ORGANISM: Artificial Sequence
<220> FEATURE:
<223> OTHER INFORMATION: Synthetic DNA

<400> SEQUENCE: 56

```
accagcaata atccttgaat tag                                             23
```

<210> SEQ ID NO 57
<211> LENGTH: 390
<212> TYPE: DNA
<213> ORGANISM: Artificial Sequence
<220> FEATURE:
<223> OTHER INFORMATION: Synthetic DNA

<400> SEQUENCE: 57

```
cgatggtttt tgctacatga aaaccctaga agacgaaacc cgcttaactg taaatcttga     60
aaacacattc tttgatgaaa aacccctttc gtatccggat cttatggact tttctgcatc    120
gaaaacggac gaatacgact tctatgatga acttgaagag ctgccaatgt cttcctcatc    180
attcaaaagc ttcatgagaa gtaatttctt tgaggaaaga gttcttgttc aaccttattg    240
attaagaatt taagggaagc agattatata tgtaattaaa ttttggtatt tatactttga    300
acttaattaa taattataat aataatccca actagaggca cttagtggag attacttata    360
tataatacta attcaaggat tattgctggt                                     390
```

<210> SEQ ID NO 58
<211> LENGTH: 390
<212> TYPE: DNA
<213> ORGANISM: Artificial Sequence
<220> FEATURE:
<223> OTHER INFORMATION: Synthetic DNA

<400> SEQUENCE: 58

```
cgatggtttt tgctacatga aaaccctaga agacgaaacc cgcttaagtg taaatcttga     60
aaacacattc tttgatgaag aaccccttc gtatccggat cttatggact tttctgcatc    120
gaaaaaggac gaatacgact tctatgatga acttgaagag ttgccaatgt cttcctcatc    180
attcaaaagc ttcatgagaa gtaatttctt tgaggaaaga gttcttgttc aaccttattg    240
attaagaatt taagggaagc agattatata tgtaattaaa ttttggtatt tatactttga    300
acttaattaa taattataat aataatccca actagaggca cttagtggag attacttata    360
tataatacta attcaaggat tattgctggt                                     390
```

<210> SEQ ID NO 59
<211> LENGTH: 347
<212> TYPE: DNA
<213> ORGANISM: Artificial Sequence
<220> FEATURE:
<223> OTHER INFORMATION: Synthetic DNA

<400> SEQUENCE: 59
ttaagtgtaa atcttgaaaa cacattcttt gatgaagaac ccctttcgta tccggatctt     60
atggactttt ctgcatcgaa aaaggacgaa tacgacttct atgatgaact tgaagagttg    120
ccaatgtctt cctcatcatt caaaagcttc atgagaagta atttctttga ggaaagagtt    180
cttgttcaac cttattgatt aagaatttaa gggaagcaga ttatatatgt aattaaattt    240
tggtatttat actttgaact taattaataa ttataataat aatcccaact agaggcactt    300
agtggagatt acttatatat aatactaatt caaggattat tgctggt                 347

<210> SEQ ID NO 60
<211> LENGTH: 20
<212> TYPE: DNA
<213> ORGANISM: Artificial Sequence
<220> FEATURE:
<223> OTHER INFORMATION: Synthetic DNA

<400> SEQUENCE: 60
cgcaaacacg tatactaatc                                                 20

<210> SEQ ID NO 61
<211> LENGTH: 20
<212> TYPE: DNA
<213> ORGANISM: Artificial Sequence
<220> FEATURE:
<223> OTHER INFORMATION: Synthetic DNA

<400> SEQUENCE: 61
tttagcatgg tatgtacaac                                                 20

<210> SEQ ID NO 62
<211> LENGTH: 140
<212> TYPE: DNA
<213> ORGANISM: Artificial Sequence
<220> FEATURE:
<223> OTHER INFORMATION: Synthetic DNA

<400> SEQUENCE: 62
cgcaaacacg tatactaatc acgtaacata ttttttattt ctaaattaaa atttgaatta     60
aagataacat aatatttatt tttagagtgt aacttctaaa aaatatcaac ctacgaaaaa    120
gttgtacata ccatgctaaa                                                140

<210> SEQ ID NO 63
<211> LENGTH: 158
<212> TYPE: DNA
<213> ORGANISM: Artificial Sequence
<220> FEATURE:
<223> OTHER INFORMATION: Synthetic DNA

<400> SEQUENCE: 63
cgcaaacacg tatactaatc acgtaacata ttttttattt ctaaattaaa attttataac     60
aatatcatac ttgaattaaa gataacataa tatttatttt tagagtgtaa cttctaaaaa    120
atatcaacct acgaaaaagt tgtacatacc atgctaaa                            158

<210> SEQ ID NO 64
<211> LENGTH: 48
<212> TYPE: DNA
<213> ORGANISM: Artificial Sequence
<220> FEATURE:
<223> OTHER INFORMATION: Synthetic DNA

<400> SEQUENCE: 64
ttatttaatg atccaatgga ggggtgatt caggtaataa aaggcatt                    48

<210> SEQ ID NO 65
<211> LENGTH: 28
<212> TYPE: DNA
<213> ORGANISM: Artificial Sequence
<220> FEATURE:
<223> OTHER INFORMATION: Synthetic DNA

<400> SEQUENCE: 65
tgagggttct caattgattt ccgattgg                                         28

<210> SEQ ID NO 66
<211> LENGTH: 367
<212> TYPE: DNA
<213> ORGANISM: Artificial Sequence
<220> FEATURE:
<223> OTHER INFORMATION: Synthetic DNA

<400> SEQUENCE: 66
ttatttaatg atccaatgga ggggtgatt caggtaataa aaggcactag tatggaatat       60
accaaaacat tgcgattcgt tattagcatg gatctttcaa gtaataaact tatcggagaa      120
ataccagttg agttaactgc ccttcatgcc ttggtgagtc tcaatttgtc taataatcat     180
cttattggac acattccgaa tagcattgga aacatgaaag ctttaaattc tctagatttc    240
tcgagaaacg agttaaatgg gttgatccct ccaagcattg gagctttgaa ttttttgagt    300
catttaaatt tgtcaaacaa caacttatca ggaccaattc aatcggaaa tcaattgaga     360 accctca                                                              367

<210> SEQ ID NO 67
<211> LENGTH: 367
<212> TYPE: DNA
<213> ORGANISM: Artificial Sequence
<220> FEATURE:
<223> OTHER INFORMATION: Synthetic DNA

<400> SEQUENCE: 67
ttatttaatg atccaatgga ggggtgatt caggtaataa aaggcactcg tatggaatat       60
accaaaacat tgcgattcgt tattagcatg gatctttcaa gtaataaact tatcggagaa      120
ataccagttg agttaactgc ccttcatgcc ttggtgagtc tcaatttgtc taataatcat     180
cttattggac acattccgaa tagcattgga aacatgaaag ctttaaattc tctagatttc    240
tcgagaaacg agttaaatgg gttgatccct ccaagcattg gagctttgaa ttttttgagt    300
catttaaatt tgtcaaacaa caacttatca ggaccaattc aatcggaaa tcaattgaga     360 accctca                                                              367

<210> SEQ ID NO 68
<211> LENGTH: 321
<212> TYPE: DNA
<213> ORGANISM: Artificial Sequence
<220> FEATURE:
<223> OTHER INFORMATION: Synthetic DNA

<400> SEQUENCE: 68

```
ctagtatgga ataccaaa acattgcgat tcgttattag catggatctt tcaagtaata      60
aacttatcgg agaaatacca gttgagttaa ctgcccttca tgccttggtg agtctcaatt    120
tgtctaataa tcatcttatt ggacacattc cgaatagcat tggaaacatg aaagctttaa   180
attctctaga tttctcgaga aacgagttaa atgggttgat ccctccaagc attggagctt    240
tgaatttttt gagtcattta aatttgtcaa acaacaactt atcaggacca attccaatcg    300
gaaatcaatt gagaaccctc a                                              321
```

<210> SEQ ID NO 69
<211> LENGTH: 399
<212> TYPE: DNA
<213> ORGANISM: Stevia rebaudiana

<400> SEQUENCE: 69

```
agactcgatc gcagcctcga tcggcgagtc ggcgattgag atgatgattc attcaacaaa     60
cacatggttt gggaatagct ctgttgttgc ctcggtcggc gaatctacaa acaagagggt    120
cttcgcttcc atgtcgaacc atttgaaaac caaagctctg aataccaaat gatgcagtta    180
atgaatacaa ccaaatggct aagaacaact gattaatcaa actcttaaaa ggaaccaaga    240
ggttcaagaa caaagttctt ataaactcaa attcaatcaa aaaactgatt tgaaacttaa    300
tttcaagtgt ttaaatagaa aacatttcta aacagataaa gactaaaatt caaataatta    360
aataaagata aactataatt tgaattaaga gatgatatg                           399
```

<210> SEQ ID NO 70
<211> LENGTH: 137
<212> TYPE: DNA
<213> ORGANISM: Stevia rebaudiana

<400> SEQUENCE: 70

```
taatcatcca aaccctaatc tcgccaaaca accgaatact gatccaaacc ctgaaatgag     60
cacaactctt gaacctgatc acgagaatga agagcacaaa catgttatga cacatgtaaa   120
cgatggtttt tgctaca                                                  137
```

<210> SEQ ID NO 71
<211> LENGTH: 141
<212> TYPE: DNA
<213> ORGANISM: Stevia rebaudiana

<400> SEQUENCE: 71

```
aaggttcttt attttttaaac ttatgttaat ttattgtatc ttgtagttaa tcaagagatg    60
ctctcttgga gaaattttat ggtcataaaa cctatatcaa agagatgctc tcttggtata   120
ttccatactt aaaatatcta t                                             141
```

<210> SEQ ID NO 72
<211> LENGTH: 137
<212> TYPE: DNA
<213> ORGANISM: Stevia rebaudiana

<400> SEQUENCE: 72

```
cgatggtttt tgctacatga aaaccctaga agacgaaacc cgtttaactg taaatcttga     60
aaacacattc tttgatgaag aaccccttc gtatccggat cttatggact tttctgcatc    120
gaaaaaggac gaatacg                                                  137
```

<210> SEQ ID NO 73
<211> LENGTH: 140
<212> TYPE: DNA
<213> ORGANISM: Stevia rebaudiana

<400> SEQUENCE: 73

```
cgcaaacacg tatactaatc acgtaacata tttttattt ctaaattaaa atttgaatta      60
aagataacat aatatttatt tttagagtgt aacttctaaa aaatatcaac ctacgaaaaa    120
gttgtacata ccatgctaaa                                                140
```

<210> SEQ ID NO 74
<211> LENGTH: 367
<212> TYPE: DNA
<213> ORGANISM: Stevia rebaudiana

<400> SEQUENCE: 74

```
ttatttaatg atccaatgga gggggtgatt caggtaataa aaggcattag tatggaatat     60
accaaaacat tgcgattcgt tattagcatg gatctttcaa gtaataaact tatcggagaa    120
ataccagttg agttaactgc ccttcatgcc ttggtgagtc tcaatttgtc taataatcat    180
cttattggac acattccgaa tagcattgga aacatgaaag ctttaaattc tctagatttc    240
tcgagaaacg agttaaatgg gttgatccct ccaagcattg gagctttgaa ttttttgagt    300
catttaaatt tgtcaaacaa caacttatca ggaccaattc caatcggaaa tcaattgaga    360
accctca                                                              367
```

<210> SEQ ID NO 75
<211> LENGTH: 21
<212> TYPE: DNA
<213> ORGANISM: Stevia rebaudiana

<400> SEQUENCE: 75

```
ccaaatggct cagaacaact g                                               21
```

<210> SEQ ID NO 76
<211> LENGTH: 41
<212> TYPE: DNA
<213> ORGANISM: Stevia rebaudiana

<400> SEQUENCE: 76

```
atgaatacaa ccaaatggct cagaacaact gattaatcaa a                         41
```

<210> SEQ ID NO 77
<211> LENGTH: 61
<212> TYPE: DNA
<213> ORGANISM: Stevia rebaudiana

<400> SEQUENCE: 77

```
gatgcagtta atgaatacaa ccaaatggct cagaacaact gattaatcaa actcttaaaa     60
g                                                                    61
```

<210> SEQ ID NO 78
<211> LENGTH: 15
<212> TYPE: DNA
<213> ORGANISM: Artificial Sequence
<220> FEATURE:
<223> OTHER INFORMATION: Synthetic DNA

<400> SEQUENCE: 78

```
caaacaaccg ggtac                                                      15
```

<210> SEQ ID NO 79
<211> LENGTH: 15
<212> TYPE: DNA
<213> ORGANISM: Artificial Sequence
<220> FEATURE:
<223> OTHER INFORMATION: Synthetic DNA

<400> SEQUENCE: 79
agacattggc aactc                                                      15

<210> SEQ ID NO 80
<211> LENGTH: 15
<212> TYPE: DNA
<213> ORGANISM: Artificial Sequence
<220> FEATURE:
<223> OTHER INFORMATION: Synthetic DNA

<400> SEQUENCE: 80
atttattgta tctag                                                      15

<210> SEQ ID NO 81
<211> LENGTH: 15
<212> TYPE: DNA
<213> ORGANISM: Artificial Sequence
<220> FEATURE:
<223> OTHER INFORMATION: Synthetic DNA

<400> SEQUENCE: 81
gtacacatgc tacac                                                      15

<210> SEQ ID NO 82
<211> LENGTH: 15
<212> TYPE: DNA
<213> ORGANISM: Artificial Sequence
<220> FEATURE:
<223> OTHER INFORMATION: Synthetic DNA

<400> SEQUENCE: 82
acgaaacccg cttaa                                                      15

<210> SEQ ID NO 83
<211> LENGTH: 15
<212> TYPE: DNA
<213> ORGANISM: Artificial Sequence
<220> FEATURE:
<223> OTHER INFORMATION: Synthetic DNA

<400> SEQUENCE: 83
taatccttga attag                                                      15

<210> SEQ ID NO 84
<211> LENGTH: 15
<212> TYPE: DNA
<213> ORGANISM: Artificial Sequence
<220> FEATURE:
<223> OTHER INFORMATION: Synthetic DNA

<400> SEQUENCE: 84
acacgtatac taatc                                                      15

<210> SEQ ID NO 85
<211> LENGTH: 15
<212> TYPE: DNA
<213> ORGANISM: Artificial Sequence
<220> FEATURE:

<223> OTHER INFORMATION: Synthetic DNA

<400> SEQUENCE: 85
catggtatgt acaac                                                    15

<210> SEQ ID NO 86
<211> LENGTH: 20
<212> TYPE: DNA
<213> ORGANISM: Artificial Sequence
<220> FEATURE:
<223> OTHER INFORMATION: Synthetic DNA

<400> SEQUENCE: 86
ttcaggtaat aaaaggcctt                                               20

<210> SEQ ID NO 87
<211> LENGTH: 20
<212> TYPE: DNA
<213> ORGANISM: Artificial Sequence
<220> FEATURE:
<223> OTHER INFORMATION: Synthetic DNA

<400> SEQUENCE: 87
ttcaggtaat aaaaggcact                                               20

<210> SEQ ID NO 88
<211> LENGTH: 20
<212> TYPE: DNA
<213> ORGANISM: Artificial Sequence
<220> FEATURE:
<223> OTHER INFORMATION: Synthetic DNA

<400> SEQUENCE: 88
ttcaggtaat aaaaggctta                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic DNA

<400> SEQUENCE: 89
ttcaggtaat aaaaggcttg                                               20

<210> SEQ ID NO 90
<211> LENGTH: 20
<212> TYPE: DNA
<213> ORGANISM: Artificial Sequence
<220> FEATURE:
<223> OTHER INFORMATION: Synthetic DNA

<400> SEQUENCE: 90
ttcaggtaat aaaaggcctc                                               20

<210> SEQ ID NO 91
<211> LENGTH: 20
<212> TYPE: DNA
<213> ORGANISM: Artificial Sequence
<220> FEATURE:
<223> OTHER INFORMATION: Synthetic DNA

<400> SEQUENCE: 91
ttcaggtaat aaaaggcacg                                               20

<210> SEQ ID NO 92
<211> LENGTH: 20
<212> TYPE: DNA
<213> ORGANISM: Artificial Sequence
<220> FEATURE:
<223> OTHER INFORMATION: Synthetic DNA

<400> SEQUENCE: 92
ttcaggtaat aaaagtcatg                                               20

<210> SEQ ID NO 93
<211> LENGTH: 20
<212> TYPE: DNA
<213> ORGANISM: Artificial Sequence
<220> FEATURE:
<223> OTHER INFORMATION: Synthetic DNA

<400> SEQUENCE: 93
ttcaggtaat aaaaggctrt                                               20

<210> SEQ ID NO 94
<211> LENGTH: 20
<212> TYPE: DNA
<213> ORGANISM: Artificial Sequence
<220> FEATURE:
<223> OTHER INFORMATION: Synthetic DNA

<400> SEQUENCE: 94
ttcaggtaat aaaaggcttr                                               20

<210> SEQ ID NO 95
<211> LENGTH: 20
<212> TYPE: DNA
<213> ORGANISM: Artificial Sequence
<220> FEATURE:
<223> OTHER INFORMATION: Synthetic DNA

<400> SEQUENCE: 95
ttcaggtaat aaaaggcagc                                               20

<210> SEQ ID NO 96
<211> LENGTH: 20
<212> TYPE: DNA
<213> ORGANISM: Artificial Sequence
<220> FEATURE:
<223> OTHER INFORMATION: Synthetic DNA

<400> SEQUENCE: 96
ttcaggtaat aaaaggcycg                                               20

<210> SEQ ID NO 97
<211> LENGTH: 20
<212> TYPE: DNA
<213> ORGANISM: Artificial Sequence
<220> FEATURE:
<223> OTHER INFORMATION: Synthetic DNA

<400> SEQUENCE: 97
ttcaggtaat aaaagtgatc                                               20

<210> SEQ ID NO 98
<211> LENGTH: 20
<212> TYPE: DNA
<213> ORGANISM: Artificial Sequence
<220> FEATURE:
<223> OTHER INFORMATION: Synthetic DNA

```
<400> SEQUENCE: 98
ttcaggtaat aaaagggagg                                               20

<210> SEQ ID NO 99
<211> LENGTH: 20
<212> TYPE: DNA
<213> ORGANISM: Artificial Sequence
<220> FEATURE:
<223> OTHER INFORMATION: Synthetic DNA

<400> SEQUENCE: 99
ttcaggtaat aaaaggctgc                                               20

<210> SEQ ID NO 100
<211> LENGTH: 20
<212> TYPE: DNA
<213> ORGANISM: Artificial Sequence
<220> FEATURE:
<223> OTHER INFORMATION: Synthetic DNA

<400> SEQUENCE: 100
ttcaggtaat aaaaggaacc                                               20

<210> SEQ ID NO 101
<211> LENGTH: 20
<212> TYPE: DNA
<213> ORGANISM: Artificial Sequence
<220> FEATURE:
<223> OTHER INFORMATION: Synthetic DNA

<400> SEQUENCE: 101
ttcaggtaat aaaaggctga                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic DNA

<400> SEQUENCE: 102
ttcaggtaat aaaaggctgg                                               20

<210> SEQ ID NO 103
<211> LENGTH: 20
<212> TYPE: DNA
<213> ORGANISM: Artificial Sequence
<220> FEATURE:
<223> OTHER INFORMATION: Synthetic DNA

<400> SEQUENCE: 103
ttcaggtaat aaaaggggtg                                               20

<210> SEQ ID NO 104
<211> LENGTH: 20
<212> TYPE: DNA
<213> ORGANISM: Artificial Sequence
<220> FEATURE:
<223> OTHER INFORMATION: Synthetic DNA

<400> SEQUENCE: 104
ttcaggtaat aaaaggtctg                                               20

<210> SEQ ID NO 105
<211> LENGTH: 20
```

```
<212> TYPE: DNA
<213> ORGANISM: Artificial Sequence
<220> FEATURE:
<223> OTHER INFORMATION: Synthetic DNA

<400> SEQUENCE: 105
ttcaggtaat aaaagggaag                                          20

<210> SEQ ID NO 106
<211> LENGTH: 20
<212> TYPE: DNA
<213> ORGANISM: Artificial Sequence
<220> FEATURE:
<223> OTHER INFORMATION: Synthetic DNA

<400> SEQUENCE: 106
ttcaggtaat aaaaggtcgt                                          20

<210> SEQ ID NO 107
<211> LENGTH: 20
<212> TYPE: DNA
<213> ORGANISM: Artificial Sequence
<220> FEATURE:
<223> OTHER INFORMATION: Synthetic DNA

<400> SEQUENCE: 107
ttcaggtaat aaaagttata                                          20

<210> SEQ ID NO 108
<211> LENGTH: 20
<212> TYPE: DNA
<213> ORGANISM: Artificial Sequence
<220> FEATURE:
<223> OTHER INFORMATION: Synthetic DNA

<400> SEQUENCE: 108
ttcaggtaat aaaaggctcg                                          20

<210> SEQ ID NO 109
<211> LENGTH: 20
<212> TYPE: DNA
<213> ORGANISM: Artificial Sequence
<220> FEATURE:
<223> OTHER INFORMATION: Synthetic DNA

<400> SEQUENCE: 109
ttcaggcgat aaaaggcgtt                                          20

<210> SEQ ID NO 110
<211> LENGTH: 20
<212> TYPE: DNA
<213> ORGANISM: Artificial Sequence
<220> FEATURE:
<223> OTHER INFORMATION: Synthetic DNA

<400> SEQUENCE: 110
tgttttggta tattccatac                                          20

<210> SEQ ID NO 111
<211> LENGTH: 48
<212> TYPE: DNA
<213> ORGANISM: Artificial Sequence
<220> FEATURE:
<223> OTHER INFORMATION: Synthetic DNA

<400> SEQUENCE: 111
```
ttatttaatg atccaatgga ggggtgatt caggtaataa aaggcctt           48

<210> SEQ ID NO 112
<211> LENGTH: 48
<212> TYPE: DNA
<213> ORGANISM: Artificial Sequence
<220> FEATURE:
<223> OTHER INFORMATION: Synthetic DNA

<400> SEQUENCE: 112
ttatttaatg atccaatgga ggggtgatt caggtaataa aaggcact           48

<210> SEQ ID NO 113
<211> LENGTH: 48
<212> TYPE: DNA
<213> ORGANISM: Artificial Sequence
<220> FEATURE:
<223> OTHER INFORMATION: Synthetic DNA

<400> SEQUENCE: 113
ttatttaatg atccaatgga ggggtgatt caggtaataa aaggctta           48

<210> SEQ ID NO 114
<211> LENGTH: 48
<212> TYPE: DNA
<213> ORGANISM: Artificial Sequence
<220> FEATURE:
<223> OTHER INFORMATION: Synthetic DNA

<400> SEQUENCE: 114
ttatttaatg atccaatgga ggggtgatt caggtaataa aaggcttg           48

<210> SEQ ID NO 115
<211> LENGTH: 48
<212> TYPE: DNA
<213> ORGANISM: Artificial Sequence
<220> FEATURE:
<223> OTHER INFORMATION: Synthetic DNA

<400> SEQUENCE: 115
ttatttaatg atccaatgga ggggtgatt caggtaataa aaggcctc           48

<210> SEQ ID NO 116
<211> LENGTH: 48
<212> TYPE: DNA
<213> ORGANISM: Artificial Sequence
<220> FEATURE:
<223> OTHER INFORMATION: Synthetic DNA

<400> SEQUENCE: 116
ttatttaatg atccaatgga ggggtgatt caggtaataa aaggcacg           48

<210> SEQ ID NO 117
<211> LENGTH: 48
<212> TYPE: DNA
<213> ORGANISM: Artificial Sequence
<220> FEATURE:
<223> OTHER INFORMATION: Synthetic DNA

<400> SEQUENCE: 117
ttatttaatg atccaatgga ggggtgatt caggtaataa aagtcatg           48

<210> SEQ ID NO 118
<211> LENGTH: 48
<212> TYPE: DNA
<213> ORGANISM: Artificial Sequence
<220> FEATURE:
<223> OTHER INFORMATION: Synthetic DNA

<400> SEQUENCE: 118
ttatttaatg atccaatgga gggggtgatt caggtaataa aaggctrt            48

<210> SEQ ID NO 119
<211> LENGTH: 48
<212> TYPE: DNA
<213> ORGANISM: Artificial Sequence
<220> FEATURE:
<223> OTHER INFORMATION: Synthetic DNA

<400> SEQUENCE: 119
ttatttaatg atccaatgga gggggtgatt caggtaataa aaggcttr            48

<210> SEQ ID NO 120
<211> LENGTH: 48
<212> TYPE: DNA
<213> ORGANISM: Artificial Sequence
<220> FEATURE:
<223> OTHER INFORMATION: Synthetic DNA

<400> SEQUENCE: 120
ttatttaatg atccaatgga gggggtgatt caggtaataa aaggcagc            48

<210> SEQ ID NO 121
<211> LENGTH: 48
<212> TYPE: DNA
<213> ORGANISM: Artificial Sequence
<220> FEATURE:
<223> OTHER INFORMATION: Synthetic DNA

<400> SEQUENCE: 121
ttatttaatg atccaatgga gggggtgatt caggtaataa aaggcycg            48

<210> SEQ ID NO 122
<211> LENGTH: 48
<212> TYPE: DNA
<213> ORGANISM: Artificial Sequence
<220> FEATURE:
<223> OTHER INFORMATION: Synthetic DNA

<400> SEQUENCE: 122
ttatttaatg atccaatgga gggggtgatt caggtaataa aagtgatc            48

<210> SEQ ID NO 123
<211> LENGTH: 48
<212> TYPE: DNA
<213> ORGANISM: Artificial Sequence
<220> FEATURE:
<223> OTHER INFORMATION: Synthetic DNA

<400> SEQUENCE: 123
ttatttaatg atccaatgga gggggtgatt caggtaataa aagggagg            48

<210> SEQ ID NO 124
<211> LENGTH: 48
<212> TYPE: DNA
<213> ORGANISM: Artificial Sequence
<220> FEATURE:
<223> OTHER INFORMATION: Synthetic DNA

<400> SEQUENCE: 124
ttatttaatg atccaatgga gggggtgatt caggtaataa aaggctgc            48

```
<210> SEQ ID NO 125
<211> LENGTH: 48
<212> TYPE: DNA
<213> ORGANISM: Artificial Sequence
<220> FEATURE:
<223> OTHER INFORMATION: Synthetic DNA

<400> SEQUENCE: 125
ttatttaatg atccaatgga gggggtgatt caggtaataa aaggaacc                48

<210> SEQ ID NO 126
<211> LENGTH: 48
<212> TYPE: DNA
<213> ORGANISM: Artificial Sequence
<220> FEATURE:
<223> OTHER INFORMATION: Synthetic DNA

<400> SEQUENCE: 126
ttatttaatg atccaatgga gggggtgatt caggtaataa aaggctga                48

<210> SEQ ID NO 127
<211> LENGTH: 48
<212> TYPE: DNA
<213> ORGANISM: Artificial Sequence
<220> FEATURE:
<223> OTHER INFORMATION: Synthetic DNA

<400> SEQUENCE: 127
ttatttaatg atccaatgga gggggtgatt caggtaataa aaggctgg                48

<210> SEQ ID NO 128
<211> LENGTH: 48
<212> TYPE: DNA
<213> ORGANISM: Artificial Sequence
<220> FEATURE:
<223> OTHER INFORMATION: Synthetic DNA

<400> SEQUENCE: 128
ttatttaatg atccaatgga gggggtgatt caggtaataa aaggggtg                48

<210> SEQ ID NO 129
<211> LENGTH: 48
<212> TYPE: DNA
<213> ORGANISM: Artificial Sequence
<220> FEATURE:
<223> OTHER INFORMATION: Synthetic DNA

<400> SEQUENCE: 129
ttatttaatg atccaatgga gggggtgatt caggtaataa aaggtctg                48

<210> SEQ ID NO 130
<211> LENGTH: 48
<212> TYPE: DNA
<213> ORGANISM: Artificial Sequence
<220> FEATURE:
<223> OTHER INFORMATION: Synthetic DNA

<400> SEQUENCE: 130
ttatttaatg atccaatgga gggggtgatt caggtaataa aagggaag                48

<210> SEQ ID NO 131
<211> LENGTH: 48
<212> TYPE: DNA
<213> ORGANISM: Artificial Sequence
<220> FEATURE:
<223> OTHER INFORMATION: Synthetic DNA
```

<400> SEQUENCE: 131
ttatttaatg atccaatgga ggggtgatt caggtaataa aaggtcgt							48

<210> SEQ ID NO 132
<211> LENGTH: 48
<212> TYPE: DNA
<213> ORGANISM: Artificial Sequence
<220> FEATURE:
<223> OTHER INFORMATION: Synthetic DNA

<400> SEQUENCE: 132
ttatttaatg atccaatgga ggggtgatt caggtaataa aagttata							48

<210> SEQ ID NO 133
<211> LENGTH: 48
<212> TYPE: DNA
<213> ORGANISM: Artificial Sequence
<220> FEATURE:
<223> OTHER INFORMATION: Synthetic DNA

<400> SEQUENCE: 133
ttatttaatg atccaatgga ggggtgatt caggtaataa aaggctcg							48

<210> SEQ ID NO 134
<211> LENGTH: 48
<212> TYPE: DNA
<213> ORGANISM: Artificial Sequence
<220> FEATURE:
<223> OTHER INFORMATION: Synthetic DNA

<400> SEQUENCE: 134
ttatttaatg atccaatgga ggggtgatt caggcgataa aaggcgtt							48

<210> SEQ ID NO 135
<211> LENGTH: 21
<212> TYPE: DNA
<213> ORGANISM: Stevia rebaudiana

<400> SEQUENCE: 135
aaccgaatac cgatccaaac c							21

<210> SEQ ID NO 136
<211> LENGTH: 21
<212> TYPE: DNA
<213> ORGANISM: Stevia rebaudiana

<400> SEQUENCE: 136
ttgtatcttg aagttaatca a							21

<210> SEQ ID NO 137
<211> LENGTH: 21
<212> TYPE: DNA
<213> ORGANISM: Stevia rebaudiana

<400> SEQUENCE: 137
acccgtttaa gtgtaaatct t							21

<210> SEQ ID NO 138
<211> LENGTH: 38
<212> TYPE: DNA
<213> ORGANISM: Stevia rebaudiana

<400> SEQUENCE: 138
attaaaattt tataacaata tcatacttga attaaaga                              38

<210> SEQ ID NO 139
<211> LENGTH: 41
<212> TYPE: DNA
<213> ORGANISM: Stevia rebaudiana

<400> SEQUENCE: 139
ctcgccaaac aaccgaatac cgatccaaac cctgaaatga g                         41

<210> SEQ ID NO 140
<211> LENGTH: 41
<212> TYPE: DNA
<213> ORGANISM: Stevia rebaudiana

<400> SEQUENCE: 140
tgttaattta ttgtatcttg aagttaatca agagatgctc t                         41

<210> SEQ ID NO 141
<211> LENGTH: 41
<212> TYPE: DNA
<213> ORGANISM: Stevia rebaudiana

<400> SEQUENCE: 141
agaagacgaa acccgtttaa gtgtaaatct tgaaaacaca t                         41

<210> SEQ ID NO 142
<211> LENGTH: 58
<212> TYPE: DNA
<213> ORGANISM: Stevia rebaudiana

<400> SEQUENCE: 142
ttatttctaa attaaaattt tataacaata tcatacttga attaaagata acataata       58

<210> SEQ ID NO 143
<211> LENGTH: 61
<212> TYPE: DNA
<213> ORGANISM: Stevia rebaudiana

<400> SEQUENCE: 143
aaaccctaat ctcgccaaac aaccgaatac cgatccaaac cctgaaatga gcacaactct     60
t                                                                     61

<210> SEQ ID NO 144
<211> LENGTH: 61
<212> TYPE: DNA
<213> ORGANISM: Stevia rebaudiana

<400> SEQUENCE: 144
tttaaactta tgttaattta ttgtatcttg aagttaatca agagatgctc tcttggagaa     60
a                                                                     61

<210> SEQ ID NO 145
<211> LENGTH: 61
<212> TYPE: DNA
<213> ORGANISM: Stevia rebaudiana

<400> SEQUENCE: 145
tgaaaaccct agaagacgaa acccgtttaa gtgtaaatct tgaaaacaca ttctttgatg     60
a                                                                     61

```
<210> SEQ ID NO 146
<211> LENGTH: 78
<212> TYPE: DNA
<213> ORGANISM: Stevia rebaudiana

<400> SEQUENCE: 146
aacatatttt ttatttctaa attaaaattt tataacaata tcatacttga attaaagata    60
acataatatt tattttta                                                  78

<210> SEQ ID NO 147
<211> LENGTH: 21
<212> TYPE: DNA
<213> ORGANISM: Stevia rebaudiana

<400> SEQUENCE: 147
aaaaggcatt cgtatggaat a                                              21

<210> SEQ ID NO 148
<211> LENGTH: 41
<212> TYPE: DNA
<213> ORGANISM: Stevia rebaudiana

<400> SEQUENCE: 148
ttcaggtaat aaaaggcatt cgtatggaat ataccaaaac a                        41

<210> SEQ ID NO 149
<211> LENGTH: 61
<212> TYPE: DNA
<213> ORGANISM: Stevia rebaudiana

<400> SEQUENCE: 149 gaggggggtga ttcaggtaat aaaaggcatt cgtatggaat ataccaaaac attgcgattc   60
g                                                                    61

<210> SEQ ID NO 150
<211> LENGTH: 169
<212> TYPE: DNA
<213> ORGANISM: Stevia rebaudiana

<400> SEQUENCE: 150
gtcaagaaat cgtgtgctat gagagcccaa gaccgtcaat gggaattcat cgtatggttt    60
ttctgttgtt tcgacaattg ggtcgacaaa cggtgtacgc cccagggtgg cgccagaatt   120
tcaacacaag agactttgca gagctctaca accttgggtc tcctgttgc               169

<210> SEQ ID NO 151
<211> LENGTH: 20
<212> TYPE: DNA
<213> ORGANISM: Artificial sequence
<220> FEATURE:
<223> OTHER INFORMATION: Synthetic DNA

<400> SEQUENCE: 151
agagcccaag accgtcaatg                                                20

<210> SEQ ID NO 152
<211> LENGTH: 20
<212> TYPE: DNA
<213> ORGANISM: Artificial sequence
<220> FEATURE:
<223> OTHER INFORMATION: Synthetic DNA

<400> SEQUENCE: 152
```
gcaacaggag acccaaggtt                                                    20

<210> SEQ ID NO 153
<211> LENGTH: 21
<212> TYPE: DNA
<213> ORGANISM: Stevia rebaudiana

<400> SEQUENCE: 153
gggtcgacaa gcggtgtacg c                                                  21

<210> SEQ ID NO 154
<211> LENGTH: 35
<212> TYPE: DNA
<213> ORGANISM: Stevia rebaudiana

<400> SEQUENCE: 154
gacaattggg tcgacaagcg gtgtacgccc caggg                                   35

<210> SEQ ID NO 155
<211> LENGTH: 21
<212> TYPE: DNA
<213> ORGANISM: Stevia rebaudiana

<400> SEQUENCE: 155
cgccccaggg gggcgccaga a                                                  21

<210> SEQ ID NO 156
<211> LENGTH: 35
<212> TYPE: DNA
<213> ORGANISM: Stevia rebaudiana

<400> SEQUENCE: 156
cggtgtacgc cccaggggggg cgccagaatt tcaac                                  35

<210> SEQ ID NO 157
<211> LENGTH: 25
<212> TYPE: DNA
<213> ORGANISM: Artificial sequence
<220> FEATURE:
<223> OTHER INFORMATION: Synthetic DNA

<400> SEQUENCE: 157
gtcaagaaat cgtgtgctat gagag                                              25

<210> SEQ ID NO 158
<211> LENGTH: 25
<212> TYPE: DNA
<213> ORGANISM: Artificial sequence
<220> FEATURE:
<223> OTHER INFORMATION: Synthetic DNA

<400> SEQUENCE: 158
tggcgccccc ctggggcgta cacag                                              25

<210> SEQ ID NO 159
<211> LENGTH: 115
<212> TYPE: DNA
<213> ORGANISM: Artificial sequence
<220> FEATURE:
<223> OTHER INFORMATION: Synthetic DNA

<400> SEQUENCE: 159
gtcaagaaat cgtgtgctat gagagcccaa gaccgtcaat gggaattcat cgtatggttt        60
ttctgttgtt tcgacaattg ggtcgacaag ctgtgtacgc cccaggggggg cgcca           115

```
<210> SEQ ID NO 160
<211> LENGTH: 90
<212> TYPE: DNA
<213> ORGANISM: Artificial sequence
<220> FEATURE:
<223> OTHER INFORMATION: Synthetic DNA

<400> SEQUENCE: 160
gtcaagaaat cgtgtgctat gagagcccaa gaccgtcaat gggaattcat cgtatggttt      60
ttctgttgtt tcgacaattg ggtcgacaag                                        90

<210> SEQ ID NO 161
<211> LENGTH: 25
<212> TYPE: DNA
<213> ORGANISM: Artificial sequence
<220> FEATURE:
<223> OTHER INFORMATION: Synthetic DNA

<400> SEQUENCE: 161
ctgtgtacgc cccaggggggg cgcca                                            25

<210> SEQ ID NO 162
<211> LENGTH: 115
<212> TYPE: DNA
<213> ORGANISM: Artificial sequence
<220> FEATURE:
<223> OTHER INFORMATION: Synthetic DNA

<400> SEQUENCE: 162
gtcaagaaat cgtgtgctat gagagcccaa gaccgtcaat gggaattcat cgtatggttt      60
ttctgttgtt tcgacaattg ggtcgacaaa ctgtgtacgc cccaggggggg cgcca         115

<210> SEQ ID NO 163
<211> LENGTH: 29
<212> TYPE: DNA
<213> ORGANISM: Artificial sequence
<220> FEATURE:
<223> OTHER INFORMATION: Synthetic DNA

<400> SEQUENCE: 163
aaagtctctt gtgttgaaat tctggggcc                                         29

<210> SEQ ID NO 164
<211> LENGTH: 137
<212> TYPE: DNA
<213> ORGANISM: Artificial sequence
<220> FEATURE:
<223> OTHER INFORMATION: Synthetic DNA

<400> SEQUENCE: 164
gtcaagaaat cgtgtgctat gagagcccaa gaccgtcaat gggaattcat cgtatggttt      60
ttctgttgtt tcgacaattg ggtcgacaag cggtgtacgc cccaggggggg ccccagaatt    120 tcaacacaag agacttt                                                     137

<210> SEQ ID NO 165
<211> LENGTH: 112
<212> TYPE: DNA
<213> ORGANISM: Artificial sequence
<220> FEATURE:
<223> OTHER INFORMATION: Synthetic DNA

<400> SEQUENCE: 165
```

```
gtcaagaaat cgtgtgctat gagagcccaa gaccgtcaat gggaattcat cgtatggttt      60
ttctgttgtt tcgacaattg ggtcgacaag cggtgtacgc cccagggggg cc              112
```

<210> SEQ ID NO 166
<211> LENGTH: 25
<212> TYPE: DNA
<213> ORGANISM: Artificial sequence
<220> FEATURE:
<223> OTHER INFORMATION: Synthetic DNA

<400> SEQUENCE: 166

```
ccagaatttc aacacaagag acttt                                            25
```

<210> SEQ ID NO 167
<211> LENGTH: 137
<212> TYPE: DNA
<213> ORGANISM: Artificial sequence
<220> FEATURE:
<223> OTHER INFORMATION: Synthetic DNA

<400> SEQUENCE: 167

```
gtcaagaaat cgtgtgctat gagagcccaa gaccgtcaat gggaattcat cgtatggttt      60
ttctgttgtt tcgacaattg ggtcgacaaa ctgtgtacgc cccagggtgg ccccagaatt     120
tcaacacaag agacttt                                                    137
```

<210> SEQ ID NO 168
<211> LENGTH: 21
<212> TYPE: DNA
<213> ORGANISM: Stevia rebaudiana

<400> SEQUENCE: 168

```
gggtcgacaa acggtgtacg c                                                21
```

<210> SEQ ID NO 169
<211> LENGTH: 35
<212> TYPE: DNA
<213> ORGANISM: Stevia rebaudiana

<400> SEQUENCE: 169

```
gacaattggg tcgacaaacg gtgtacgccc caggg                                 35
```

<210> SEQ ID NO 170
<211> LENGTH: 21
<212> TYPE: DNA
<213> ORGANISM: Stevia rebaudiana

<400> SEQUENCE: 170

```
cgccccaggg tggcgccaga a                                                21
```

<210> SEQ ID NO 171
<211> LENGTH: 35
<212> TYPE: DNA
<213> ORGANISM: Stevia rebaudiana

<400> SEQUENCE: 171

```
cggtgtacgc cccagggtgg cgccagaatt tcaac                                 35
```

<210> SEQ ID NO 172
<211> LENGTH: 25
<212> TYPE: DNA
<213> ORGANISM: Artificial sequence
<220> FEATURE:
<223> OTHER INFORMATION: Synthetic DNA

<400> SEQUENCE: 172
tggcgccccc ctggggcgta cacgg					25

<210> SEQ ID NO 173
<211> LENGTH: 25
<212> TYPE: DNA
<213> ORGANISM: Artificial sequence
<220> FEATURE:
<223> OTHER INFORMATION: Synthetic DNA

<400> SEQUENCE: 173
tggcgccccc ctggggcgta cagcg					25

<210> SEQ ID NO 174
<211> LENGTH: 25
<212> TYPE: DNA
<213> ORGANISM: Artificial sequence
<220> FEATURE:
<223> OTHER INFORMATION: Synthetic DNA

<400> SEQUENCE: 174
tggcgccccc ctggggcgta cgccg					25

<210> SEQ ID NO 175
<211> LENGTH: 25
<212> TYPE: DNA
<213> ORGANISM: Artificial sequence
<220> FEATURE:
<223> OTHER INFORMATION: Synthetic DNA

<400> SEQUENCE: 175
tggcgccccc ctggggcgta cagct					25

<210> SEQ ID NO 176
<211> LENGTH: 25
<212> TYPE: DNA
<213> ORGANISM: Artificial sequence
<220> FEATURE:
<223> OTHER INFORMATION: Synthetic DNA

<400> SEQUENCE: 176
tggcgccccc ctggggcata cactg					25

<210> SEQ ID NO 177
<211> LENGTH: 25
<212> TYPE: DNA
<213> ORGANISM: Artificial sequence
<220> FEATURE:
<223> OTHER INFORMATION: Synthetic DNA

<400> SEQUENCE: 177
tggcgccccc ctggggcgta cgcag					25

<210> SEQ ID NO 178
<211> LENGTH: 25
<212> TYPE: DNA
<213> ORGANISM: Artificial sequence
<220> FEATURE:
<223> OTHER INFORMATION: Synthetic DNA

<400> SEQUENCE: 178
tggcgccccc ctggggccta cacgg					25

<210> SEQ ID NO 179

```
<211> LENGTH: 25
<212> TYPE: DNA
<213> ORGANISM: Artificial sequence
<220> FEATURE:
<223> OTHER INFORMATION: Synthetic DNA

<400> SEQUENCE: 179
tggcgccccc ctggggagta cacct                                    25

<210> SEQ ID NO 180
<211> LENGTH: 25
<212> TYPE: DNA
<213> ORGANISM: Artificial sequence
<220> FEATURE:
<223> OTHER INFORMATION: Synthetic DNA

<400> SEQUENCE: 180
tggcgccccc ctggggcgta caaca                                    25

<210> SEQ ID NO 181
<211> LENGTH: 25
<212> TYPE: DNA
<213> ORGANISM: Artificial sequence
<220> FEATURE:
<223> OTHER INFORMATION: Synthetic DNA

<400> SEQUENCE: 181
tggcgccccc ctggggcgta cacgt                                    25

<210> SEQ ID NO 182
<211> LENGTH: 25
<212> TYPE: DNA
<213> ORGANISM: Artificial sequence
<220> FEATURE:
<223> OTHER INFORMATION: Synthetic DNA

<400> SEQUENCE: 182
tggcgccccc ctggggcgta cgacg                                    25

<210> SEQ ID NO 183
<211> LENGTH: 25
<212> TYPE: DNA
<213> ORGANISM: Artificial sequence
<220> FEATURE:
<223> OTHER INFORMATION: Synthetic DNA

<400> SEQUENCE: 183
tggcgccccc ctggggcgta caaag                                    25

<210> SEQ ID NO 184
<211> LENGTH: 29
<212> TYPE: DNA
<213> ORGANISM: Artificial sequence
<220> FEATURE:
<223> OTHER INFORMATION: Synthetic DNA

<400> SEQUENCE: 184
aaagtctctt gtgttgaaat tctggcgcg                                29

<210> SEQ ID NO 185
<211> LENGTH: 29
<212> TYPE: DNA
<213> ORGANISM: Artificial sequence
<220> FEATURE:
<223> OTHER INFORMATION: Synthetic DNA

<400> SEQUENCE: 185
```
aaagtctctt gtgttgaaat tctggggcc                                             29

<210> SEQ ID NO 186
<211> LENGTH: 29
<212> TYPE: DNA
<213> ORGANISM: Artificial sequence
<220> FEATURE:
<223> OTHER INFORMATION: Synthetic DNA

<400> SEQUENCE: 186
aaagtctctt gtgttgaaat tctggcggc                                             29

<210> SEQ ID NO 187
<211> LENGTH: 29
<212> TYPE: DNA
<213> ORGANISM: Artificial sequence
<220> FEATURE:
<223> OTHER INFORMATION: Synthetic DNA

<400> SEQUENCE: 187
aaagtctctt gtgttgaaat tctgggggcg                                            29

<210> SEQ ID NO 188
<211> LENGTH: 29
<212> TYPE: DNA
<213> ORGANISM: Artificial sequence
<220> FEATURE:
<223> OTHER INFORMATION: Synthetic DNA

<400> SEQUENCE: 188
aaagtctctt gtgttgaaat tctgccgct                                             29

<210> SEQ ID NO 189
<211> LENGTH: 29
<212> TYPE: DNA
<213> ORGANISM: Artificial sequence
<220> FEATURE:
<223> OTHER INFORMATION: Synthetic DNA

<400> SEQUENCE: 189
aaagtctctt gtgttgaaat tctggtgca                                             29

<210> SEQ ID NO 190
<211> LENGTH: 29
<212> TYPE: DNA
<213> ORGANISM: Artificial sequencev
<220> FEATURE:
<223> OTHER INFORMATION: Synthetic DNA

<400> SEQUENCE: 190
aaagtctctt gtgttgaaat tctggagct                                             29

<210> SEQ ID NO 191
<211> LENGTH: 29
<212> TYPE: DNA
<213> ORGANISM: Artificial sequence
<220> FEATURE:
<223> OTHER INFORMATION: Synthetic DNA

<400> SEQUENCE: 191
aaagtctctt gtgttgaaat tctggagac                                             29

<210> SEQ ID NO 192
<211> LENGTH: 20
<212> TYPE: DNA

```
<213> ORGANISM: Artificial sequence
<220> FEATURE:
<223> OTHER INFORMATION: Synthetic DNA

<400> SEQUENCE: 192
ttcaggtaat aaaaggcatt                                              20
```